US010273230B2

(12) United States Patent
Kumar et al.

(10) Patent No.: US 10,273,230 B2
(45) Date of Patent: Apr. 30, 2019

(54) SUBSTITUTED PHENYL ALKANOIC ACID COMPOUNDS AS GPR120 AGONISTS AND USES THEREOF

(71) Applicant: Piramal Enterprises Limited, Mumbai (IN)

(72) Inventors: Sanjay Kumar, Mumbai (IN); Rajiv Sharma, Fremont, CA (US); Vijaykumar Bhagwan Deore, Mumbai (IN); Nilambari Nilkanth Yewalkar, Pune (IN)

(73) Assignee: Piramal Enterprises Limited, Mumbai (IN)

( * ) Notice: Subject to any disclaimer, the term of this patent is extended or adjusted under 35 U.S.C. 154(b) by 0 days.

(21) Appl. No.: 15/328,450

(22) PCT Filed: Jul. 23, 2015

(86) PCT No.: PCT/IB2015/055572
§ 371 (c)(1),
(2) Date: Jan. 23, 2017

(87) PCT Pub. No.: WO2016/012965
PCT Pub. Date: Jan. 28, 2016

(65) Prior Publication Data
US 2017/0210731 A1    Jul. 27, 2017

Related U.S. Application Data

(60) Provisional application No. 62/028,891, filed on Jul. 25, 2014.

(51) Int. Cl.
| | | |
|---|---|---|
| *C07D 409/04* | (2006.01) |
| *C07D 405/14* | (2006.01) |
| *C07D 215/14* | (2006.01) |
| *C07C 59/72* | (2006.01) |
| *C07C 255/46* | (2006.01) |
| *C07C 255/54* | (2006.01) |
| *C07D 213/73* | (2006.01) |
| *C07D 309/24* | (2006.01) |
| *C07D 333/16* | (2006.01) |
| *C07D 405/04* | (2006.01) |
| *C07D 277/64* | (2006.01) |
| *C07D 213/30* | (2006.01) |
| *C07D 213/64* | (2006.01) |
| *C07D 307/79* | (2006.01) |
| *C07C 59/66* | (2006.01) |

(52) U.S. Cl.
CPC ............ *C07D 409/04* (2013.01); *C07C 59/66* (2013.01); *C07C 59/72* (2013.01); *C07C 255/46* (2013.01); *C07C 255/54* (2013.01); *C07D 213/30* (2013.01); *C07D 213/64* (2013.01); *C07D 213/73* (2013.01); *C07D 215/14* (2013.01); *C07D 277/64* (2013.01); *C07D 307/79* (2013.01); *C07D 309/24* (2013.01); *C07D 333/16* (2013.01); *C07D 405/04* (2013.01); *C07D 405/14* (2013.01); *C07C 2601/02* (2017.05); *C07C 2601/10* (2017.05); *C07C 2601/14* (2017.05); *C07C 2601/16* (2017.05); *C07C 2601/18* (2017.05); *C07C 2602/06* (2017.05); *C07C 2602/08* (2017.05); *C07C 2602/28* (2017.05)

(58) Field of Classification Search
CPC ... C07D 409/04; C07D 213/30; C07D 215/14
See application file for complete search history.

(56) References Cited

U.S. PATENT DOCUMENTS

| | | | |
|---|---|---|---|
| 5,789,423 A | 8/1998 | Wakabayashi et al. |
| 8,299,296 B2 | 10/2012 | Shimada et al. |
| 8,367,708 B2 | 2/2013 | Hashimoto et al. |
| 2011/0065739 A1 | 3/2011 | Ishikawa et al. |
| 2011/0313003 A1 | 12/2011 | Shi et al. |
| 2012/0115861 A1 | 5/2012 | Calderini et al. |
| 2013/0217781 A1 | 8/2013 | Carroll et al. |
| 2014/0069963 A1 | 3/2014 | Stein |
| 2016/0347768 A1 | 12/2016 | Kumar et al. |
| 2017/0283410 A1 | 10/2017 | Kumar et al. |

FOREIGN PATENT DOCUMENTS

| | | |
|---|---|---|
| CN | 104046350 | 9/2014 |
| EP | 1 688 138 A1 | 8/2006 |
| EP | 2 125 758 A1 | 12/2009 |
| GB | 990397 | 4/1965 |
| GB | 1139607 | 1/1969 |

(Continued)

OTHER PUBLICATIONS

Registry No. 1027427-54-8, entered in STN on Jun. 11, 2008.*
Registry No. 1025918-57-3, entered in STN on Jun. 6, 2008.*
Registry No. 1026475-19-3, entered in STN on Jun. 8, 2008.*
Registry No. 1026489-82-6, entered in STN on Jun. 8, 2008.*
Registry No. 1026500-58-2, entered in STN on Jun. 8, 2008.*
Vippagunta, et al. Advanced Drug Delivery Reviews 48 (2001) 3-26.*
Concise Encyclopedia Chemistry (1993) Walter de Gruyter Berlin New York.*

(Continued)

*Primary Examiner* — Shawquia Jackson
(74) *Attorney, Agent, or Firm* — Foley & Lardner LLP

(57) ABSTRACT

The present invention relates to substituted phenyl alkanoic acid compounds designated as the compound of Formula (I) (as described herein) or a tautomer, a stereoisomer, a geometrical isomer, a pharmaceutically acceptable salt, a pharmaceutically acceptable solvate, a prodrug, a polymorph, an N-oxide, a S-oxide or a carboxylic acid isostere thereof; which are GPR120 agonists. The present invention also relates to a pharmaceutical composition of compound of Formula (I) for the treatment of diseases or disorder mediated by GPR120.

18 Claims, No Drawings

(56) References Cited

FOREIGN PATENT DOCUMENTS

| | | |
|---|---|---|
| WO | WO-2005/086661 | 9/2005 |
| WO | WO-2008/103500 | 8/2008 |
| WO | WO-2009/038204 | 3/2009 |
| WO | WO-2009/054479 | 4/2009 |
| WO | WO-2010/008831 | 1/2010 |
| WO | WO-2010/048207 A2 | 4/2010 |
| WO | WO-2010/080537 | 7/2010 |
| WO | WO-2010/104195 | 9/2010 |
| WO | WO-2011/072132 | 6/2011 |
| WO | WO-2011/159297 | 12/2011 |
| WO | WO-2013/128378 | 9/2013 |
| WO | WO-2013/139341 | 9/2013 |
| WO | WO-2013/185766 | 12/2013 |
| WO | WO-2013/185766 A1 | 12/2013 |
| WO | WO-2014/059232 | 4/2014 |
| WO | WO-2015/125085 | 2/2015 |
| WO | WO-2016/022446 | 2/2016 |

OTHER PUBLICATIONS

International Search Report and Written Opinion, PCT/IB2015/055572, Piramel Enterprises Limited, 17 pages (dated Jan. 21, 2016).
CAS Registry No. 1025918-57-3, STN Entry Date Jun. 6, 2008 3-(2-((2-(6-aminonaphthalen-2-yl)cyclopentyl)methoxy)phenyl)propanoic acid.
CAS Registry No. 1026475-19-3, STN Entry Date Jun. 8, 2008 2-[[2-[6-(carboxymethoxy)-2-naphthalenyl]cyclohexyl]methoxy]-benzenepropanoic acid.
CAS Registry No. 1026489-82-6, STN Entry Date Jun. 8, 2008 methyl 3-(2-((2-(6-aminonaphthalen-2-yl)cyclopentyl)methoxy)phenyl)propanoate.
CAS Registry No. 1026500-58-2, STN Entry Date Jun. 8, 2008 6-[2-[[2-(2-carboxyethyl)phenoxy]methyl]cyclohexyl]-2-naphthalenecarboxylic acid.
CAS Registry No. 1027427-54-8, STN Entry Date Jun. 11, 2008 2-[[2-(7-amino-2-naphthalenyl)cyclopentyl]methoxy]-benzenepropanoic acid.
CAS Registry No. 1027654-19-8, STN Entry Date Jun. 12, 2008 6-[2-[[2-(3-methoxy-3-oxopropyl)phenoxy]methyl]cyclohexyl]-2-naphthalenecarboxylic acid.
CAS Registry No. 1027894-93-4, STN Entry Date Jun. 13, 2008 2-[[2-(7-amino-2-naphthalenyl)cyclopentyl]methoxy]-benzenepropanoic acid methyl ester.
CAS Registry No. 1287459-87-3, STN Entry Date Apr. 29, 2011 rel-3-[[[(2R,3S)-2-(2-fluoro-5-methoxyphenyl)-6-oxo-3-piperidinyl]amino]methyl]-1H-indole-1-acetamide.
CAS Registry No. 1287467-25-7, STN Entry Date Apr. 29, 2011 rel-3-[[[(2R,3S)-2-(2-fluoro-5-methoxyphenyl)-6-oxo-3-piperidinyl]amino]methyl]-1H-indole-1-propanamide.
CAS Registry No. 1346947-23-6, STN Entry Date Dec. 1, 2011 3,4-dihydro-7-[[[(3R,4R)-4-[4-[3-[(2-methoxyphenyl)methoxy]propoxy]phenyl]-3-piperidinyl]oxy]methyl]-1(2H)-quinolineethanesulfonamide.
CAS Registry No. 1347559-94-7, STN Entry Date Dec. 2, 2011 3-[[[(2S,3S)-2-phenyl-3-piperidinyl]amino]methyl]-4-(2,2,2-trifluoroethoxy)-benzeneacetamide.
CAS Registry No. 1553145-75-7, STN Entry Date Feb. 23, 2014 5-[[[2-(1H-imidazol-1-yl)cyclopentyl]amino]methyl]-2-thiopheneacetic acid.
CAS Registry No. 1627272-79-0, STN Entry Date Sep. 28, 2014 methyl 2-(4-(((2-phenyltetrahydro-2H-pyran-3-yl)methyl)amino)-1H-pyrazolo[3,4-d]pyrimidin-1-yl)acetate.
CAS Registry No. 1645359-44-9, STN Entry Date Feb. 8, 2015 N-methyl-4-[[(2-phenylcyclopentyl)amino]methyl]-2-thiazoleacetamide.
CAS Registry No. 173160-56-0, STN Entry Date Feb. 13, 1996 [1S-(exo,exo)]--2-[[3-[4-[[(4-cyclohexylbutyl)amino]carbonyl]-2-oxazolyl]-7-oxabicyclo[2.2.1]hept-2-yl]methoxy]-benzeneacetic acid.
CAS RN 536695-50-8; STN entry date: Jun. 24, 2003. 3-(4-aminobutyl)-2-[ I , I '-biphenyl]-4-yl-I H-indole-5-acetic acid.
CAS RN 536695-51-9; STN entry date: Jun. 24, 2003. 3-(4-aminobutyl)-2-[I ,I '-biphenyl]-2-yl-I H-indole-5-acetic acid.
Deng, G. et al, "Identification of benzoxazole analogs as novel, S1 P3 sparing SlP1 agonists", Bioorganic & Medicinal Chemistry Letters, 2012, vol. 22, pp. 3973-3977 Abstract; Compounds 16d, 16f, Table 3, p. 3976.
Duncton et al., "Preparation of Heteroaryloxetanes and Heteroarylazetidines by Use of a Minisci Reaction", J. Org. Chem., (2009), 74(16):6354-6357.
Guda et al., "An efficient synthesis of styryl 1,3,4-thiadiazoles using Lawesson's reagent and propylphosphonic anhydride-precursors for bis heterocycles", Arabian Journal of Chemistry (2014) 7, 947-954 (available online Aug. 29, 2014).
Kahn, S.E., "The importance of the beta-cell in the pathogenesis of type 2 diabetes mellitus", Am. J. Med., 2000, 108(6, Suppl 1):25-85.
Kwon et al., "Adipokines mediate inflammation and insulin resistance", Frontiers Endocrinol., 2013, 4:1-11. PMID: 23781214.
Marhraoui et al., "Synthese de nouveaux glycosyl-1,2,3-triazoles 1,4-disubstitues", J. Maroc. Chim. Hétérocyclique., 2010, 9(1):59-67. (No Abstract Available).
Muralkirishna et al., "Synthesis, antimicrobial and cytotoxic activities of sulfone linked bis heterocycles", European Journal of Medicinal Chemistry, 2012, 54:605-614.
National Diabetes Statistics Report (2014)(12 pages).
Padmaja et al., "Synthesis and antimicrobial activity of pyrrolyl/pyrazolyl arylaminosulfonylmethyl 1,3,4-oxadiazoles, 1,3,4-thiadiazoles and 1,2,4-triazoles", Chem. Pharm. Bull., 2011, 59(11)1509-1517.
Paulsen et al., "Expression of the Fatty Acid Receptor GPR120 in the Gut of Diet-Induced-Obese Rats and Its Role in GLP-1 Secretion", PLOS one, 2014, 9(2):e88227, pp. 1-6.
PCT International Search Report and Written Opinion for Application No. PCT/IB2015/051232 dated May 18, 2015.
PCT International Search Report and Written Opinion for Application No. PCT/IB2015/056891 dated Mar. 7, 2016.
Reddy et al., "Synthesis and antioxidant activity of a new class of mono- and bis-heterocycles", Arch. Pharm. Chem. Life Sci., 2013, 346:154-162.
Reddy et al., "Synthesis and antioxidant activity of styrylsulfonylmethyl 1,3,4-oxadiazoles, pyrazolyl/isoxazolyl-1,3,4-oxadiazoles", Chem. Pharm. Bull., 2013, 61(12):1291-1297.
Shimpukade et al., "Discovery of a Potent and Selective GPR120 Agonist", J. Med. Chem., 2012, 55:4511-4515.
Siddiqui et al., "BRET biosensor analysis of receptor tyrosine kinase functionality", Frontiers in Endocrinology, (2013), vol. 4, article 46, p. 1-11.
Suckow et al., "Alteration of the Glucagon Axis in GPR120 (FFAR4) Knockout Mice. A Role for GPR120 in Glucagon Secretion", J. Biol Chem., 2014, 289(22):15751-15763.
Talukdar et al., "Targeting GPR120 and other fatty acid-sensing GPCRs ameliorates insulin resistance and inflammatory diseases", Trends Pharmacol Sci., 2011, 32(9):543-550.
Talukdar et al., "Targeting GPR120 and other fatty acid sensing GPCRs ameliorates insulin resistance and inflammatory diseases", Trends Pharmacol. Sci., 2011, 32(9):543-550; pp. 1-15.
Wild et al., "Global prevalence of diabetes: estimates for the year 2000 and projections for 2030", Diabetes Care, 2004, 27(5):1047-1053.
Guda et al., "An efficient synthesis of styryl 1,3,4-thiadiazoles using Lawesson's reagent and Propylphosphonic anhydride-precursors for bis heterocycles", Arabian Journal of Chemistry, 2014, 7:947-954.

\* cited by examiner

SUBSTITUTED PHENYL ALKANOIC ACID COMPOUNDS AS GPR120 AGONISTS AND USES THEREOF

CROSS-REFERENCE TO RELATED APPLICATIONS

This application is a U.S. National Stage Application of PCT/IB2015/055572, filed Jul. 23, 2015, which claims the benefit of and priority to U.S. Provisional Patent Application No. 62/028,891, filed Jul. 25, 2014, the entire contents of both of which are incorporated herein by reference.

FIELD OF THE INVENTION

The present invention relates to phenyl alkanoic acid compounds represented by the compounds of Formula (I) (as described herein), processes for their preparation, pharmaceutical compositions comprising said compounds, and methods for their use for the prophylaxis and/or treatment of a disease or a disorder mediated by GPR120 receptor.

BACKGROUND OF THE INVENTION

Metabolic diseases or disorders are caused by an abnormal metabolic process and can either be congenital due to an inherited enzyme abnormality or acquired due to a disease of an endocrine organ or failure of a metabolically important organ such as the liver or the pancreas.

Among the metabolic disorders, diabetes mellitus is the most prevalent and is considered to be one of the five leading causes of death in the world (Diabetes Care, 2004, vol. 27, 1047-1053). According to the National Diabetes Statistics Report (2014), around 29.1 million people or 9.3% of the population in the United States have diabetes. Diabetes mellitus is typically classified into two main subtypes: Type 1 and Type 2 diabetes mellitus. Type 1 diabetes mellitus (also known as Insulin Dependent Diabetes Mellitus or IDDM), which generally occurs in adolescents under 20 years of age, is an auto-immune disease causing an insulitis with the subsequent destruction of insulin-producing β-cells of the pancreas. Further, in latent autoimmune diabetes in adults (LADA), β-cells are destroyed due to autoimmune attack. The subsequent lack of insulin leads to elevated levels of blood and urine glucose (hyperglycemia). Although the exact trigger for this autoimmune response is not known, patients with Type 1 diabetes have high levels of antibodies against pancreatic beta cells (hereinafter "beta cells"). However, it cannot be ascertained that all patients with high levels of these antibodies develop Type 1 diabetes. Type 2 diabetes mellitus or non-insulin-dependent diabetes mellitus (NIDDM) is developed when human muscle, fat and liver cells are not able to respond normally to insulin that the body secretes. This inability to respond, otherwise known as insulin resistance, can be due to restriction on the numbers of insulin receptors on these cells, or a dysfunctional behaviour of signalling pathways within the cells, or both. Initially, the β-cells which are responsible for the production of insulin, compensate for this insulin resistance by increasing their insulin secretion. However, these cells gradually become unable to produce enough insulin to facilitate the normal glucose homeostasis, causing the progression to Type 2 diabetes (Am. J. Med. 2000, 108(6), Supplement 1, 2S-8S). Type 2 diabetes (T2D) is characterised by fasting hyperglycemia which occurs as an effect of the combined lesions of insulin resistance and β-cell dysfunction. There are two types of defects associated with the β-cells: the first component, an increase in the basal insulin release which usually occurs in the presence of low, non-stimulatory glucose concentrations. The second component is a failure to enhance the insulin release in response to a hyperglycaemic challenge.

Obesity is another risk factor for developing metabolic diseases or disorders such as diabetes, cardiovascular disorders, hypertension, hyperlipidemia and an increased mortality. Diabetes caused by insulin resistance and obesity are part of the "metabolic syndrome" which is defined as the linkage between several diseases (also referred to as syndrome X, insulin-resistance syndrome, or deadly quartet). These often occur in the same patients and are major risk factors for the development of Type 2 diabetes and cardiovascular diseases (Frontiers in Endocrinology, 2013, vol. 4, 1-11). It has been suggested that the control of lipid levels and/or glucose levels is required to treat type 2 diabetes and cardiovascular diseases. Even though lifestyle changes like exercise and healthy diet are regarded as the most efficient ways to prevent and manage the diseases, pharmaceutical intervention is frequently necessary.

Current treatment options for diabetes, particularly T2D, include use of hypoglycaemic agents and insulin. Metformin is one such hypoglycemic agent which is used in the treatment of Type 2 diabetes. It is, in fact, one of the oldest drugs used for the treatment of T2D and it still remains the drug of choice despite associated gastrointestinal (GI) side effects including anorexia, nausea, diarrhea and vomiting commonly associated with it. Sulfonylureas (SUs) e.g. glimepiride, glipizide, are insulin secretagogues, which act on β-cells to increase insulin release, are commonly used in the treatment of Type 2 diabetes. However, use of sulfonylureas is also associated with adverse effects in that they increase the risk of hypoglycaemia and lead to weight gain. Insulin treatment also carries the same side-effects. Thiazolidinedione compounds e.g. rosiglitazone, pioglitazone, are insulin sensitizers which bind to peroxisome proliferator-activated receptors (PPARs) in cells and thereby increase the insulin sensitivity. Though, thiazolidinedione compounds have also been widely used, the enhanced risks of cardiovascular disease and hepatotoxicity have resulted in stringent limitations on their use. Relatively recently, regulatory authorities approved new classes of anti-diabetic agents such as glucagon-like peptide-1 (GLP-1) agonists (exenatide and liraglutide) and dipeptidyl peptidase-4 (DPP-4) inhibitors (linagliptin and alogliptin).

It is a known fact that metabolic processes are regulated by fatty acids which are important biological molecules that serve both as a source of energy and as signalling molecules. Generally, it is believed that fatty acids produce their biological effects through interacting with intracellular targets including, for example, the family of peroxisome proliferator-activated receptors (PPARs). However, in the recent years it has become clear that fatty acids also serve as agonists for a group of cell surface G protein-coupled receptors (GPCRs). Free fatty acids (FFAs) have been demonstrated to act as ligands of several GPCRs including GPR40 (FFAR1), GPR43, GPR84, GPR119 and GPR120. One of the GPCR namely GPR40 facilitates glucose-stimulated insulin secretion from pancreatic β-cells, whereas the other GPCR namely GPR120 regulates the secretion of GLP-1 in the intestine, as well as insulin sensitivity in macrophages.

Among GPCRs, GPR120 is localized to intestinal enteroendocrine cells, such as colonic L cells. It is reported that GPR120 is a nutrient sensor that is activated endogenously by both saturated and unsaturated long chain fatty acids and that an altered glucagon axis contributes to the impaired glucose homeostasis. Thus, targeting GPR120 for diabetes can impact glucose homeostasis in part through altering glucagon secretion and islet function (J. Biol Chem., 2014, 289 (22):15751-15763).

GPR120 is reported as a target for the treatment of type 2 diabetes, obesity, and other metabolic diseases and also, for inflammatory disorders (J. Med. Chem. 2012, 55, 4511-4515; Trends Pharmacol Sci. 2011, vol. 32(9), 543-550). An expression of GPR120 in the gut epithelium reports indicating a putative role of GPR120 as a sensor of dietary fat (PLOS one, 2014, 9(2), e88227). Certain research studies conducted relatively recently identified that loss-of-function of GPR120 human variant is associated with obesity, diabetes and other insulin resistance, and related metabolic disorders and also with inflammatory disorders.

Various patent documents describe compounds which are reported to be GPR120 modulators. Examples of patent documents describing GPR120 modulators include PCT application publications WO2014059232, WO2013185766, WO2013139341, WO2011159297, WO2010080537, WO2009054479 and WO2005086661 and US application publications US2014069963, US2013217781 and US20110313003.

Thus, in view of the role of GPR120 receptor in potentiating or causing metabolic disorders such as diabetes and related disorders and also, inflammatory disorders, there is need in the art to develop compounds that act by modulating the GPR120 receptor pathways.

SUMMARY OF THE INVENTION

In one aspect, the present invention relates to a compound of Formula (I) (as described herein) or a tautomer, a stereoisomer, a geometrical isomer, a pharmaceutically acceptable salt, a pharmaceutically acceptable solvate, a prodrug, a polymorph, an N-oxide, a S-oxide or a carboxylic acid isostere thereof.

In another aspect, the present invention relates to a process for the preparation of the compounds of Formula (I) or pharmaceutically acceptable salts thereof.

In another aspect, the present invention relates to a pharmaceutical composition comprising a therapeutically effective amount of a compound of Formula (I) or a tautomer, a stereoisomer, a geometrical isomer, a pharmaceutically acceptable salt or a pharmaceutically acceptable solvate thereof and at least one pharmaceutically acceptable carrier or excipient.

In a further aspect, the present invention relates to a pharmaceutical composition comprising a therapeutically effective amount of a compound of Formula (I) or a tautomer, a stereoisomer, a geometrical isomer, a pharmaceutically acceptable salt or a pharmaceutically acceptable solvate thereof; one or more therapeutically active agents and at least one pharmaceutically acceptable carrier or excipient.

In an aspect, the present invention relates to the compound of Formula (I) or a tautomer, a stereoisomer, a geometrical isomer, a pharmaceutically acceptable salt or a pharmaceutically acceptable solvate thereof; for use as GPR120 agonist.

In yet another aspect, the present invention relates to a compound of Formula (I) or a tautomer, a stereoisomer, a geometrical isomer, a pharmaceutically acceptable salt or a pharmaceutically acceptable solvate thereof, for use in the treatment or prophylaxis of a disease or a disorder mediated by GPR120.

In another aspect, the present invention relates to a method for the treatment or prophylaxis of a disease or a disorder mediated by GPR120, comprising administering to a subject in need thereof; a therapeutically effective amount of a compound of Formula (I) or a stereoisomer, a tautomer, a pharmaceutically acceptable salt or a pharmaceutically acceptable solvate thereof.

In another aspect, the present invention relates to use of the compound of Formula (I) or a stereoisomer, a tautomer, a pharmaceutically acceptable salt or a pharmaceutically acceptable solvate thereof; in the manufacture of a medicament, for the treatment or prophylaxis of a disease or a disorder mediated by GPR120.

In yet another aspect, the present invention relates to use of the compound of Formula (I) or a stereoisomer, a tautomer, a pharmaceutically acceptable salt or a pharmaceutically acceptable solvate thereof; in combination with at least one therapeutically active agent, for the treatment or prophylaxis of a disease or a disorder mediated by GPR120.

These and other objectives and advantages of the present invention will be apparent to those skilled in the art from the following description.

DETAILED DESCRIPTION OF THE INVENTION

In the first aspect, the present invention relates to a compound of Formula (I)

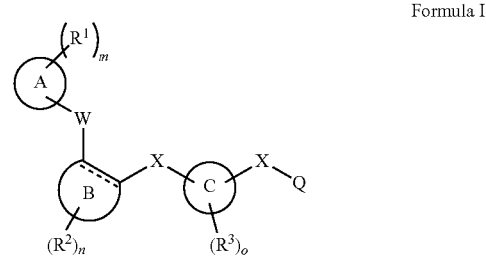

Formula I or a tautomer, a stereoisomer, a geometrical isomer, a pharmaceutically acceptable salt, a pharmaceutically acceptable solvate, a prodrug, a polymorph, an N-oxide, a S-oxide or a carboxylic acid isostere thereof;
wherein:
Ring A is 5- to 12-membered carbocycle, 5- to 12-membered heterocyclyl; $(C_6-C_{10})$aryl or 5- to 12-membered heteroaryl;
Ring B is 5- to 12-membered carbocycle or 5- to 12-membered heterocyclyl containing 1, 2, 3 or 4 heteroatoms independently selected from the group consisting of N, O and S;
Ring C is $(C_6-C_{10})$aryl or 5- to 12-membered heteroaryl containing 1, 2 or 3 heteroatoms independently selected from the group consisting of N, O and S;
W represents a bond, $-(CR^5R^6)_p-$, $-O-$, $-S-$ or $-NR^7-$;
X is $-CR^5R^6-X^1-$ or $-X^1-CR^5R^6-$, wherein $X^1$ is O, S or $NR^7$;
Y is $-(C(R^4)_2)_q-$;
Q is $-CO_2M$, $-CONH_2$, $-CONH[(C_1-C_6)alkyl]$, $-CON[(C_1-C_6)alkyl]_2$, $-CONHSO_2(C_1-C_6)alkyl$ or a carboxylic acid isostere;
M is hydrogen, deuterium or $(C_1-C_6)$alkyl;
------ represents a single bond or a double bond;

$R^1$ at each occurrence is independently selected from the group consisting of hydrogen, halogen, $(C_1-C_6)$alkyl, $(C_1-C_6)$alkenyl, halo$(C_1-C_6)$alkyl, $(C_1-C_6)$alkoxy, hydroxy, $(C_3-C_{10})$cycloalkyl, heterocyclyl, $(C_6-C_{10})$aryl, heteroaryl, $(C_6-C_{10})$aryloxy, cyano, oxo, —$NR^7R^8$, —$C(O)NR^7R^8$, —$C(S)NR^7R^8$, —$S(O)_tR^9$ and —$C(O)R^{10}$;

$R^2$ at each occurrence is independently selected from the group consisting of hydrogen, halogen, $(C_1-C_6)$alkyl, $(C_1-C_6)$alkenyl, halo$(C_1-C_6)$alkyl, $(C_1-C_6)$alkoxy, hydroxy, $(C_3-C_{10})$cycloalkyl, heterocyclyl, $(C_6-C_{10})$aryl, heteroaryl, $(C_6-C_{10})$aryloxy, cyano, oxo, —$NR^7R^8$, —$C(O)NR^7R^8$, —$C(S)NR^7R^8$, —$S(O)_tR^9$ and —$C(O)R^{10}$;

$R^3$ at each occurrence is independently selected from the group consisting of hydrogen, halogen, $(C_1-C_6)$alkyl, $(C_1-C_6)$alkoxy, hydroxy, $(C_3-C_{10})$cycloalkyl, heterocyclyl, $(C_6-C_{10})$aryl, heteroaryl, cyano, —$NR^7R^8$, —$S(O)_tR^9$ and —$C(O)R^{10}$;

$R^4$ at each occurrence is independently selected from the group consisting of hydrogen, $(C_1-C_6)$alkyl, halo$(C_1-C_6)$alkyl and halogen; or two $R^4$ groups, together with the carbon atom to which they are attached can combine to form a $(C_3-C_{10})$cycloalkyl or heterocyclyl;

$R^5$ and $R^6$ are independently selected from the group consisting of hydrogen, deuterium, $(C_1-C_6)$alkyl, halo$(C_1-C_6)$alkyl and halogen; or $R^5$ and $R^6$ together with the carbon atom to which they are attached can combine to form
i) 5- to 12-membered carbocycle or
ii) 5- to 12-membered heterocyclyl containing 1, 2, 3 or 4 heteroatoms independently selected from the group consisting of N, O and S;

$R^7$ and $R^8$ are independently selected from the group consisting of hydrogen, hydroxy, $(C_1-C_6)$alkyl, $(C_1-C_6)$alkenyl, halo$(C_1-C_6)$alkyl, $(C_1-C_6)$alkoxy, $(C_3-C_{10})$cycloalkyl, heterocyclyl, $(C_6-C_{10})$aryl, heteroaryl, $(C_6-C_{10})$aryloxy, —$S(O)_tR^9$; or $R^7$ and $R^8$, together with the nitrogen atom to which they are attached combine to form heterocyclyl;

$R^9$ and $R^{10}$ are independently selected from the group consisting of hydrogen, hydroxy, $(C_1-C_6)$alkyl, halo$(C_1-C_6)$alkyl, $(C_1-C_6)$alkoxy, $(C_3-C_{10})$cycloalkyl, heterocyclyl, $(C_6-C_{10})$aryl, heteroaryl and —$NR^7R^8$;

m is 0, 1, 2 or 3;
n is 0, 1, 2 or 3;
o is 0, 1 or 2;
p is 1 or 2;
q is 1, 2, 3 or 4;
t is 0, 1 or 2;

wherein:
$(C_1-C_6)$alkyl is unsubstituted or substituted with one or more groups independently selected from the group consisting of $(C_1-C_6)$alkyl, $(C_1-C_6)$alkenyl, halogen, halo$(C_1-C_6)$alkyl, hydroxy, $(C_1-C_6)$alkoxy, halo$(C_1-C_6)$alkoxy, $(C_3-C_{10})$cycloalkyl, $(C_6-C_{10})$aryl, $(C_6-C_{10})$aryloxy, heterocyclyl, heteroaryl, amino, cyano, nitro, —$NH(C_1-C_6)$alkyl, —$N[(C_1-C_6)$alkyl$]_2$, —$C(O)(C_1-C_6)$alkyl, —$C(O)O(C_1-C_6)$alkyl, —$C(O)NH_2$, —$C(O)NH(C_1-C_6)$alkyl, —$C(O)N[(C_1-C_6)$alkyl$]_2$ and —$C(O)NHSO_2(C_1-C_6)$alkyl;

$(C_3-C_{10})$cycloalkyl is unsubstituted or substituted with one or more groups independently selected from the group consisting of $(C_1-C_6)$alkyl, $(C_1-C_6)$alkenyl, halogen, halo$(C_1-C_6)$alkyl, hydroxy, $(C_1-C_6)$alkoxy, halo$(C_1-C_6)$alkoxy, amino, cyano and nitro;

carbocycle is a 5- to 12-membered ring which is unsubstituted or substituted with one or more groups independently selected from the group consisting of $(C_1-C_6)$alkyl, $(C_1-C_6)$alkenyl, halo$(C_1-C_6)$alkyl, hydroxy, halogen, $(C_1-C_6)$alkoxy, halo$(C_1-C_6)$alkoxy, $(C_6-C_{10})$aryl, $(C_3-C_{10})$cycloalkyl, heterocyclyl, heteroaryl, amino, cyano, nitro, —$C(O)O(C_1-C_6)$alkyl, —$C(O)NR^7R^8$ and —$S(O)_tR^9$; wherein $R^7$, $R^8$, $R^9$ and t are as defined above;

heterocyclyl is a 5- to 12-membered ring which is unsubstituted or substituted with one or more groups independently selected from the group consisting of $(C_1-C_6)$alkyl, $(C_1-C_6)$alkenyl, halogen, halo$(C_1-C_6)$alkyl, hydroxy, $(C_1-C_6)$alkoxy, halo$(C_1-C_6)$alkoxy, $(C_3-C_{10})$cycloalkyl, $(C_6-C_{10})$aryl, heterocyclyl, heteroaryl, amino, cyano, nitro, oxo, —$NR^7R^8$, —$C(O)NR^7R^8$, —$S(O)_tR^9$ and —$C(O)R^{10}$; wherein $R^7$, $R^8$, $R^9$, $R^{10}$ and t are as defined above;

$(C_6-C_{10})$aryl is unsubstituted or substituted with one or more groups independently selected from the group consisting of $(C_1-C_6)$alkyl, $(C_1-C_6)$alkenyl, halogen, halo$(C_1-C_6)$ alkyl, hydroxy, $(C_1-C_6)$alkoxy, halo$(C_1-C_6)$alkoxy, $(C_3-C_{10})$ cycloalkyl, $(C_6-C_{10})$aryl, heterocyclyl, heteroaryl, amino, cyano, nitro, —$C(O)O(C_1-C_6)$alkyl, —$C(O)NR^7R^8$ and —$S(O)_tR^9$; wherein $R^7$, $R^8$, $R^9$ and t are as defined above;

heteroaryl is a 5- to 12-membered ring which is unsubstituted or substituted with one or more groups independently selected from the group consisting of $(C_1-C_6)$alkyl, $(C_1-C_6)$alkenyl, halogen, halo$(C_1-C_6)$alkyl, hydroxy, $(C_1-C_6)$alkoxy, halo$(C_1-C_6)$alkoxy, $(C_3-C_{10})$cycloalkyl, $(C_6-C_{10})$aryl, heterocyclyl, heteroaryl, amino, cyano, nitro, —$C(O)NR^7R^8$ and —$S(O)_tR^9$; wherein $R^7$, $R^8$, $R^9$ and t are as defined above.

Definitions

Unless otherwise indicated, the following definitions are set forth to illustrate and define the meaning and scope of various terms used to describe the invention herein and the appended claims. These definitions should not be interpreted in the literal sense as they are not general definitions and are relevant only for this application.

The singular forms "a", "an" and "the" include plural aspects unless the context clearly dictates otherwise. For instance, the terms "a", "an" and "the" refer to "one or more" when used in the subject specification, including the claims. Thus, for example, reference to "a compound" includes a plurality of such compounds, or reference to "a disease" or "a condition" includes a plurality of diseases or disorders.

Also, use of "(s)" as part of a term, includes reference to the term singly or in plurality, for example the term salt(s) indicates a single salt or more than one salt of the compound of formula I.

As used herein the term "or" is generally employed in its sense including "and/or" unless the content clearly dictates otherwise.

A symbol (-) is used to indicate a point of attachment to the atom, for example —COOH is attached through the carbon atom.

Unless indicated otherwise, the term "optionally substituted" means "substituted or unsubstituted," and therefore, the generic structural formulae described herein encompasses compounds containing the specified optional substituent as well as compounds that do not contain the optional substituent. For example, the phrase "heterocyclyl is optionally substituted with one or more groups" encompasses unsubstituted heterocyclic ring, and heterocyclic ring substituted with one or more groups as described.

The term "independently" when used in the context of selection of substituents for a variable, it means that where more than one substituent is selected from a number of possible substituents, those substituents can be the same or different.

Within the context of the present application and as used herein, the term "unsaturated" means that a moiety has one or more units of unsaturation.

Within the context of the present application and as used herein, the term "partially unsaturated" refers to a ring moiety that includes at least one double bond between ring atoms but is not aromatic.

Within the context of the present application and as used herein, the term "$(C_1-C_6)$alkyl" or "alkyl"; alone or as part of a substituent group, refers to the radical of saturated aliphatic groups, including straight or branched-chain alkyl groups. A straight-chain or branched chain alkyl has six or fewer carbon atoms in its backbone, for instance, $C_1-C_6$ for straight chain and $C_3-C_6$ for branched chain. As used herein, $(C_1-C_6)$alkyl refers to an alkyl group having 1 to 6 (both inclusive) carbon atoms; preferably an alkyl group having 1 to 4 (both inclusive) carbon atoms i.e. $(C_1-C_4)$alkyl. Representative examples of alkyl include, but are not limited to, methyl, ethyl, n-propyl, n-butyl, n-pentyl, n-hexyl, isopropyl, sec-butyl, isobutyl, tert-butyl, isopentyl, 2-methylbutyl and 3-methylbutyl. In the "$(C_1-C_6)$alkyl" group, one or more carbon atoms can be optionally replaced with one or more heteroatoms independently selected from the group consisting of N, O and S.

Furthermore, the alkyl group can be unsubstituted or substituted with one or more groups; preferably with 1-4 groups, independently selected from the group consisting of $(C_1-C_6)$alkyl, $(C_1-C_6)$alkenyl, halogen, halo$(C_1-C_6)$alkyl, hydroxy, $(C_1-C_6)$alkoxy, halo$(C_1-C_6)$alkoxy, $(C_3-C_{10})$cycloalkyl, $(C_6-C_{10})$aryl, $(C_6-C_{10})$aryloxy, heterocyclyl, heteroaryl, amino, cyano, nitro, —NH$(C_1-C_6)$alkyl, —N[$(C_1-C_6)$alkyl]$_2$, —C(O)$(C_1-C_6)$alkyl, —C(O)O$(C_1-C_6)$alkyl, —C(O)NH$_2$, —C(O)NH$(C_1-C_6)$alkyl, —C(O)N[$(C_1-C_6)$alkyl]$_2$ and —C(O)NHSO$_2(C_1-C_6)$alkyl.

Within the context of the present application, the term "$(C_1-C_6)$alkenyl" or "alkenyl", as used herein, alone or as part of a substituent group, refers to an unsaturated straight or branched chain hydrocarbon radical containing at least one carbon-carbon double bond (two adjacent sp$^2$ carbon atoms). For example, the term "$(C_1-C_6)$alkenyl" refers to an alkenyl group having two to six carbon atoms. Depending upon the placement of double bond and substituents if any, the geometry of the double bond can be entgegen (E), or zusammen (Z), cis or trans. Examples of alkenyl include, but are not limited to, vinyl, allyl or 2-propenyl. Unless indicated otherwise, the alkenyl groups can be unsubstituted or substituted with one or more of groups independently selected from the group consisting of $(C_1-C_6)$alkyl, halogen, haloalkyl, hydroxy, —O$(C_1-C_6)$alkyl, amino, nitro and cyano.

Within the context of the present application and as used herein, the term "halo$(C_1-C_6)$alkyl" or "haloalkyl" refers to the alkyl group which is substituted with one or more halogens. A monohalo$(C_1-C_6)$alkyl radical, for example, can have one chlorine, bromine, iodine or fluorine atom. Dihalo and polyhalo$(C_1-C_6)$alkyl radicals can have two or more of the same or different halogen atoms. Representative examples of halo$(C_1-C_6)$alkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluorochloromethyl, dichlorofluoromethyl, difluoroethyl, difluoropropyl and the like groups.

Within the context of the present application and as used herein, the term "$(C_1-C_6)$alkoxy" or "alkoxy" refers to a $(C_1-C_6)$alkyl having an oxygen radical attached thereto. The term "$(C_1-C_6)$alkoxy" or "—O$(C_1-C_6)$alkyl" or alkoxy wherever used in this specification have the same meaning. Representative examples of alkoxy groups include, but are not limited to, methoxy, ethoxy, propoxy, isopropoxy, n-butoxy, isobutoxy and t-butoxy. Furthermore, the alkoxy groups can be unsubstituted or substituted with one or more groups. A substituted alkoxy refers to a $(C_1-C_6)$alkoxy substituted with 1-5 groups, preferably with 1-3 groups selected from the groups indicated above as the substituents for the alkyl group.

Within the context of the present application and as used herein, the term "halo$(C_1-C_6)$alkoxy" or "—O$(C_1-C_6)$haloalkyl" refers to radicals wherein one or more hydrogen atoms of the $(C_1-C_6)$alkoxy group are substituted with one or more halogens. The terms "halo$(C_1-C_6)$alkoxy" or "—O$(C_1-C_6)$haloalkyl" or "haloalkoxy" wherever used in this specification have the same meaning. Representative examples of halo$(C_1-C_6)$alkoxy groups include, but are not limited to, difluoromethoxy (—OCHF$_2$), trifluoromethoxy (—OCF$_3$) and trifluoroethoxy (—OCH$_2$CF$_3$).

Within the context of the present application and as used herein, the term "carbocycle" or "carbocyclic ring" refers to a saturated or partially unsaturated 5- to 12-membered ring system; preferably 5- to 10-membered and more preferably 5- to 7-membered ring system. The carbocycle can be monocyclic or bicyclic ring system. Representative examples of carbocycle include, but are not limited to, cyclopentyl, cyclopentenyl, cyclohexyl, cyclohexenyl, cycloheptanyl, cycloheptenyl, cyclooctenyl and decahydronaphthyl. Furthermore, the carbocycle can be unsubstituted or substituted with one or more groups, preferably with 1-7 groups, more preferably with 1-3 groups, independently selected from the group consisting of $(C_1-C_6)$alkyl, $(C_1-C_6)$alkenyl, halo$(C_1-C_6)$alkyl, hydroxy, halogen, $(C_1-C_6)$alkoxy, halo$(C_1-C_6)$alkoxy, $(C_3-C_{10})$cycloalkyl, heterocyclyl, $(C_6-C_{10})$aryl, heteroaryl, amino, cyano, nitro, oxo, —NR$^7$R$^8$, —C(O)NR$^7$R$^8$, —C(S)NR$^7$R$^8$, —S(O)$_r$R$^9$ and —C(O)R$^{10}$; wherein R$^7$, R$^8$, R$^9$ and are as defined above.

Within the context of the present application and as used herein, As used herein, the term "$(C_3-C_{10})$cycloalkyl" or "cycloalkyl" to a monocyclic hydrocarbon ring containing three to ten carbon atoms. Representative $(C_3-C_{10})$cycloalkyl groups include, but are not limited to, cyclopropyl, cyclobutyl, cyclopentyl, cyclohexyl, cycloheptyl and cyclooctyl. Unless stated otherwise, $(C_3-C_{10})$cycloalkyl can be unsubstituted or substituted with one or more groups independently selected from the group consisting of $(C_1-C_6)$alkyl, $(C_1-C_6)$alkenyl, halogen, halo$(C_1-C_6)$alkyl, hydroxy, $(C_1-C_6)$alkoxy, halo$(C_1-C_6)$alkoxy, amino, cyano and nitro.

Within the context of the present application and as used herein, the terms "heterocyclyl" or "heterocyclic" refers to a saturated or partially unsaturated 5- to 12-membered ring system; preferably 5- to 10-membered and more preferably 5- to 7-membered ring system. The heterocyclic ring can be a monocyclic or bicyclic ring system containing 1 to 4 heteroatoms independently selected from the group consisting of oxygen, nitrogen and sulfur. Saturated heterocyclic ring systems do not contain any double bond, whereas partially unsaturated heterocyclic ring systems, can contain at least one double bond, but do not form an aromatic system. The oxidized form of the ring nitrogen and sulfur atom contained in the heterocyclyl to provide the corresponding N-oxide, S-oxide or S,S-dioxide is also encompassed in the scope of the present invention. Representative examples of saturated and partially unsaturated heterocyclic groups include but are not limited to, dihydrofuran tetrahydrofuran, tetrahydrothiophene, dihydrothiene, tetrahydrothiene, dihydropyran, tetrahydropyran, thio-tetrahydropyran, tetrahydrothiopyran, 2-pyrrolin, 3-pyrrolin, pyrrolidin, isoxazolidine, 1,3-thiazinane, 2,3-dihydrofuran, pyrazolidine, pyrazolidin, imidazoline, 1,2,3,6-tetrahydropyridine, piperidine, piperidino, piperazine, morpholine, 1,3-oxazinane, 4,5,6-tetrahydropyrimidine, and tetrahydropyridine.

Furthermore, the heterocyclyl groups can be unsubstituted or substituted with one or more groups, preferably with 1-7 groups, more preferably with 1-3 groups independently selected from the group consisting of $(C_1-C_6)$alkyl, $(C_1-C_6)$alkenyl, halogen, halo$(C_1-C_6)$alkyl, hydroxy, $(C_1-C_6)$alkoxy, halo$(C_1-C_6)$alkoxy, $(C_3-C_{10})$cycloalkyl, $(C_6-C_{10})$aryl, heterocyclyl, heteroaryl, amino, cyano, nitro, oxo, —$NR^7R^8$, —$C(O)NR^7R^8$, —$S(O)_tR^9$ and —$C(O)R^{10}$; wherein $R^7$, $R^8$, $R^9$, $R^{10}$ and t are as defined above.

Within the context of the present application and as used herein, the term "$(C_6-C_{10})$aryl" or "aryl" refers to a monocyclic or bicyclic hydrocarbon groups having 6 to 10 carbon atoms in which the carbocyclic ring(s) present have a conjugated pi electron system, which can be optionally substituted by one or more groups. The term "$(C_6-C_{10})$aryl" includes a monocyclic or bicyclic ring system. The bicyclic ring system contains two fused rings, of which one ring is saturated or unsaturated 5- or 6-membered aryl or 5- or 6-membered carbocycle or 5- or 6-membered heteroaryl ring containing 1 to 4 heteroatoms independently selected from the group consisting of oxygen, nitrogen and sulphur. Representative examples of $(C_6-C_{10})$aryl include, but are not limited to, phenyl and naphthyl.

Furthermore, the aryl group can be unsubstituted or substituted with one or more groups. A substituted aryl refers to a $(C_6-C_{10})$aryl substituted with one or more groups, preferably 1 to 7 groups and more preferably 1 to 3 groups independently selected from the group consisting of $(C_1-C_6)$alkyl, $(C_1-C_6)$alkenyl, $(C_2-C_5)$alkynyl, halogen, halo$(C_1-C_6)$alkyl, hydroxy, $(C_1-C_6)$alkoxy, halo$(C_1-C_6)$alkoxy, $(C_3-C_{10})$cycloalkyl, $(C_6-C_{10})$aryl, heterocyclyl, heteroaryl, amino, cyano, nitro, —$C(O)O(C_1-C_6)$alkyl, —$C(O)NR^7R^8$ and —$S(O)_tR^9$. Aryl groups can be substituted in any desired position. For example, in monosubstituted phenyl, the substituent can be located in the 2-position, the 3-position, the 4-position or the 5-position. If the phenyl carries two substituents, they can be located in 2,3-position, 2,4-position, 2,5-position, 2,6-position, 3,4-position or 3,5-position. Examples of monosubstituted phenyl groups include, but are not limited to, 2-fluorophenyl, 2-ethoxyphenyl, 2-ethylphenyl, 4-morpholinophenyl, (4-ethylpiperazin-1-yl)phenyl or 4-(2-dimethylaminoethyl)phenyl. Examples of disubstituted phenyl groups include, but not limited to, 2,6-difluorophenyl and 3,5-difluorophenyl.

Within the context of the present application and as used herein, the term "—$O(C_6-C_{10})$aryl" or "aryloxy" refers to $(C_6-C_{10})$aryl group having an oxygen radical attached thereto. The terms aryloxy or —$O(C_6-C_{10})$aryl wherever used in this specification have the same meaning. Representative aryloxy groups include, but are not limited to, phenoxy or naphthoxy. Furthermore, —$O(C_6-C_{10})$aryl is unsubstituted or substituted with one or more groups as defined herein above for the term "aryl".

Within the context of the present application and as used herein, the term "heteroaryl", whether used alone or as part of a substituent group, refers to 5- to 12-membered, preferably 5- to 10-membered and more preferably 5- to 7-membered ring aromatic ring containing one to four identical or different heteroatoms independently selected from the group consisting of oxygen, nitrogen and sulfur atom. The term "heteroaryl" includes a monocyclic or bicyclic ring system. Representative examples of heteroaryls include, but are not limited to, pyrrole, pyrazole, imidazole, tetrazole, pyrazine, furan, thiophene, oxazole, oxadiazole, thiazole, benzimidazole, benzoxazole, triazole, benzothiazole, benzofuran, indole, isoindole, cinnoline, indazole, isoindole, thiadiazole, isoquinoline, benzoxazole, thiophene, benzothiazole, isoxazole, triazine, purine, pyridine, quinoline, isoquinoline, phenazine, oxadiazole, carbazole, pyridazine, quinazoline, pyrimidine, isothiazole, quinoxaline (benzopyrazine), tetrazole and pyrido[2,3-b]pyrazine. The oxidized form of the ring nitrogen and sulfur atom contained in the heteroaryl to provide the corresponding N-oxide, S-oxide or S,S-dioxide is also encompassed in the scope of the present invention.

Furthermore, the heteroaryl groups can be unsubstituted or substituted with one or more groups; preferably with 1-7 groups, more preferably with 1-3 groups independently selected from the group consisting of $(C_1-C_6)$alkyl, $(C_1-C_6)$alkenyl, halogen, halo$(C_1-C_6)$alkyl, hydroxy, $(C_1-C_6)$alkoxy, halo$(C_1-C_6)$alkoxy, $(C_3-C_{10})$cycloalkyl, $(C_6-C_{10})$aryl, heterocyclyl, heteroaryl, amino, cyano, nitro, —$C(O)NR^7R^8$ and —$S(O)_tR^9$; wherein $R^7$, $R^8$, $R^9$ and t are as defined above.

Within the context of the present application and as used herein, the term "heteroatom" includes nitrogen (N), oxygen (O) and sulfur (S). Further, the heteroatom with unsatisfied valency is assumed to have a hydrogen atom or it can be substituted with a group selected from $(C_1-C_6)$alkyl or —$C(O)(C_1-C_6)$alkyl. Representative examples of $(C_1-C_6)$alkyl group can be selected from, but not limited to methyl, ethyl, propyl, butyl, pentyl, hexyl, isopropyl and isobutyl.

Within the context of the present application and as used herein, the term "halogen" refers to chlorine, fluorine, bromine or iodine.

Within the context of the present application and as used herein, the term "amino" refers to the group "$NH_2$" which can be optionally substituted by one or more substituents. Examples of substituents include, but not limited to, $(C_1-C_4)$alkyl and $(C_6-C_{10})$aryl groups.

Within the context of the present invention and as used herein, the terms "compound of Formula (I)", "compounds of Formula (I)", and "compound of the present invention" are used interchangeably throughout this application, include all stereoisomeric and tautomeric forms and mixtures thereof in all ratios, pharmaceutically acceptable salts, solvates, prodrugs, N-oxides, S-oxides or carboxylic acid isosteres thereof. Further, in the context of the present invention, reference to the compounds of Formula (I) includes reference to the compounds represented herein by the compounds of Formula Ia and/or the compounds of one or more embodiments of the present invention as described herein. The compound(s) of the present invention can also be referred to herein as "the active compound(s)" or "the active ingredient(s)".

Within the context of the present application and as used herein, the term "tautomer" refers to the coexistence of two or more compounds that differ from each other only in the position of one (or more) mobile atoms and in electron distribution. In fact, tautomers are structural isomers of different energies which are interconvertible via a low energy barrier. For example, proton tautomers (also known as prototropic tautomers) include interconversions via migration of a proton, such as keto-enol and imine-enamine isomerizations.

Within the context of the present application and as used herein, the term "stereoisomer" is used for all isomers of individual compounds (in the present invention, the compound of Formula (I)) that differ only in the orientation of their atoms in space. The term stereoisomer includes mirror image isomers (enantiomers), mixtures of mirror image isomers (racemates, racemic mixtures), geometric (cis/trans or E/Z) isomers, and isomers of compounds with more than one chiral center that are not mirror images of one another (diastereoisomers).

Within the context of the present application and as used herein, the term "pharmaceutically acceptable" refers to the carrier, diluent, excipient, and/or salt which must be compatible with the other ingredients of the formulation, and not deleterious to the recipient thereof.

Within the context of the present application and as used herein, the term "pharmaceutically acceptable carrier" refers to a material that is non-toxic, inert, solid, semi-solid or liquid filler, diluent, encapsulating material or formulation auxiliary or excipient of any type which is suitable for a subject, preferably a mammal, more preferably a human, and is suitable for delivering an active agent to the target site without affecting the activity of the agent.

Within the context of the present application and as used herein, the term "pharmaceutically acceptable salt(s)" includes a salt or salts of the active compound i.e. the compound of Formula (I), which retains the desired biological activity of the subject compound and exhibit minimal undesired toxicological effects; and are prepared with suitable acids or bases, depending on the particular substituents found on the compounds described herein.

Within the context of the present application and as used herein, the term "pharmaceutically acceptable solvate" or "solvate(s)" refers to a compound formed by the interaction of a solute (in the present invention, a compound of Formula (I) or a pharmaceutically acceptable salt thereof) and a solvent. Preferably, the solvent used is a pharmaceutically acceptable solvent. Examples of suitable pharmaceutically acceptable solvents include, but are not limited to, water, ethanol and acetic acid. Most preferably, the solvent used is water and the solvates obtained are referred to as hydrates. Examples for suitable solvates are the mono- or di-hydrates or alcoholates of the compounds according to the invention.

Within the context of the present application and as used herein, the term "prodrug(s)" refers to any pharmacologically inactive or less active compound which, when metabolized or chemically transformed in vivo by a chemical or physiological process, e.g., a prodrug on being brought to the physiological pH or through enzyme action is converted to the parent compound e.g. the compound of Formula (I) of the present invention. For example, in the context of the present invention prodrugs can be esters of the compound of Formula (I) which on metabolism the ester group is cleaved to form the active compound of Formula (I). Examples of esters include, but are not limited to, lower alkyl esters such as methyl or ethyl ester; carboxy-lower alkyl esters such as the carboxymethyl ester; nitrooxy- or nitrosooxy-lower alkyl esters, such as 4-nitrooxybutyl or 4-nitrosooxybutyl ester.

Within the context of the present application and as used herein, the terms "polymorph" or "polymorphic form" refer to crystals of the same compound that differs only in the arrangement and/or conformation of the molecule in the crystal lattice.

Within the context of the present application and as used herein, the term "N-oxide" refers to the oxide of the nitrogen atom of a nitrogen-containing heteroaryl or heterocyclic ring. N-oxide can be formed in the presence of an oxidizing agent for example peroxide such as m-chloroperbenzoic acid or hydrogen peroxide. N-oxide refers to an amine oxide, also known as amine-N-oxide, and is a chemical compound that contains N→O bond.

Within the context of the present application and as used herein, the term "S-oxide" refers to the oxide of the sulfur atom (S-oxide) or dioxide of the sulfur atom (S,S-dioxide) of a sulfur-containing heteroaryl or heterocyclic ring. S-oxide and S,S-dioxides can be formed in the presence of an oxidizing agent for example peroxide such as m-chloroperbenzoic acid or oxone.

Within the context of the present application and as used herein, the phrase, "carboxylic acid isostere" refers to a functional group or a moiety that elicits similar physical, biological and/or chemical properties as a carboxylic acid moiety. Representative examples of carboxylic acid isostere include, but are not limited to:

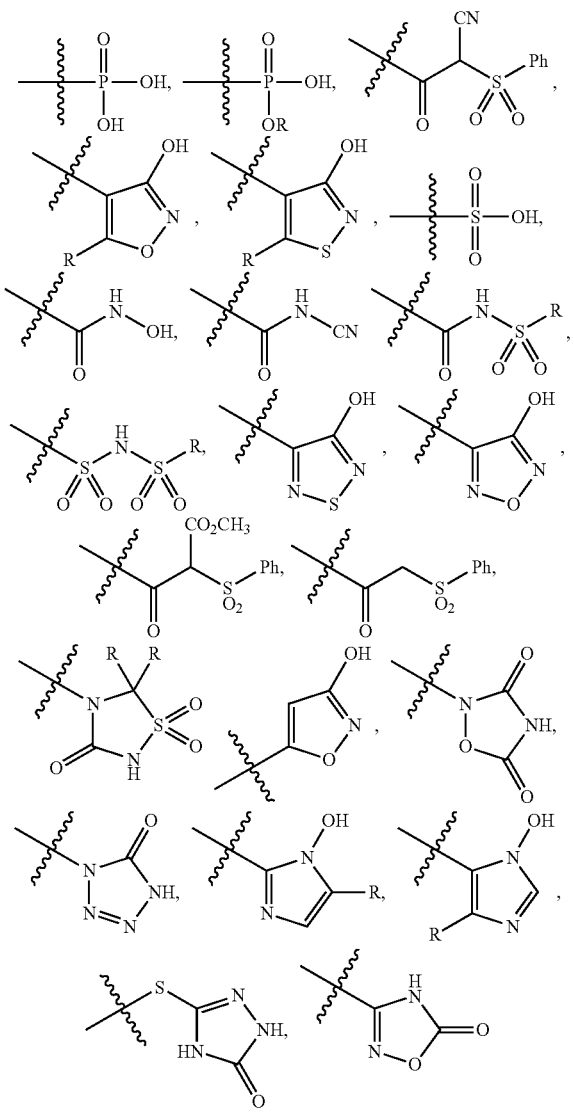

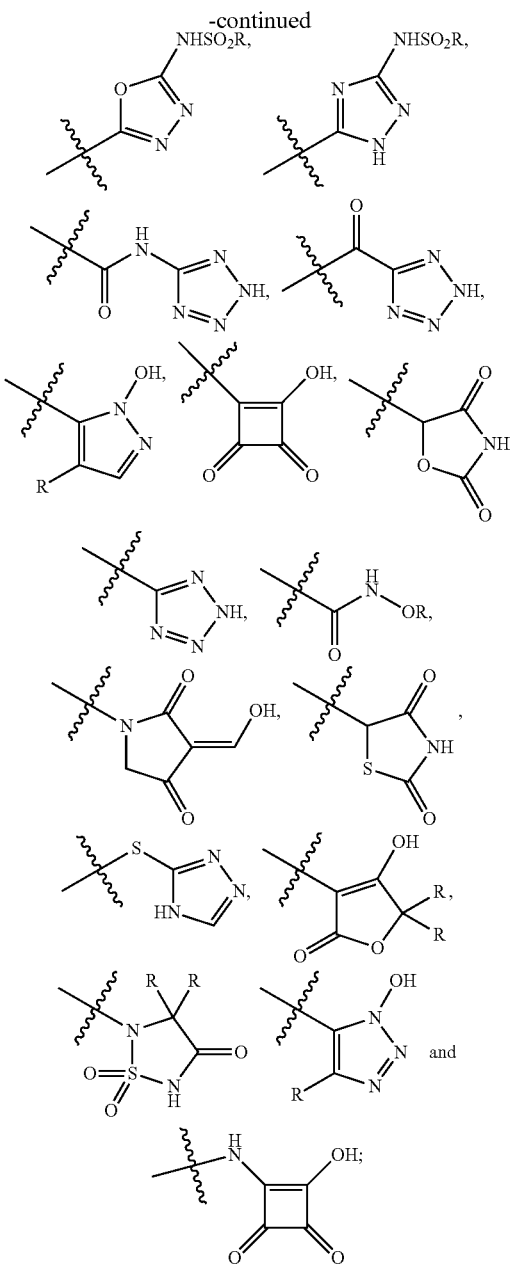

wherein R is hydrogen or $(C_1-C_3)$alkyl.

Within the context of the present application and as used herein, the term "subject" refers to an animal, preferably a mammal, and most preferably a human. The term "mammal" used herein refers to warm-blooded vertebrate animals of the class 'mammalia', including humans, characterized by a covering of hair on the skin and, in the female, milk-producing mammary glands for nourishing the young. The term mammal includes animals such as cat, dog, rabbit, bear, fox, wolf, monkey, deer, mouse, pig and human. In the context of the present invention the phrase "a subject in need thereof" means a subject (patient) in need of the treatment for the disease or disorder that is mediated by GPR120. Alternatively, the phrase "a subject in need thereof" means a subject (patient) diagnosed having a disease or disorder that is mediated by GPR120.

Within the context of the present application and as used herein, the terms "treatment" "treat" and "therapy" refer to alleviate, slow the progression, attenuation, or as such treat the existing diseases or condition (e.g. diabetes). Treatment also includes treating, or alleviating to some extent, one or more of the symptoms of the diseases or condition.

Within the context of the present application and as used herein, the terms "prophylaxis", "prevention" or "preventing" can be used interchangeably and mean preventing the disease or disorder by causing the clinical symptoms of the conditions, diseases, disorders or syndromes to not develop or decreasing the development of the disease or disorder or preventing the further development of the disease or disorder in the subjects (the patients).

Within the context of the present application and as used herein, the term "compound(s) for use" embrace any one or more of the following: (1) use of compound(s), (2) method of use of compound(s), (3) use in the treatment of, (4) the use for the manufacture of pharmaceutical composition/medicament for treatment/treating, or (5) method of treatment/treating/preventing/reducing/inhibiting comprising administering an effective amount of the compound of the present invention to a subject in need thereof.

Within the context of the present application and as used herein, the term, "therapeutically effective amount" means an amount of a compound of Formula (I) or a pharmaceutically acceptable salt thereof or a composition comprising a compound of Formula (I) or a pharmaceutically acceptable salt thereof, effective in producing the desired therapeutic response in a particular patient (subject) suffering from a disease or disorder mediated by GPR120. An example of a disease or disorder mediated by GPR120 is diabetes such as type 2 diabetes. Particularly, the term "therapeutically effective amount" includes the amount of a compound (in the context of the present invention, the compound of Formula (I) or a pharmaceutically acceptable salt thereof), when administered that induces a positive modification in the disease or disorder to be treated or is sufficient to prevent development of, or alleviate to some extent one or more of the symptoms of the disease or disorder being treated in a subject. In respect of the therapeutic amount of the compound, consideration is also given that the amount of the compound used for the treatment of a subject is low enough to avoid undue or severe side effects, within the scope of sound medical judgment. The therapeutically effective amount of the compound or composition will vary with the particular condition (in the context of the present invention, the disease or disorder that is mediated by GPR120) being treated, the age and physical condition of the subject, the severity of the condition being treated or prevented, the duration of the treatment, the nature of concurrent therapy, the specific compound or composition employed, the particular pharmaceutically acceptable carrier utilized and other related factors.

Within the context of the present application and as used herein, the term "agonist" refers to a compound that binds to a receptor and triggers a response in a cell. An agonist mimics the effect of an endogenous ligand, a hormone for example, and produces a physiological response similar to that produced by the endogenous ligand.

Within the context of the present application and as used herein, the term "GPR120 agonist(s)" refer to the compound (s) of Formula (I) of the present invention or a tautomer, a stereoisomer or a geometrical isomer thereof; or a pharmaceutically acceptable salt, a pharmaceutically acceptable solvate, a prodrug, a polymorph, an N-oxide, a S-oxide or a carboxylic acid isostere thereof; which binds to, activates, increases, stimulates, potentiates, sensitizes or upregulates GPR120 receptor and promotes glucose induced insulin secretion.

EMBODIMENTS

The invention encompasses all the compounds described by the Formula (I) without limitation, however, for the purposes of further illustrations, preferred aspects and elements of the invention are discussed herein in the form of the following embodiments.

In an embodiment, the present invention relates to a compound of Formula (I);
wherein:
Ring A is 5- to 12-membered carbocycle which is unsubstituted or substituted with one or more groups of $R^1$; wherein $R^1$ is as defined above;
or a tautomer, a stereoisomer, a geometrical isomer, a pharmaceutically acceptable salt, a pharmaceutically acceptable solvate, a prodrug, a polymorph, an N-oxide, a S-oxide or a carboxylic acid isostere thereof.

In an embodiment, the present invention relates to a compound of Formula (I)
wherein:
Ring A is 5- to 12-membered heterocyclyl containing 1, 2, 3 or 4 heteroatoms independently selected from the group consisting of N, O and S, wherein said heterocyclyl is unsubstituted or substituted with one or more groups of $R^1$, wherein $R^1$ is as defined above;
or a tautomer, a stereoisomer, a geometrical isomer, a pharmaceutically acceptable salt, a pharmaceutically acceptable solvate, a prodrug, a polymorph, an N-oxide, a S-oxide or a carboxylic acid isostere thereof.

In an embodiment, the present invention relates to a compound of Formula (I);
wherein:
Ring A is $(C_6-C_{10})$aryl; which is unsubstituted or substituted with one or more groups of $R^1$; wherein $R^1$ is as defined above;
or a tautomer, a stereoisomer, a geometrical isomer, a pharmaceutically acceptable salt, a pharmaceutically acceptable solvate, a prodrug, a polymorph, an N-oxide, a S-oxide or a carboxylic acid isostere thereof.

In another embodiment, the present invention relates to a compound of Formula (I);
wherein:
Ring A is 5- to 12-membered heteroaryl containing 1, 2, 3 or 4 heteroatoms independently selected from the group consisting of N, O and S, wherein said heteroaryl is unsubstituted or which is substituted with one or more groups of $R^1$; wherein $R^1$ is as defined above;
or a tautomer, a stereoisomer, a geometrical isomer, a pharmaceutically acceptable salt, a pharmaceutically acceptable solvate, a prodrug, a polymorph, an N-oxide, a S-oxide or a carboxylic acid isostere thereof.

In yet another embodiment, the present invention relates to a compound of Formula (I); wherein:
Ring B is saturated or partially unsaturated 5- to 12-membered carbocycle, which is unsubstituted or substituted with one or more groups of $R^2$; wherein $R^2$ is as defined above;
or a tautomer, a stereoisomer, a geometrical isomer, a pharmaceutically acceptable salt, a pharmaceutically acceptable solvate, a prodrug, a polymorph, an N-oxide, a S-oxide or a carboxylic acid isostere thereof.

In yet another embodiment, the present invention relates to a compound of Formula (I); wherein:

Ring B is saturated or partially unsaturated 5- to 12-membered heterocyclyl containing 1, 2, 3 or 4 heteroatoms independently selected from the group consisting of N, O and S, wherein said heterocyclyl is unsubstituted or substituted with one or more groups of $R^2$; wherein $R^2$ is as defined above;
or a tautomer, a stereoisomer, a geometrical isomer, a pharmaceutically acceptable salt, a pharmaceutically acceptable solvate, a prodrug, a polymorph, an N-oxide, a S-oxide or a carboxylic acid isostere thereof.

In another embodiment, the present invention relates to a compound of Formula (I); wherein:
Ring C is $(C_6-C_{10})$aryl which is unsubstituted or substituted with one or more groups of $R^3$; wherein $R^3$ is as defined above;
or a tautomer, a stereoisomer, a geometrical isomer, a pharmaceutically acceptable salt, a pharmaceutically acceptable solvate, a prodrug, a polymorph, an N-oxide, a S-oxide or a carboxylic acid isostere thereof.

In another embodiment, the present invention relates to a compound of Formula (I); wherein:
Ring C is 5- to 12-membered heteroaryl which is unsubstituted or substituted with one or more groups of $R^3$; wherein $R^3$ is as defined above;
or a tautomer, a stereoisomer, a geometrical isomer, a pharmaceutically acceptable salt, a pharmaceutically acceptable solvate, a prodrug, a polymorph, an N-oxide, a S-oxide or a carboxylic acid isostere thereof.

In another embodiment, the present invention relates to a compound of Formula (I), wherein W represents a bond.

In another embodiment, the present invention relates to a compound of Formula (I), wherein W is —$(CR^5R^6)_p$— and $R^5$, $R^6$ and p are as defined above.

In another embodiment, the present invention relates to a compound of Formula (I), wherein W is —O—.

In another embodiment, the present invention relates to a compound of Formula (I), wherein X is —$CR^5R^6$—O—, and $R^5$ and $R^6$ are as defined above.

In another embodiment, the present invention encompasses a compound of Formula (I), wherein Y is —$(C(R^4)_2)_q$—; q is 1, 2, 3 or 4 and $R^4$ is as defined above.

In another embodiment, the present invention relates to a compound of Formula (I), wherein Y is —$(C(R^4)_2)_q$—; q is 3 or 4 and $R^4$ is as defined above.

In another embodiment, the present invention relates to a compound of Formula (I), wherein Y is —$(C(R^4)_2)_q$—; q is 3 and $R^4$ at each occurrence is independently selected from hydrogen or $(C_1-C_6)$alkyl.

In another embodiment, the present invention relates to a compound of Formula (I), wherein Q is —$CO_2M$ and M is hydrogen or $(C_1-C_6)$alkyl.

According to an embodiment of the present invention, the compound of Formula (I) relates to a compound of Formula (Ia);

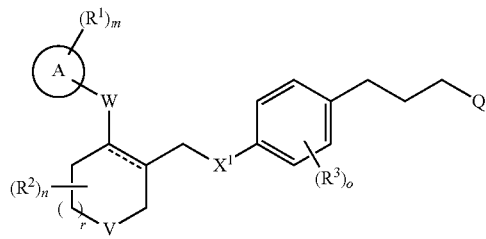

Formula Ia or a tautomer, a stereoisomer, a geometrical isomer, a pharmaceutically acceptable salt, a pharmaceutically acceptable solvate, a prodrug, a polymorph, an N-oxide, a S-oxide or a carboxylic acid isostere thereof:

wherein:

Ring A is 5- to 12-membered carbocycle, 5- to 12-membered heterocyclyl, $(C_6-C_{10})$aryl or 5- to 12-membered heteroaryl;

W represents a bond, —O—, —S— or —NR$^7$—;

$X^1$ is —O—, —S—, or —NR$^7$—,

V is —CR$^5$R$^6$—, —O—, —S— or —NR$^7$—;

Q is —CO$_2$M, —CONH$_2$, —CONH[$(C_1-C_6)$alkyl], —CON[$(C_1-C_6)$alkyl]$_2$, —CONHSO$_2(C_1-C_6)$alkyl or a carboxylic acid isostere;

M is hydrogen, deuterium or $(C_1-C_6)$alkyl;

------ represents a single bond or a double bond;

wherein, ------

$R^1$ at each occurrence is independently selected from the group consisting of hydrogen, halogen, $(C_1-C_6)$alkyl, $(C_1-C_6)$alkenyl, halo$(C_1-C_6)$alkyl, $(C_1-C_6)$alkoxy, hydroxy, $(C_3-C_{10})$cycloalkyl, heterocyclyl, $(C_6-C_{10})$aryl, heteroaryl, $(C_6-C_{10})$aryloxy, cyano, oxo, —NR$^7$R$^8$, —C(O)NR$^7$R$^8$, —C(S)NR$^7$R$^8$, —S(O)$_r$R$^9$ and —C(O)R$^{10}$;

$R^2$ at each occurrence is independently selected from the group consisting of hydrogen, halogen, $(C_1-C_6)$alkyl, $(C_1-C_6)$alkenyl, halo$(C_1-C_6)$alkyl, $(C_1-C_6)$alkoxy, hydroxy, $(C_3-C_{10})$cycloalkyl, heterocyclyl, $(C_6-C_{10})$aryl, heteroaryl, $(C_6-C_{10})$aryloxy, cyano, oxo, —NR$^7$R$^8$, —C(O)NR$^7$R$^8$, —C(S)NR$^7$R$^8$, —S(O)$_r$R$^9$ and —C(O)R$^{10}$;

$R^3$ at each occurrence is independently selected from the group consisting of hydrogen, halogen, $(C_1-C_6)$alkyl, $(C_1-C_6)$alkoxy, hydroxy, $(C_3-C_{10})$cycloalkyl, heterocyclyl, $(C_6-C_{10})$aryl, heteroaryl, cyano, —NR$^7$R$^8$, —S(O)$_r$R$^9$ and —C(O)R$^{10}$ $R^5$ and $R^6$ are independently selected from the group consisting of hydrogen, deuterium, $(C_1-C_6)$alkyl, halo$(C_1-C_6)$alkyl and halogen; or $R^5$ and $R^6$ together with the carbon atom to which they are attached can combine to form
  i) 5- to 12-membered carbocycle or
  ii) 5- to 12-membered heterocyclyl containing 1, 2, 3 or 4 heteroatoms independently selected from the group consisting of N, O and S;

$R^7$ and $R^8$ are independently selected from the group consisting of hydrogen, hydroxy, $(C_1-C_6)$alkyl, $(C_1-C_6)$alkenyl, halo$(C_1-C_6)$alkyl, $(C_1-C_6)$alkoxy, $(C_3-C_{10})$cycloalkyl, heterocyclyl, $(C_6-C_{10})$aryl, heteroaryl, $(C_6-C_{10})$aryloxy, —S(O)$_r$R$^9$; or $R^7$ and $R^8$, together with the nitrogen atom to which they are attached combine to form heterocyclyl;

$R^9$ and $R^{10}$ are independently selected from the group consisting of hydrogen, hydroxy, $(C_1-C_6)$alkyl, halo$(C_1-C_6)$alkyl, $(C_1-C_6)$alkoxy, $(C_3-C_{10})$cycloalkyl, heterocyclyl, $(C_6-C_{10})$aryl, heteroaryl and —NR$^7$R$^8$;

m is 0, 1, 2 or 3;

n is 0, 1, 2 or 3;

o is 0, 1 or 2;

r is 0, 1, 2, 3 or 7;

t is 0, 1 or 2;

wherein:

$(C_1-C_6)$alkyl is unsubstituted or substituted with one or more groups independently selected from the group consisting of $(C_1-C_6)$alkyl, $(C_1-C_6)$alkenyl, halogen, halo$(C_1-C_6)$alkyl, hydroxy, $(C_1-C_6)$alkoxy, halo$(C_1-C_6)$alkoxy, $(C_3-C_{10})$cycloalkyl, $(C_6-C_{10})$aryl, $(C_6-C_{10})$aryloxy, heterocyclyl, heteroaryl, amino, cyano, nitro, —NH$(C_1-C_6)$alkyl, —N[$(C_1-C_6)$alkyl]$_2$, —C(O)$(C_1-C_6)$alkyl, —C(O)O$(C_1-C_6)$alkyl, —C(O)NH$_2$, —C(O)NH$(C_1-C_6)$alkyl, —C(O)N[$(C_1-C_6)$alkyl]$_2$ and —C(O)NHSO$_2(C_1-C_6)$alkyl;

$(C_3-C_{10})$cycloalkyl is unsubstituted or substituted with one or more groups independently selected from the group consisting of $(C_1-C_6)$alkyl, $(C_1-C_6)$alkenyl, halogen, halo$(C_1-C_6)$alkyl, hydroxy, $(C_1-C_6)$alkoxy, halo$(C_1-C_6)$alkoxy, amino, cyano and nitro;

carbocycle is a 5- to 12-membered ring which is unsubstituted or substituted with one or more groups independently selected from the group consisting of $(C_1-C_6)$alkyl, $(C_1-C_6)$alkenyl, halo$(C_1-C_6)$alkyl, hydroxy, halogen, $(C_1-C_6)$alkoxy, halo$(C_1-C_6)$alkoxy, $(C_6-C_{10})$aryl, $(C_3-C_{10})$cycloalkyl, heteroaryl, heterocyclyl, amino, cyano, nitro, —C(O)O$(C_1-C_6)$alkyl, —C(O)NR$^7$R$^8$ and —S(O)$_t$R$^9$; wherein R$^7$, R$^8$, R$^9$ and t are as defined above;

heterocyclyl is a 5- to 12-membered ring which is unsubstituted or substituted with one or more groups independently selected from the group consisting of $(C_1-C_6)$alkyl, $(C_1-C_6)$alkenyl, halogen, halo$(C_1-C_6)$alkyl, hydroxy, $(C_1-C_6)$alkoxy, halo$(C_1-C_6)$alkoxy, $(C_3-C_{10})$cycloalkyl, $(C_6-C_{10})$aryl, heterocyclyl, heteroaryl, amino, cyano, nitro, oxo, —NR$^7$R$^8$, —C(O)NR$^7$R$^8$, —S(O)$_t$R$^9$ and —C(O)R$^{10}$; wherein R$^7$, R$^8$, R$^9$, R$^{10}$ and t are as defined above;

$(C_6-C_{10})$aryl is unsubstituted or substituted with one or more groups independently selected from the group consisting of $(C_1-C_6)$alkyl, $(C_1-C_6)$alkenyl, halogen, halo$(C_1-C_6)$alkyl, hydroxy, $(C_1-C_6)$alkoxy, halo$(C_1-C_6)$alkoxy, $(C_3-C_{10})$cycloalkyl, $(C_6-C_{10})$aryl, heterocyclyl, heteroaryl, amino, cyano, nitro, —C(O)O$(C_1-C_6)$alkyl, —C(O)NR$^7$R$^8$ and —S(O)$_t$R$^9$; wherein R$^7$, R$^8$, R$^9$ and t are as defined above;

heteroaryl is a 5- to 12-membered ring which is unsubstituted or substituted with one or more groups independently selected from the group consisting of $(C_1-C_6)$alkyl, $(C_1-C_6)$alkenyl, halogen, halo$(C_1-C_6)$alkyl, hydroxy, $(C_1-C_6)$alkoxy, halo$(C_1-C_6)$alkoxy, $(C_3-C_{10})$cycloalkyl, $(C_6-C_{10})$aryl, heterocyclyl, heteroaryl, amino, cyano, nitro, —C(O)NR$^7$R$^8$ and —S(O)$_t$R$^9$; wherein R$^7$, R$^8$, R$^9$ and t are as defined above.

In an embodiment, the compound of Formula (I) encompasses the compound of Formula (Ia), wherein Ring A is $(C_6-C_{10})$aryl or 5- to 12-membered heteroaryl, wherein said aryl and heteroaryl is unsubstituted or substituted with one or more groups of $R^1$, wherein $R^1$ is as defined above.

In another embodiment, the compound of Formula (I) encompasses the compound of Formula (Ia), wherein W represents a bond.

In another embodiment, the compound of Formula (I) encompasses the compound of Formula (Ia), wherein W is —O—.

In another embodiment, the compound of Formula (I) encompasses the compound of Formula (Ia), wherein W is —S—.

In another embodiment, the compound of Formula (I) encompasses the compound of Formula (Ia), wherein W is —NR$^7$—, wherein R$^7$ is as defined above.

In another embodiment, the compound of Formula (I) encompasses the compound of Formula (Ia), wherein $X^1$ is —O—.

In another embodiment, the compound of Formula (I) encompasses the compound of Formula (Ia), wherein V is —CR$^5$R$^6$—, wherein R$^5$ and R$^6$ is as defined above.

In another embodiment, the compound of Formula (I) encompasses the compound of Formula (Ia), wherein V is —O—.

In another embodiment, the compound of Formula (I) encompasses the compound of Formula (Ia), wherein V is —S—.

In another embodiment, the compound of Formula (I) encompasses the compound of Formula (Ia), wherein V is —NR$^7$—, wherein R$^7$ is as defined above.

In another embodiment, the compound of Formula (I) encompasses the compound of Formula (Ia), wherein r is 0.

In another embodiment, the compound of Formula (I) encompasses the compound of Formula (Ia), wherein r is 1.

In another embodiment, the compound of Formula (I) encompasses the compound of Formula (Ia), wherein r is 2.

In another embodiment, the compound of Formula (I) encompasses the compound of Formula (Ia), wherein r is 3.

In another embodiment, the compound of Formula (I) encompasses the compound of Formula (Ia), wherein r is 7.

In an embodiment, the compound of Formula (I) encompasses the compound of Formula (Ia), wherein Ring A is (C$_6$-C$_{10}$)aryl, which is unsubstituted or substituted with one or more groups of R$^1$, wherein R$^1$ is as defined above;
W represents a bond or O;
V is —CR$^5$R$^6$—, wherein R$^5$ and R$^6$ are as defined above;
r is 0, 1, 2, 3 or 7;
X$^1$ is O;
Q is —COOH;
or a tautomer, a stereoisomer, a geometrical isomer, a pharmaceutically acceptable salt, a pharmaceutically acceptable solvate, a prodrug, a polymorph, an N-oxide, a S-oxide or a carboxylic acid isostere thereof.

In an embodiment, the compound of Formula (I) encompasses the compound of Formula (Ia), wherein Ring A is 5- to 12-membered heteroaryl which is unsubstituted or substituted with one or more groups of R$^1$, wherein R$^1$ is as defined above;
W represents a bond or O;
V is —CR$^5$R$^6$—, wherein R$^5$ and R$^6$ are as defined above;
r is 0, 1, 2, 3 or 7;
X$^1$ is O and
Q is —COOH;
or a tautomer, a stereoisomer, a geometrical isomer, a pharmaceutically acceptable salt, a pharmaceutically acceptable solvate, a prodrug, a polymorph, an N-oxide, a S-oxide or a carboxylic acid isostere thereof.

Representative compounds of Formula (I) of the present invention include:
4-(4-((4'-(1-cyanocyclopropyl)-3,4,5,6-tetrahydro-[1,1'-biphenyl]-2-yl)methoxy)phenyl) butanoic acid;
4-(4-((2-(5,6,7,8-tetrahydroquinolin-3-yl)cyclohex-1-en-1-yl)methoxy)phenyl)butanoic acid;
4-(4-((2-(2,3-dihydro-1H-inden-5-yl)cyclohex-1-en-1-yl)methoxy)phenyl)butanoic acid;
4-(4-((2-(4,5,6,7-tetrahydrobenzo[d]thiazol-2-yl)cyclohex-1-en-1-yl)methoxy)phenyl) butanoic acid;
4-(4-((4'-cyano-3,4,5,6-tetrahydro-[1,1'-biphenyl]-2-yl)methoxy)phenyl)butanoic acid;
4-(4-((4'-methoxy-3,4,5,6-tetrahydro-[1,1'-biphenyl]-2-yl)methoxy)phenyl)butanoic acid;
4-(4-((4'-cyclopropyl-3,4,5,6-tetrahydro-[1,1'-biphenyl]-2-yl)methoxy)phenyl)butanoic acid;
4-(4-((2-(6-amino-5-(trifluoromethyl)pyridin-3-yl)cyclohex-1-en-1-yl)methoxy)phenyl) butanoic acid;
4-(4-((2-(5,6,7,8-tetrahydronaphthalen-2-yl)cyclohex-1-en-1-yl)methoxy)phenyl)butanoic acid;
4-(4-([1,1'-bi(cyclohexane)]-1,1'-dien-2-ylmethoxy)phenyl) butanoic acid;
4-(4-((3'-methyl-3,4,5,6-tetrahydro-[1,1'-biphenyl]-2-yl)methoxy)phenyl)butanoic acid;
4-(4-((3,4,5,6-tetrahydro-[1,1'-biphenyl]-2-yl)methoxy)phenyl)butanoic acid;
4-(4-((2'-methyl-3,4,5,6-tetrahydro-[1,1'-biphenyl]-2-yl)methoxy)phenyl)butanoic acid;
4-(4-((2-(6-methoxypyridin-3-yl)cyclohex-1-en-1-yl)methoxy)phenyl)butanoic acid;
4-(4-((4'-methyl-3,4,5,6-tetrahydro-[1,1'-biphenyl]-2-yl)methoxy)phenyl)butanoic acid;
4-(4-((2-(p-tolyl)cyclooct-1-en-1-yl)methoxy)phenyl)butanoic acid;
4-(4-((2-(m-tolyl)cyclooct-1-en-1-yl)methoxy)phenyl)butanoic acid;
4-(4-((2-(o-tolyl)cyclooct-1-en-1-yl)methoxy)phenyl)butanoic acid;
4-(4-((2-phenylcyclooct-1-en-1-yl)methoxy)phenyl)butanoic acid;
4-(4-((2-(4-cyclopropylphenyl)cyclooct-1-en-1-yl)methoxy)phenyl)butanoic acid;
4-(4-((2-(4-(1-cyanocyclopropyl)phenyl)cyclohept-1-en-1-yl)methoxy)phenyl)butanoic acid;
4-(4-((2-(p-tolyl)cyclohept-1-en-1-yl)methoxy)phenyl)butanoic acid;
4-(4-((2-(4-cyclopropylphenyl)cyclododec-1-en-1-yl)methoxy)phenyl)butanoic acid;
4-(4-((2-(o-tolyl)cyclopent-1-en-1-yl)methoxy)phenyl)butanoic acid;
4-(4-((2-phenylcyclopent-1-en-1-yl)methoxy)phenyl)butanoic acid;
4-(4-((2-(4-cyclopropylphenyl)cyclopent-1-en-1-yl)methoxy)phenyl)butanoic acid;
4-(4-((2-(4-cyclopropylphenyl)cyclohept-1-en-1-yl)methoxy)phenyl)butanoic acid;
4-(4-((2-(m-tolyl)cyclohept-1-en-1-yl)methoxy)phenyl)butanoic acid;
4-(4-((2-(o-tolyl)cyclohept-1-en-1-yl)methoxy)phenyl)butanoic acid;
4-(4-((2-phenylcyclododec-1-en-1-yl)methoxy)phenyl)butanoic acid;
4-(4-((2-(p-tolyl)cyclododec-1-en-1-yl)methoxy)phenyl)butanoic acid;
4-(4-((2-(2,3-dihydrobenzofuran-5-yl)cyclohept-1-en-1-yl)methoxy)phenyl)butanoic acid;
4-(4-((2-(2,3-dihydrobenzofuran-5-yl)cyclohex-1-en-1-yl)methoxy)phenyl)butanoic acid;
4-(4-((2-(2,3-dihydrobenzofuran-5-yl)cyclopent-1-en-1-yl)methoxy)phenyl)butanoic acid;
4-(4-((2-(p-tolyl)cyclopent-1-en-1-yl)methoxy)phenyl)butanoic acid;
4-(4-((2-(m-tolyl)cyclopent-1-en-1-yl)methoxy)phenyl)butanoic acid;
4-(4-((2-(5-methylthiophen-2-yl)cyclohept-1-en-1-yl)methoxy)phenyl)butanoic acid;
4-(4-((2-(pyridin-3-yl)cyclohept-1-en-1-yl)methoxy)phenyl)butanoic acid;
4-(4-((2-(4-methoxyphenyl)cyclohept-1-en-1-yl)methoxy)phenyl)butanoic acid;
4-(4-((2-(6-methoxypyridin-3-yl)cyclohept-1-en-1-yl)methoxy)phenyl)butanoic acid;
4-(4-((2-(bicyclo[4.2.0]octa-1(6),2,4-trien-3-yl)cyclohept-1-en-1-yl)methoxy)phenyl) butanoic acid;
4-(4-((2-(2-methylbenzo[d]thiazol-5-yl)cyclohept-1-en-1-yl)methoxy)phenyl)butanoic acid;
4-(4-((4-(p-tolyl)-5,6-dihydro-2H-pyran-3-yl)methoxy)phenyl)butanoic acid;
4-(4-((4-(4-(1-cyanocyclopropyl)phenyl)-5,6-dihydro-2H-pyran-3-yl)methoxy)phenyl) butanoic acid;

4-(4-((4-(5,6,7,8-tetrahydronaphthalen-2-yl)-5,6-dihydro-2H-pyran-3-yl)methoxy)phenyl) butanoic acid;
4-(4-((2-(p-tolyloxy)cyclohex-1-en-1-yl)methoxy)phenyl) butanoic acid;
4-(4-((2-cyclohex-1-en-1-yl)methoxy)phenyl)butanoic acid;
4-(4-((2-(p-tolyloxy)cyclohept-1-en-1-yl)methoxy)phenyl) butanoic acid;
4-(4-((4'-(1-cyanocyclopropyl)-4-methyl-3,4,5,6-tetrahydro-[1,1'-biphenyl]-2-yl)methoxy) phenyl)butanoic acid;
4-(4-((4-fluoro-4'-methyl-3,4,5,6-tetrahydro-[1,1'-biphenyl]-2-yl)methoxy)phenyl)butanoic acid;
ethyl 4-(5-((4-(6-methoxypyridin-3-yl)-5,6-dihydro-2H-pyran-3-yl)methoxy)pyridin-2-yl)butanoic acid;
4-(4-((2-(p-tolyl)cyclohept-1-en-1-yl)methoxy)phenyl)butanoate metformin salt;
4-(4-((2-(p-tolyl)cyclohept-1-en-1-yl)methoxy)phenyl)butanoate, piperazine-1,4-diium salt;
4-(4-((2-(p-tolyl)cyclohept-1-en-1-yl)methoxy)phenyl)butanoate, 2-hydroxyethanaminium salt;
4-(4-((2-(p-tolyl)cyclohept-1-en-1-yl)methoxy)phenyl)butanoate, sodium salt;
4-(4-((2-phenoxycyclohex-1-en-1-yl)methoxy)phenyl)butanoic acid;
4-(4-((4-(4-Cyanophenyl)-5,6-dihydro-2H-pyran-3-yl) methoxy)phenyl)butanoic acid;
4-(4-((4-(6-methoxypyridin-3-yl)-5,6-dihydro-2H-pyran-3-yl)methoxy) phenyl) butanoic acid;
4-(4-((4-(2-methoxypyrimidin-5-yl)-5,6-dihydro-2H-pyran-3-yl)methoxy) phenyl)butanoic acid;
4-(4-((4-(2-methoxypyrimidin-5-yl)-5,6-dihydro-2H-pyran-3-yl)methoxy) phenyl)butanoic acid;
4-(4-((4-(4-morpholinophenyl)-5,6-dihydro-2H-pyran-3-yl) methoxy) phenyl) butanoic acid;
4-(4-((4-(5-methylthiophen-2-yl)-5,6-dihydro-2H-pyran-3-yl)methoxy)phenyl) butanoic acid;
Sodium 4-(4-((4-(p-tolyl)-5,6-dihydro-2H-pyran-3-yl) methoxy)phenyl) butanoate;
Calcium salt of 4-(4-((4-(p-tolyl)-5,6-dihydro-2H-pyran-3-yl)methoxy)phenyl) butanoic acid;
Piperazine salt of 4-(4-((4-(p-tolyl)-5,6-dihydro-2H-pyran-3-yl)methoxy) phenyl) butanoic acid;
Metformin salt of 4-(4-((4-(p-tolyl)-5,6-dihydro-2H-pyran-3-yl)methoxy) phenyl) butanoic acid;
3-(4-((2-(5,6,7,8-tetrahydronaphthalen-2-yl)cyclohept-1-en-1-yl)methoxy) phenyl)propanoic acid;
3-(4-((2-(p-tolyl)cyclohept-1-en-1-yl)methoxy)phenyl)propanoic acid;
3-(4-((2-(4-cyclopropylphenyl)cyclohept-1-en-1-yl) methoxy)phenyl)propanoic acid;
3-(4-((2-(4-(1-cyanocyclopropyl)phenyl)cyclohept-1-en-1-yl)methoxy)phenyl) propanoic acid;

4-(5-((4'-methyl-3,4,5,6-tetrahydro-[1,1'-biphenyl]-2-yl)methoxy)pyridin-2-yl)butanoic acid;
4-(5-((3,4,5,6-tetrahydro-[1,1'-biphenyl]-2-yl)methoxy) pyridin-2-yl)butanoic acid;
or a stereoisomer, a tautomer, a geometrical isomer, a pharmaceutically acceptable salt or a pharmaceutically acceptable solvate thereof.

The compounds of the present invention include all stereoisomeric and tautomeric forms and mixtures thereof in all ratios and their pharmaceutically acceptable salts, solvates, prodrugs, polymorphs N-oxides, S-oxides and carboxylic acid isosteres.

According to another aspect of the present invention, there are provided processes for the preparation of the compounds of Formula (I) or pharmaceutically acceptable salts thereof.

Thus, the compounds of Formula (I) can be prepared by various methods including using methods well known to a person skilled in the art. Examples of processes for the preparation of a compound of Formula I are described below and illustrated in the following schemes but are not limited thereto. It will be appreciated by persons skilled in the art that within certain of the processes described herein, the order of the synthetic steps employed can be varied and will depend inter alia on factors such as the nature of functional groups present in a particular substrate and the protecting group strategy (if any) to be adopted. Clearly, such factors will also influence the choice of reagent such as bases, solvents, coupling agents to be used in the reaction steps.

The reagents, reactants and intermediates used in the following processes are either commercially available or can be prepared according to standard procedures known in the art, for instance those reported in the literature references.

In the following scheme and the description of general procedures for the preparation of the compounds of Formula (I), for ease of reference the starting compounds and the intermediates used for the synthesis of the compounds of the present invention, are designated as compounds 1a, 1b, 1, 2, 3, 4, 5a, 5b, 6 and 7 respectively. In the following scheme general procedure followed for the synthesis of the compounds of Formula (I) are referred to as procedure A, B, C, D and E respectively, for ease of reference.

Thus, the general procedure followed for the preparation of the compounds of Formula (I) is depicted in the following Scheme-1.

Procedure for Preparation of the Compound(s) 1a, 1b and 1:

The compounds represented as compound 1a, compound 1b and compound 1, are prepared according to the procedure described in European Journal of Organic Chemistry, 2007, (20), 3277-3280; Tetrahedron Letters, 1988, (29), 5789-5792 and Applied Organometallic Chemistry, 2012, (26), 499-503.

Scheme 1

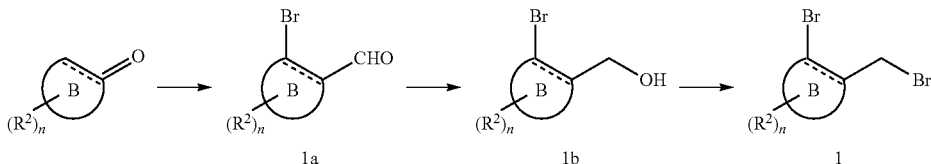

-continued
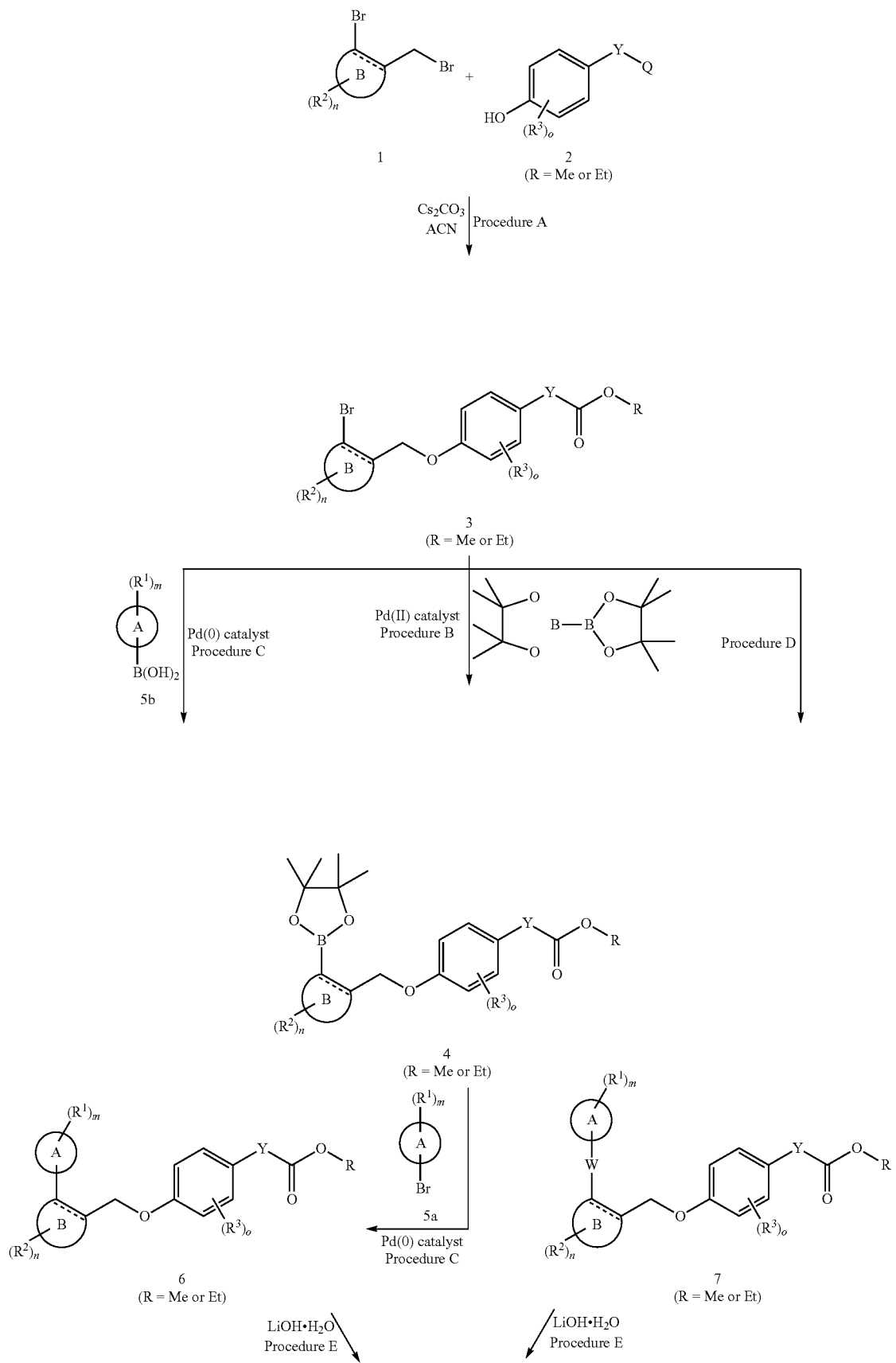

-continued

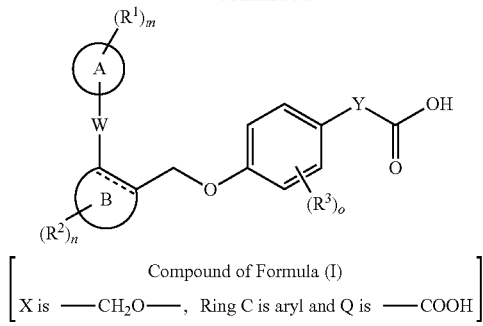

[Compound of Formula (I)
X is —CH₂O—, Ring C is aryl and Q is —COOH]

Procedure A:

A mixture of compound 1 (wherein ring B, R² and n are as defined herein) and cesium carbonate in dry acetonitrile (ACN) is stirred at room temperature followed by addition of a compound 2 (wherein ring C, R³, o and Y are as defined herein). The reaction mixture is stirred overnight at room temperature. After the completion of reaction, the reaction mixture is diluted with ethyl acetate and filtered. The filtrate obtained is concentrated and purified by column chromatography using ethyl acetate/petroleum ether as eluent to obtain compound 3 (wherein ring B, ring C, R², R³, n, o and Y are as defined above).

Procedure B:

A mixture of the compound 3 as obtained from general procedure A, bispinacolato diborane and a dry solvent such as 1,4-dioxane is taken in a round bottom flask, the flask is purged with dry argon for 5 minutes followed by addition of potassium acetate and [1,1'-bis(diphenylphosphino)ferrocene]dichloropalladium(II), complex with dichloromethane ((PdCl₂(dppf))CH₂Cl₂). The resulting reaction mixture is heated to 80° C. for 8-10 hours. After completion of the reaction, the solvent is removed from the mixture under vacuum. The material obtained is purified by column chromatography using ethyl acetate/petroleum ether as eluent, to obtain compound 4 (wherein ring B, ring C, R², R³, n, o and Y are as defined above).

Procedure C

Compound 5a (wherein ring A, R¹ and m are as defined), the compound 4 obtained as described in Procedure B, a mixture of solvents such as 1,4-dioxane and water are taken in a round bottom flask. Sodium bicarbonate is added to the flask and the flask is purged with argon for 5 minutes, followed by addition of tetrakis(triphenylphosphine)palladium(0). The flask is purged with argon for 5 minutes and the reaction mixture is heated at temperature in the range of 80° C. to 120° C. for 5-6 hours. The reaction mixture is concentrated under vacuum and diluted with water followed by extraction with an organic solvent such as ethyl acetate, dried over sodium sulphate and is concentrated. The material obtained is purified by column chromatography using ethyl acetate/petroleum ether as eluent to obtain the compound 6 (wherein ring A, ring B, ring C, R¹, R², R³, m, n, o and Y are as defined herein). Alternatively, the compound 6 is prepared from the compound 5b and the compound 3 obtained as described in Procedure A under similar reaction conditions.

Procedure D

A mixture of the compound 3 obtained as described in procedure A, a phenol compound such as p-cresol, potassium phosphate and di-tert-butyl(2',6'-diphenyl-[1,1':4',1''-terphenyl]-2-yl)phosphine in dry toluene was stirred in the presence of argon for 5 minutes. Palladium acetate was added to the mixture and flushed with argon for 5 min. The reaction mixture was heated at 80-120° C. for 5-6 hours. The reaction mixture is cooled to room temperature and concentrated. The reaction mixture is quenched using ammonium chloride solution and the mixture is extracted with an organic solvent such as ethyl acetate. The combined organic layer is dried over sodium sulphate, concentrated and purified by chromatography using ethyl acetate/pet ether as eluent to obtain compound 7 (wherein ring A, ring B, ring C, R¹, R², R³, W, m, n, o and Y are as defined above).

Procedure E

The compound 6 or compound 7 obtained as described in Procedure D is suspended in a mixture of organic solvent such as tetrahydrofuran (THF) and methanol and LiOH.H₂O (5 equivalent) solution in water (2 mL/mmol) is added to it. The resulting reaction mixture is stirred overnight at room temperature. The reaction mixture is concentrated under vacuum, acidified with saturated solution of NH₄Cl (ammonium chloride). The mixture is extracted with an organic solvent such as ethyl acetate, dried over sodium sulphate and concentrated under vacuum to obtain the compound of Formula I (wherein ring A, ring B, ring C, R¹, R², R³, W, m, n, o and Y are as defined above).

The compounds of Formula (I) can be converted into their pharmaceutically acceptable salts by following procedure known to persons skilled in the art.

The pharmaceutically acceptable salt of the compounds of Formula (I) are prepared with relatively non-toxic acids or bases, depending on the particular substituents found on the compound described herein. When the compounds of Formula (I) of the present invention contain an acidic group they can form an addition salt with a suitable base. For example, pharmaceutically acceptable base addition salts of the compounds of the present invention includes their alkali metal salts such as sodium, potassium, calcium, magnesium, ammonium or an organic base addition salt. Examples of pharmaceutically acceptable organic base addition salts of the compounds of the present invention include those derived from organic bases like lysine, arginine, guanidine, diethanolamine, metformin, piperazine or other organic bases known to the person skilled in the art.

When the compounds of Formula (I) of the present invention contain one or more basic groups, they can form an addition salt with an inorganic or an organic acid. Examples of pharmaceutically acceptable acid addition salts include those derived from inorganic acids like boric acid, perchloric acid, hydrochloric acid, hydrobromic acid, hydrofluoric acid, hydriodic acid, nitric acid, carbonic acid, monohydrogencarbonic acid, phosphoric acid, monohydrogenphosphoric acid, dihydrogenphosphoric acid, sulfuric acid, monohydrogensulfuric acid, phosphorous acid or other inorganic acids known to the person skilled in the art. Furthermore, examples of pharmaceutically acceptable acid addition salts include the salts derived from organic acids such as acetic acid, propionic acid, isobutyric acid, oxalic acid, malic acid, tartaric acid, citric acid, ascorbic acid, maleic acid, malonic acid, benzoic acid, succinic acid, suberic acid, fumaric acid, mandelic acid, phthalic acid, benzenesulfonic acid, toluenesulfonic acid, methanesulfonic acid, glucuronic acid, galacturonic acid, naphthoic acid, camphoric acid or other organic acids known to the person skilled in the art. Certain specific compounds of the present invention contain both basic and acidic functionalities that allow the compounds to be converted into either base or acid addition salts.

The pharmaceutically acceptable salts of the present invention can be synthesized from the subject compound i.e. the compound of Formula (I) which contains a basic or acidic moiety, by conventional chemical methods. Generally, the salts are prepared by contacting the free base or acid with desired salt-forming inorganic or organic acid or a base in a suitable solvent or dispersant or by anion exchange or cation exchange with other salts. Suitable solvents are, for example, ethyl acetate, ethers, alcohols, acetone, or mixtures of these solvents. Salts can also be formed when an acidic proton present in the compound of Formula (I) is either replaced by a metal ion, e.g., an alkali metal ion, an alkaline earth ion, or an aluminum ion; or coordinates with an organic base such as ethanolamine, diethanolamine, triethanolamine, trimethylamine and N-methylglucamine.

Those skilled in the art will recognize that the compounds of Formula (I) of the present invention contain asymmetric or chiral centers, and therefore exist in different stereoisomeric forms, as racemic mixtures of enantiomers, mixtures of diastereomers or enantiomerically or optically pure compounds. The term "chiral" refers to molecules which have the property of non-superimposability of the mirror image cohort, while the term "achiral" refers to molecules which are superimposable on their mirror image partner. It is intended that all stereoisomeric forms of the compounds of the invention, including but not limited to, diastereomers and enantiomers, as well as mixtures thereof such as racemic mixtures, geometric isomers form part of the present invention.

When the compounds of Formula (I) of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which can be separated, for example, by crystallization (see, CRC Handbook of Optical Resolutions via Diastereomeric Salt Formation by David Kozma (CRC Press, 2001); formation of diastereoisomeric derivatives or complexes which can be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers can be synthesized by asymmetric synthesis using optically active reagents, substrates, catalysts or solvents, or by converting one enantiomer into the other by asymmetric transformation. Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%. When a compound of Formula (I) of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair can be separated as described above. The present invention includes each diastereoisomer of such compounds and mixtures thereof.

The isotopically labeled forms of compounds of Formula (I), can be prepared by conventional techniques known to those skilled in the art or by processes analogous to those described above or in the subsequent experimental section by using a corresponding isotopically labeled reagent in place of the non-labeled reagent.

In one embodiment, the compounds of Formula (I) exists as tautomers, and it is intended to encompass all the tautomeric forms of the compounds within the scope of the present invention.

The present invention furthermore includes all the solvates of the compounds of Formula (I), for example, hydrates and the solvates formed with other solvents of crystallisation, selected from alcohols such as methanol, ethanol, 1-propanol or 2-propanol, ethers such as diethyl ether, isopropyl ether or tetrahydrofuran, esters such as methyl acetate or ethyl acetate, ketone such as acetone or their mixtures thereof. Certain compounds of the present invention can exist in unsolvated forms as well as solvated forms, including hydrated forms.

The present invention also includes polymorphs of the compounds of Formula (I) within the scope of the present invention. The polymorphs of compounds of the present invention can be prepared by standard crystallisation procedures known in the art. The crystallisation technique employed can utilize various solvents or their mixtures, temperature conditions and various modes of cooling, ranging from very fast to very slow cooling. The presence of polymorphs can be determined by IR (Infra-red) spectroscopy, solid probe NMR (Nuclear Magnetic Resonance) spectroscopy, differential scanning calorimetry, powder X-ray diffraction and the standard techniques known to the person skilled in this art.

Furthermore, the present invention also includes prodrugs of the compounds of Formula (I). The prodrugs of the compounds of the present invention are derivatives of the aforesaid compounds of the invention which upon administration to a subject in need thereof undergoes chemical conversion by metabolic or chemical processes to release the parent drug in vivo from which the prodrug is derived. The preferred prodrugs are pharmaceutically acceptable ester derivatives e.g., alkyl esters, cycloalkyl esters, alkenyl esters, benzyl esters, mono- or di-substituted alkyl esters convertible by solvolysis under physiological conditions to the parent carboxylic acid, and those conventionally used in the art.

The present invention further relates to carboxylic acid isostere(s) of the compound(s) of Formula (I).

The present invention also relates to N-oxide(s) of the compound(s) of Formula (I).

The present invention also relates to S-oxide(s) of the compound(s) of Formula (I).

In one aspect of the present invention, the compounds of Formula (I) are GPR120 agonists.

In an embodiment, the present invention relates to the compound of Formula (I) or a tautomer, a stereoisomer, a geometrical isomer thereof, a pharmaceutically acceptable salt or a pharmaceutically acceptable solvate thereof, for use in the treatment or prophylaxis of a disease or a disorder mediated by GPR120.

In another aspect, the present invention relates to a method for the treatment or prophylaxis of a disease or a disorder mediated by GPR120, comprising administering to a subject in need thereof, a therapeutically effective amount of the compound of Formula (I) or a tautomer, a stereoisomer, a geometrical isomer thereof, a pharmaceutically acceptable salt or a pharmaceutically acceptable solvate thereof.

In an embodiment, the present invention relates to use of the compound of Formula (I) or a tautomer, a stereoisomer, a geometrical isomer thereof, a pharmaceutically acceptable salt or a pharmaceutically acceptable solvate thereof, for the treatment or prophylaxis of a disease or a disorder mediated by GPR120.

According to one embodiment, the present invention relates to use of the compound of Formula (I) or a tautomer, a stereoisomer, a geometrical isomer thereof, a pharmaceutically acceptable salt or a pharmaceutically acceptable solvate thereof, in the manufacture of a medicament for the treatment or prophylaxis of a disease or a disorder mediated by GPR120.

As used herein, the term "a disease or a disorder mediated by GPR120" or "GPR120 mediated disease(s) or disorder(s)" refers to a disease or a disorder or a condition characterized by inappropriate, for example, less than or greater than normal, GPR120 activity. A GPR120-mediated disease or disorder can be completely or partially mediated by inappropriate GPR120 activity.

In an embodiment of the invention, the disease or condition mediated by GPR120 is selected from the group consisting of diabetes, obesity, hyperglycemia, glucose intolerance, insulin resistance, hyperinsulinemia, hypercholesterolemia, hypertension, hyperlipoproteinemia, hyperlipidemia, hypertriglyceridemia, dyslipidemia, metabolic syndrome, syndrome X, cardiovascular disease, atherosclerosis, kidney disease, polycystic ovary syndrome, ketoacidosis, thrombotic disorders, nephropathy, diabetic neuropathy, diabetic retinopathy, sexual dysfunction, fatty liver development, dermatopathy, dyspepsia, hypoglycemia, cancer, edema and a disorder related to glucose levels such as pancreatic beta cell regeneration.

In an embodiment of the invention, the disease or condition mediated by GPR120 is selected from the group consisting of diabetes, obesity, insulin resistance, hyperglycemia, glucose intolerance, hypercholesterolemia, hypertriglylceridemia, dyslipidemia, hyperlipoproteinemia, hyperinsulinemia, atherosclerosis, diabetic neuropathy, diabetic retinopathy, metabolic syndrome, syndrome X, hypertension and pancreatic beta cell degeneration.

In an embodiment of the invention, the disease or condition mediated by GPR120 is selected from the group consisting of diabetes, obesity, insulin resistance, hyperglycemia, glucose intolerance, metabolic syndrome, syndrome X and pancreatic beta cell degeneration.

In an embodiment of the invention, the disease or condition mediated by GPR120 is Type 2 diabetes.

In an embodiment, the disease or disorder mediated by GPR120 is a metabolic disease or disorder.

In an embodiment, the disease or disorder mediated by GPR120 is an inflammatory disease or disorder.

Accordingly, the present invention relates to a method for the treatment or prophylaxis of a metabolic disorder, comprising administering to a subject in need thereof a therapeutically amount of the compound of Formula (I) or a tautomer, a stereoisomer, a geometrical isomer thereof, a pharmaceutically acceptable salt or a pharmaceutically acceptable solvate thereof.

In an embodiment, the present invention provides use of the compound of Formula (I) or a tautomer, a stereoisomer, a geometrical isomer thereof, a pharmaceutically acceptable salt or a pharmaceutically acceptable solvate thereof, for the treatment or prophylaxis of a metabolic disorder.

According to one embodiment, the present invention relates to use of the compounds of Formula (I), pharmaceutically acceptable salts thereof in the manufacture of a medicament, for the treatment or prophylaxis of a metabolic disorder.

The term "metabolic disorder" as used herein refers a disorder relating to abnormality of metabolism. Accordingly, in the context of the present invention all the disorders relating to abnormality of metabolism are encompassed in the term "metabolic disorders".

In one embodiment, the metabolic disorder is selected from the group consisting of diabetes, obesity, cardiovascular disease, hypertension, ketoacidosis, insulin resistance, glucose intolerance, hyperglycemia, hypertriglylceridemia, polycystic ovary syndrome, hypercholesterolemia, hyperlipoproteinemia, dyslipidemia, metabolic syndrome, syndrome X, hyperlipidemia, diabetic neuropathy, diabetic retinopathy, edema and related disorders associated with abnormal plasma lipoprotein, triglycerides and pancreatic beta cell degeneration.

The term "diabetes mellitus" or "diabetes" refers to a chronic disease or condition, which occurs when the pancreas does not produce enough insulin, or when the body cannot effectively use the insulin it produces. This leads to an increased concentration of glucose in the blood (hyperglycaemia). Two major forms of diabetes are Type 1 diabetes (Insulin-dependent diabetes mellitus) and Type 2 diabetes (Non-insulin dependent diabetes mellitus (NIDDM)). Type 1 diabetes is an autoimmune condition in which the insulin-producing β-cells of the pancreas are destroyed which generally results in an absolute deficiency of insulin, the hormone that regulates glucose utilization. Type 2 diabetes often occurs in the face of normal or even elevated levels of insulin and can result from the inability of tissues to respond appropriately to insulin. Other categories of diabetes include gestational diabetes (a state of hyperglycemia which develops during pregnancy) and "other" rarer causes (genetic syndromes, acquired processes such as pancreatitis, diseases such as cystic fibrosis and exposure to certain drugs, viruses, and unknown causes). In an embodiment, diabetes refers to Type 2 diabetes.

The term "metabolic syndrome" refers to a cluster of metabolic abnormalities including abdominal obesity, insulin resistance, glucose intolerance, diabetes, hypertension and dyslipidemia. These abnormalities are known to be associated with an increased risk of vascular events.

The term "cardiovascular disease" as used herein refers to any disease of the heart or blood vessels. One or more diseases of heart encompassed in the term "cardiovascular disease" is selected from, but not limited to, angina, arrhythmia, coronary artery disease (CAD), cardiomyopathy, myocardial infarction, heart failure, hypertrophic cardiomyopathy, mitral regurgitation, mitral valve prolapse, pulmonary stenosis, etc. The blood vessel disease encompassed in the term "cardiovascular diseases", is selected from, but not limited to, for example, peripheral vascular disease, artery disease, carotid artery disease, deep vein thrombosis, venous diseases and atherosclerosis.

In an embodiment, the metabolic disorder is selected from the group consisting of diabetes, obesity, insulin resistance, hyperglycemia, glucose intolerance, hypercholesterolemia, hypertriglylceridemia, dyslipidemia, hyperlipoproteinemia, hyperinsulinemia, atherosclerosis, diabetic neuropathy, diabetic retinopathy, metabolic syndrome, syndrome X, hypertension and pancreatic beta cell degeneration.

In an embodiment, the metabolic disorder is selected from the group consisting of diabetes, obesity, insulin resistance, glucose intolerance, dyslipidemia, hyperinsulinemia, syndrome X, metabolic syndrome and pancreatic beta cell degeneration.

In an embodiment, the metabolic disorder is Type 2 diabetes.

According to an embodiment, the present invention relates to pharmaceutical compositions comprising a therapeutically effective amount of at least one compound of Formula (I) or its pharmaceutically acceptable salt, in addition to a customary pharmaceutically acceptable carrier. The present invention also relates to a process for the production of a pharmaceutical composition, which includes bringing at least one compound of Formula (I), into a suitable administration form using a pharmaceutically suitable excipient and, if appropriate, further suitable active compounds, additives or auxiliaries.

In an embodiment, the present invention relates to a pharmaceutical composition comprising the compound of Formula (I) or a pharmaceutically acceptable salt thereof and one or more pharmaceutically acceptable excipients; for use as GPR120 agonist. In another embodiment, the present invention relates to a pharmaceutical composition comprising the compound of Formula (I) or a pharmaceutically acceptable salt thereof and one or more pharmaceutically acceptable excipients; for use in the treatment or prophylaxis of a disease or a condition mediated by GPR120.

The term "pharmaceutically acceptable carrier" as used herein means a non-toxic, inert, solid, semi-solid, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose and cellulose acetate; malt; gelatin; talc; as well as other non-toxic compatible lubricants such as sodium lauryl sulfate and magnesium stearate, as well as coloring agents, releasing agents, coating agents, sweetening, flavoring and perfuming agents; preservatives and antioxidants can also be present in the composition, according to the judgment of the formulator.

It is further intended to include within the scope of the present invention the use of the compounds of Formula (I) or pharmaceutically acceptable salts thereof in combination with at least one therapeutically active agent.

According to one embodiment, the present invention provides a pharmaceutical composition, comprising a therapeutically effective amount of a compound of Formula (I) or a pharmaceutically acceptable salt thereof and at least one further therapeutically active agent, together with a pharmaceutically acceptable carrier.

In an embodiment, the present invention relates to use of the compound of Formula (I) or a pharmaceutically acceptable salt thereof; in combination with a further therapeutically active compound, in the treatment or prophylaxis of a disease or a disorder mediated by GPR120.

The therapeutically active agent used in combination with one or more of the compounds of Formula (I) can be selected from the compounds or active substances known to be used in the treatment of diabetes and other conditions such as obesity, insulin resistance, hyperglycemia, glucose intolerance, hypercholesterolemia, hypertriglylceridemia, dyslipidemia, hyperlipoproteinemia, hyperinsulinemia or atherosclerosis. According to the present invention, the therapeutically active agent, used in combination with the compounds of Formula (I) of the present invention can be selected from, but not limited to, insulin, sulfonylureas, biguanidines, meglitinides, oxadiazolidinediones, thiazolidinediones, glucosidase inhibitors, inhibitors of glycogen phosphorylase, glucagon antagonists, HMGCoA reductase inhibitor, GLP-1 (Glucogen-like peptide-1) agonists, potassium channel openers, inhibitors of dipeptidylpeptidase IV (DPP-IV), diglyceride acyltransferase (DGAT) inhibitor, insulin sensitizers, modulators of glucose uptake, modulators of glucose transport and modulators of glucose reabsorption, modulators of the sodium-dependent glucose transporter 1 or 2 (SGLT1, SGLT2), compounds which alter lipid metabolism such as antihyperlipidemic active ingredients and antilipidemic active ingredients, PPARgamma agonists and agents with combined PPARalpha and gamma activity and active ingredients which act on the ATP-dependent potassium channel of the beta cells.

In an embodiment, the compound of Formula (I) can be used in combination with a PPAR gamma agonist selected from the group consisting of, but not limited to, rosiglitazone, pioglitazone and rivoglitazone.

In an embodiment, the compound of Formula (I) can be used in combination with a HMGCoA reductase inhibitor selected from the group consisting of, but not limited to, simvastatin, fluvastatin, pravastatin, lovastatin, atorvastatin, cerivastatin and rosuvastatin.

In an embodiment, the compound of Formula (I) can be used in combination with a sulfonylurea selected from the group consisting of, but not limited to, tolbutamide, glibenclamide, glipizide and glimepiride.

In another embodiment, the compound of the Formula (I) can be used in combination with a meglitinide selected from the group consisting of, but not limited to, repaglinide, nateglinide and mitiglinide.

In another embodiment, the compound of the Formula (I) can be used in combination with GLP-1 agonist selected from the group consisting of, but not limited to, exenatide, liraglutide, taspoglutide albiglutide and lixisenatide.

In another embodiment, the compound of the Formula (I) can be used in combination with DPP-IV inhibitor selected from the group consisting of, but not limited to, alogliptin, gemigliptin, linagliptin, saxagliptin, sitagliptin and vildagliptin.

Accordingly, in an embodiment the further therapeutically active agent that can be used in combination with one or more compounds of Formula (I) encompassed in the present invention, can be selected from one or more of the agents including, but not limited to, insulin, rosiglitazone, pioglitazone, rivoglitazone, simvastatin, fluvastatin, pravastatin, lovastatin, atorvastatin, cerivastatin, rosuvastatin, tolbutamide, glibenclamide, glipizide, glimepiride, repaglinide, nateglinide, mitiglinide, exenatide, liraglutide, taspoglutide albiglutide, lixisenatide, alogliptin, gemigliptin, linagliptin, saxagliptin, sitagliptin, and vildagliptin.

The pharmaceutical compositions according to the present invention are prepared in a manner known and familiar to one skilled in the art. Pharmaceutically acceptable inert inorganic and/or organic carriers and/or additives can be used in addition to the compounds of Formula (I) and/or its pharmaceutically acceptable salts. For the production of pills, tablets, coated tablets and hard gelatin capsules it is possible to use, for example, lactose, corn starch or derivatives thereof, gum arabic, magnesia and glucose. Carriers for soft gelatin capsules and suppositories are, for example, fats, waxes, natural or hardened oils. Suitable carriers for the production of solutions, for example injection solutions, or emulsions or syrups are, for example, water, sodium chloride solution or alcohols, for example, ethanol, propanol or glycerol, sugar solutions, such as glucose solutions or mannitol solutions.

Further, the pharmaceutical composition of the present invention also contains additives for example, fillers, antioxidants, emulsifiers, preservatives, flavours, solubilisers or colourants. The pharmaceutical composition of the present invention can also contain two or more compounds of Formula (I) and/or its pharmaceutically acceptable salts, the pharmaceutical compositions can also contain one or more other therapeutically or prophylactically active ingredients.

The pharmaceutical compositions normally contain about 1 to 99%, for example, about 5 to 85%, or 10 to 75% by weight of the compounds of Formula (I) or their pharmaceutically acceptable salts.

The amount of the active ingredient, the compound of Formula (I) or its pharmaceutically acceptable salt in the pharmaceutical compositions can, for example, vary from about 1 to 500 mg. In case of higher body weight of the subject in need of the treatment, the pharmaceutical composition can contain the compound of Formula (I) in an amount ranging from 5 mg to 1000 mg. The desirable dosage of the compounds of Formula (I) can be selected over a wide range. The daily dosage to be administered is selected to achieve the desired therapeutic effect in subjects being treated for metabolic disorders. A dosage of about 0.05 to 50 mg/kg/day of the compounds of Formula (I) or its pharmaceutically acceptable salt can be administered. In case of higher body weight of the mammal in need of the treatment, a dosage of about 0.1 to 100 mg/kg/day of the compound of Formula (I) or its pharmaceutically acceptable salt can be administered. If required, higher or lower daily dosages can also be administered. Actual dosage levels of the active ingredients in the pharmaceutical composition of this present invention can be varied so as to obtain an amount of the active ingredient, which is effective to achieve the desired therapeutic response for a particular patient, composition, and mode of administration without being toxic to the patient. The selected dosage level can be readily determined by a skilled medical practitioner in the light of the relevant circumstances, including the condition (diseases or disorder) to be treated, the chosen route of administration depending on a number of factors, such as age, weight and physical health and response of the individual patient, pharmacokinetics and severity of the disease.

The pharmaceutical compositions according to the present invention can be administered orally, for example in the form of pills, tablets, coated tablets, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of solutions or transdermal patches, or in other ways, for example in the form of aerosols or nasal sprays.

It is understood that modifications that do not substantially affect the activity of the various embodiments of this invention are included within scope of the invention disclosed herein. Accordingly, the following examples are intended to illustrate but are not to limit scope of the present invention.

The abbreviations and terms that are used herein:

| LIST OF ABBREVIATIONS | | | |
|---|---|---|---|
| DCM | Dichloromethane | μM | Micromolar |
| DMF | N,N-dimethyl formamide | min(s) | Minute(s) |
| DMSO | Dimethyl sulfoxide | mL | Millilitre |
| g | Gram | nM | Nanomolar |
| mg | Milligram | $NH_4Cl$ | Ammonium chloride |
| h | Hour(s) | THF | Tetrahydrofuran |
| HCl | Hydrochloric acid | d | Doublet |
| $K_2CO_3$ | Potassium carbonate | s | Singlet |
| $LiOH·H_2O$ | Lithium hydroxide monohydrate | m | Multiplet |
| ° C. | Degree Celsius | MHz | Megahertz |
| mmol | Millimole | $^1H$ NMR | Proton nuclear magnetic resonance |
| RT | Room temperature (20° C.-25° C.) | DMSO-$d_6$ | Deuterated dimethylsulfoxide |
| PEPPSI-IPr catalyst | [1,3-Bis(2,6-diisopropylphenyl)imidazol-2-ylidene](3-chloropyridyl) palladium(II) dichloride | | |

Example 1

Synthesis of 4-(4-((4'-(1-cyanocyclopropyl)-3,4,5,6-tetrahydro-[1,1'-biphenyl]-2-yl)methoxy)phenyl) butanoic Acid Step 1a Synthesis of methyl 4-(4-((2-bromocyclohex-1-en-1-yl)methoxy)phenyl)butanoate A mixture of methyl 4-(4-hydroxyphenyl)butanoate (0.765 g, 3.94 mmol), 1-bromo-2-(bromomethyl)cyclohex-1-ene (1 g, 3.91 mmol) and cesium carbonate (1.92 g, 5.91 mmol) in dry acetonitrile (10 mL) was stirred overnight at room temperature. After completion of the reaction, the reaction mixture was diluted with ethyl acetate (30 mL) and filtered. The filtrate was concentrated under vacuum and the material obtained was purified by column chromatography (10%, ethyl acetate/pet ether) to obtain the title compound (0.780 g). Yield: 54%

$^1H$ NMR (300 MHz, $CDCl_3$): δ 7.10-7.08 (d, J=8.4 Hz, 2H), 6.86-6.83 (d, J=8.4 Hz, 2H), 4.66 (s, 2H), 3.67 (s, 3H), 2.62-2.54 (m, 4H), 2.35-2.30 (t, 2H), 2.24 (bs, 2H), 1.98-1.88 (m, 2H), 1.8-1.6 (m, 4H); Mass (m/z): 366.6 (M−1).

Step 1b

Synthesis of methyl 4-(4-((4'-(1-cyanocyclopropyl)-3,4,5,6-tetrahydro-[1,1'-biphenyl]-2-yl)methoxy)phenyl)butanoate The compound obtained in step 1a, methyl 4-(4-((2-bromocyclohex-1-en-1-yl)methoxy)phenyl)butanoate (0.200 g, 0.545 mmol) and (4-(1-cyanocyclopropyl)phenyl) boronic acid (0.102 g, 0.545 mmol) were dissolved in 1, 4-dioxane: water (4:1). Sodium bicarbonate (0.114 g, 1.36 mmol) was added to the mixture and purged with argon for 5 minutes. Tetrakis(triphenylphosphine)palladium(0) (0.063 g, 0.054 mmol) was added to the mixture and purged with argon for 5 minutes. The reaction mixture was heated at 110° C. for 5 hours. The reaction mixture was concentrated under high vacuum and diluted with water (50 mL). The mixture was extracted with ethyl acetate (4×20 mL), the combined organic layer was dried over sodium sulfate and concentrated. The material obtained was purified by column chromatography (0-10% ethyl acetate/petroleum ether) to afford the title compound (0.042 g). Yield: 18%
$^1$H NMR (300 MHz, DMSO-$d_6$): δ 7.24-7.15 (m, 2H), 7.04-7.02 (d, J=8.4 Hz, 1H), 6.73-6.70 (d, J=8.7 Hz, 1H), 4.24 (s, 2H), 3.66 (s, 3H), 2.59-2.54 (t, 2H), 2.33-2.28 (m, 6H), 1.95-1.88 (m, 2H), 1.75-1.69 (m, 5H), 1.58 (m, 2H), 1.43-1.38 (m, 2H); Mass (m/z): 452.2 (M+23), 428.6 (M−1).

Step 1c

Synthesis of 4-(4-((4'-(1-cyanocyclopropyl)-3,4,5,6-tetrahydro-[1,1'-biphenyl]-2-yl)methoxy)phenyl) butanoic Acid The compound obtained in step 1b, methyl 4-(4-((4'-(1-cyanocyclopropyl)-3,4,5,6-tetrahydro-[1,1'-biphenyl]-2-yl)methoxy)phenyl)butanoate (0.035 g, 0.081 mmol) was suspended in THF (4 mL) and methanol (1 mL). Lithium hydroxide solution (0.326 mL, 0.486 mmol) solution was added to the mixture and the reaction mixture was stirred overnight at room temperature. After the completion of reaction, the reaction mixture was concentrated under vacuum. The material obtained was triturated with saturated solution of ammonium chloride (25 mL) and extracted with ethyl acetate (4×20 mL). The combined organic layer was dried over sodium sulfate and concentrated under vacuum to afford the title compound (0.029 g).
Yield: 86%
$^1$H NMR (300 MHz, DMSO-$d_6$): δ 7.02-6.99 (d, J=81 Hz, 2H), 6.71-6.69 (d, J=8.1 Hz, 2H), 4.22 (s, 2H), 2.48-2.12 (m, 6H), 1.72-1.61 (m, 6H), 1.48 (m, 2H), 1.21-1.16 (m, 4H); Mass (m/z): 438.3 (M+23).

Example 2

Synthesis of 4-(4-((2-(5,6,7,8-tetrahydroquinolin-3-yl)cyclohex-1-en-1-yl)methoxy)phenyl) butanoic Acid Step 2a Synthesis of methyl 4-(4-((2-(4,4,5,5-tetramethyl-1,3,2-dioxaborolan-2-yl)cyclohex-1-en-1-yl)methoxy)phenyl)butanoate The compound obtained in step 1a of example 1, methyl 4-(4-((2-bromocyclohex-1-en-1-yl)methoxy)phenyl)butanoate (0.200 g, 0.545 mmol) and 4,4,4',4',5,5,5',5'-octamethyl-2,2'-bi(1,3,2-dioxaborolane) (0.346 g, 1.361 mmol) were stirred in dry 1, 4-dioxane (5 mL) and purged with dry argon gas for 5 minutes. Potassium acetate (214 mg, 2.178 mmol) and [1,1'-bis(diphenylphosphino)ferrocene]dichloropalladium(II), complex with dichloromethane (38 mg, 0.054 mmol) were added to the mixture and the reaction mixture was heated at 80° C. for 8 hours. After completion of the reaction, solvent was removed from the reaction mixture under reduced pressure to afford the title compound (0.200 g), which was purified by column chromatography (0-10% ethyl acetate/petroleum ether). Yield: 89%
$^1$H NMR (300 MHz, DMSO-$d_6$): δ 7.08 (d, J=8.4 Hz, 2H), 6.89 (d, J=8.4 Hz, 2H), 4.74 (s, 2H), 3.67 (s, 3H), 2.58 (t, J=7.5 Hz, 15 Hz, 2H), 2.33 (t, J=7.5 Hz, 15 Hz, 2H), 2.20-2.18 (m, 4H), 1.97-1.90 (m, 2H), 1.61-1.55 (m, 4H), 1.26 (s, 12H); Mass (m/z): 437 (M+23).

Step 2b

Synthesis of methyl 4-(4-((2-(5,6,7,8-tetrahydroquinolin-3-yl)cyclohex-1-en-1-yl)methoxy)phenyl)butanoate The compound obtained in step 2a, methyl 4-(4-((2-(4,4,5,5-tetramethyl-1,3,2-dioxaborolan-2-yl)cyclohex-1-en-1-yl)methoxy)phenyl)butanoate (0.205 g, 0.495 mmol) and 3-bromo-5,6,7,8-tetrahydroquinoline (0.070 g, 0.330 mmol) were dissolved in 1, 4-dioxane: and water (4:1). Sodium bicarbonate (0.069 g, 0.825 mmol) was added to the solution obtained and the mixture was purged with argon for 5 minutes. Tetrakis(triphenylphosphine)palladium(0) (4.77 mg, 0.017 mmol) was added to mixture and purged with argon for 5 minutes. The reaction mixture was heated at temperature 110° C. for 5 hours. After the completion of the reaction, the reaction mixture was concentrated under high vacuum, diluted with water (50 mL) and the aqueous layer was extracted with ethyl acetate (4×20 mL). The combined organic layer was dried over sodium sulfate and concentrated. The material obtained was purified by column chromatography (0-10% ethyl acetate/petroleum ether) to afford the title compound (0.085 g). Yield: 61.4%
$^1$H NMR (500 MHz, CDCl$_3$): δ 8.19 (s, 1H), 7.19 (s, 1H), 7.05 (d, J=8.5 Hz, 2H), 6.74 (d, J=8.5 Hz, 2H), 4.29 (s, 2H), 3.67 (s, 3H), 2.92-2.90 (m, 2H), 2.72-2.70 (m, 2H), 2.59-2.56 (m, 2H), 2.33-2.30 (m, 5H), 1.96-1.89 (m, 4H), 1.82-1.77 (m, 6H), 1.26 (s, 3H); Mass (m/z): 420 (M+1).

Step 2c

Synthesis of 4-(4-((2-(5,6,7,8-tetrahydroquinolin-3-yl)cyclohex-1-en-1-yl)methoxy)phenyl) butanoic Acid The compound obtained in step 2b, methyl 4-(4-((2-(5,6,7,8-tetrahydroquinolin-3-yl)cyclohex-1-en-1-yl)methoxy)phenyl)butanoate (0.080 g, 0.191 mmol) was dissolved in THF (4 mL) and methanol (1 mL). Aqueous solution of LiOH.H$_2$O (0.763 mL, 1.144 mmol) was added to the solution and the mixture was stirred overnight at room temperature. The reaction mixture was concentrated and the reaction mass obtained was quenched with saturated solution of ammonium chloride (20 mL) and the mixture was extracted with ethyl acetate (4×20 mL). The combined organic layer was dried over sodium sulphate and concentrated under high vacuum to afford the title compound (0.071 g). Yield: 92%

¹H NMR (500 MHz, CDCl₃): δ 7.79 (s, 1H), 7.22 (s, 1H), 7.10 (d, J=8.5H, 2H), 6.73 (d, J=8.5 Hz, 2H), 4.28 (s, 2H), 2.90-2.87 (m, 2H), 2.74-2.72 (m, 2H), 2.67-2.64 (m, 2H), 2.38 (s, 2H), 2.33-2.28 (m, 4H), 1.88-1.85 (m, 2H), 1.79-1.78 (m, 6H), 1.29-1.24 (m, 2H); Mass (m/z): 406 (m+1).

Example 3

Synthesis of 4-(4-((2-(2,3-dihydro-1H-inden-5-yl) cyclohex-1-en-1-yl)methoxy)phenyl) butanoic Acid Step 3a Synthesis of methyl 4-(4-((2-(2,3-dihydro-1H-inden-5-yl) cyclohex-1-en-1-yl) methoxy) phenyl) butanoate The compound obtained in step 2a, methyl 4-(4-((2-(4,4,5,5-tetramethyl-1,3,2-dioxaborolan-2-yl)cyclohex-1-en-1-yl)methoxy)phenyl)butanoate (0.221 g, 0.533 mmol) and 5-bromo-2,3-dihydro-1H-indene (0.070 g, 0.355 mmol) were dissolved in 1, 4-dioxane:water (4:1). Sodium bicarbonate (0.075 g, 0.888 mmol) was added to the solution obtained and the mixture was purged with argon for 5 minutes. Tetrakis(triphenylphosphine)palladium(0) (0.010 g, 0.035 mmol) was added to the reaction mixture and purged with argon for 5 minutes. The reaction mixture was heated at temperature 110'C for 5 hours. After the completion of the reaction, the reaction mixture was concentrated under high vacuum, diluted with water (50 mL) and extracted with ethyl acetate (4×20 mL). The combined organic layer was dried over sodium sulfate and concentrated. The material obtained was purified by column chromatography (0-10% ethyl acetate/petroleum ether) to afford the title compound (0.023 g). Yield: 16.01%

¹H NMR (500 MHz, CDCl₃): δ 7.17 (d, J=8 Hz, 1H), 7.05-7.02 (m, 3H), 6.96 (d, J=8 Hz, 1H), 6.75 (d, J=8.5 Hz, 2H), 4.33 (s, 2H), 3.68 (s, 3H), 2.91-2.86 (m, 4H), 2.60-2.56 (m, 2H), 2.35-2.30 (m, 6H), 2.10-2.05 (m, 3H), 1.94-1.88 (m, 2H), 1.57 (s, 3H); Mass (m/z): 427 (M+23).

Step 3b

Synthesis of 4-(4-((2-(2,3-dihydro-1H-inden-5-yl) cyclohex-1-en-1-yl)methoxy)phenyl) butanoic Acid The compound obtained in step 3a, methyl 4-(4-((2-(2,3-dihydro-1H-inden-5-yl) cyclohex-1-en-1-yl))phenyl)butanoate (0.020 g, 0.049 mmol) was dissolved in THF (2 mL) and methanol (0.5 mL) followed by addition of aqueous solution of LiOH.H₂O (0.198 mL, 0.297 mmol). The reaction mixture was stirred overnight at room temperature. The reaction mixture was concentrated and the reaction mass obtained was quenched with saturated solution of ammonium chloride (20 mL) and the mixture was extracted with ethyl acetate (3×10 mL). The combined organic layer was dried over sodium sulphate and concentrated under high vacuum to afford the title compound (0.018 g). Yield: 93%

¹H NMR (500 MHz, CDCl₃): δ 7.17 (d, J=7.5 Hz, 1H), 7.05-7.03 (m, 3H), 6.96 (d, J=7.5 Hz, 1H), 6.75 (d, J=8.5 Hz, 2H), 4.35 (s, 2H), 2.91-2.86 (m, 4H), 2.62-2.58 (m, 3H), 2.39-2.29 (m, 7H), 2.10-2.04 (m, 3H), 1.95-1.89 (m, 3H); Mass (m/z): 413 (M+Na).

Example 4

4-(4-((2-(4,5,6,7-tetrahydrobenzo[d]thiazol-2-yl) cyclohex-1-en-1-yl)methoxy)phenyl) butanoic Acid Step 4a Synthesis of 4-(4-((2-(4,5,6,7-tetrahydrobenzo[d] thiazol-2-yl)cyclohex-1-en-1-yl)methoxy) phenyl) butanoate The title compound was prepared in an analogous manner as described in step 3a of example 3 involving the reaction of the compound obtained in step 2a, methyl 4-(4-((2-(4,4,5,5-tetramethyl-1,3,2-dioxaborolan-2-yl)cyclohex-1-en-1-yl)methoxy)phenyl)butanoate (0.199 g, 0.481 mmol) with 2-bromo-4,5,6,7-tetrahydrobenzo[d]thiazole (0.070 g, 0.321 mmol) in the presence of sodium bicarbonate (0.067 g, 0.802 mmol) and tetrakis(triphenylphosphine)palladium(0) (9.27 mg, 0.032 mmol) to afford the title compound (0.050 g). Yield: 36.6%

¹H NMR, (300 MHz, CDCl₃): δ 7.06 (d, J=8.4 Hz, 2H), 6.80 (d, J=8.4 Hz, 2H), 4.83 (s, 2H), 3.66 (s, 3H), 2.78 (d, J=5.7 Hz, 4H), 2.60-2.55 (m, 2H), 2.49 (s, 2H), 2.34-2.29 (m, 4H), 1.96-1.86 (m, 6H), 1.71 (bs, 4H); Mass (m/z): 426 (M+1).

Step 4b

Synthesis of 4-(4-((2-(4,5,6,7-tetrahydrobenzo[d] thiazol-2-yl)cyclohex-1-en-1-yl) methoxy)phenyl) butanoic Acid The title compound was prepared in an analogous manner as in step 3b of example 3 involving the reaction of methyl 4-(4-((2-(4,5,6,7-tetrahydrobenzo[d]thiazol-2-yl)cyclohex-1-en-1-yl)methoxy)phenyl)butanoate (compound obtained in step 4a) (0.050 g, 0.117 mmol) with LiOH.H₂O (0.470 mL, 0.705 mmol) to afford the title compound (0.040 g). Yield: 83%. ¹H NMR (500 MHz, CDCl₃): δ 7.07 (d, J=8.5 Hz, 2H), 6.81 (d, J=8.5H, 2H), 4.38 (s, 2H), 2.80-2.77 (m, 4H), 2.63-2.60 (m, 2H), 2.50 (s, 2H), 2.38-2.35 (m, 4H), 1.97-1.91 (m, 8H), 1.76-1.75 (m, 2H); Mass (m/z): 412 (M+1)

Example 5

4-(4-((4'-cyano-3,4,5,6-tetrahydro-[1,1'-biphenyl]-2-yl)methoxy)phenyl)butanoic Acid Step 5a Synthesis of methyl 4-(4-((4'-cyano-3,4,5,6-tetrahydro-[1,1'-biphenyl]-2-yl)methoxy)phenyl) butanoate The title compound was prepared in an analogous manner as described in step 1b of example 1 involving the reaction of methyl 4-(4-((2-bromocyclohex-1-en-1-yl)methoxy)phenyl)butanoate (0.150 g, 0.408 mmol) and (4-cyanophenyl) boronic acid (0.229 g, 1.558 mmol) in the presence of sodium bicarbonate (0.218 g, 2.60 mmol) and tetrakis(triphenylphosphine)palladium(0) (0.015 g, 0.052 mmol) to afford the title compound (0.025 g). Yield: 6.18%

¹H NMR (300 MHz, DMSO-d₆): δ 7.61 (d, J=8.1 Hz, 2H), 7.31 (d, J=8.4 Hz, 2H), 7.05 (d, J=8.7 Hz, 2H), 6.71 (d, J=8.7

Hz, 2H), 4.20 (s, 2H), 3.66 (s, 3H), 2.57 (t, J=7.2 Hz, 15 Hz, 2H), 2.33-2.28 (m, 6H), 1.90-1.85 (m, 2H), 1.77 (s, 4H); Mass (m/z): 412 (M+23).

Step 5b

Synthesis of 4-(4-((4'-cyano-3,4,5,6-tetrahydro-[1,1'-biphenyl]-2-yl)methoxy) phenyl) butanoic Acid The title compound was prepared in an analogous manner as described in step 3b of example 3 involving the reaction of methyl 4-(4-((4'-cyano-3,4,5,6-tetrahydro-[1,1'-biphenyl]-2-yl)methoxy)phenyl) butanoate (compound obtained in step 5a) (0.025 g, 0.064 mmol) with LiOH.H$_2$O (0.470 mL, 0.705 mmol) to afford the title compound (0.020 g). Yield: 74.9%.

$^1$H NMR (500 Hz, CDCl$_3$): δ 7.61 (d, J=8 Hz, 2H), 7.31 (d, J=8H, 2H), 7.06 (d, J=8.5 Hz, 2H), 6.72 (d, J=8.5 Hz, 2H), 4.24 (s, 2H), 2.62-2.59 (m, 2H), 2.38-2.33 (m, 6H), 2.12-2.03 (m, 4H), 1.79 (s, 2H); Mass (m/z): 398 (M+23).

Example 6

Synthesis of 4-(4-((4'-methoxy-3,4,5,6-tetrahydro-[1,1'-biphenyl]-2-yl)methoxy) phenyl)butanoic Acid Step 6a Synthesis of methyl 4-(4-((4'-methoxy-3,4,5,6-tetrahydro-[1,1'-biphenyl]-2-yl) methoxy)phenyl) butanoate The title compound was prepared in an analogous manner as described in step 1b of example 1 involving the reaction of methyl 4-(4-((2-bromocyclohex-1-en-1-yl)methoxy)phenyl)butanoate (0.150 g, 0.408 mmol) with (4-methoxyphenyl)boronic acid (0.237 g, 1.560 mmol) in presence of sodium bicarbonate (0.218 g, 2.60 mmol) and tetrakis(triphenylphosphine)palladium(0) (0.015 g, 0.052 mmol) to afford the title compound (0.028 g). Yield: 6.83%

$^1$H NMR (300 MHz, DMSO-d$_6$): δ 7.13 (d, J=8.4 Hz, 2H), 7.04 (d, J=8.4 Hz, 2H), 6.86 (d, J=8.7 Hz, 2H), 6.74 (d, J=8.7 Hz, 2H), 4.30 (s, 2H), 3.80 (s, 3H), 3.66 (s, 3H), 2.56 (t, J=7.5 Hz, 15 Hz, 2H), 2.31 (t, J=7.2 Hz, 14.7 Hz, 6H), 1.95-1.85 (m, 2H), 1.74 (s, 4H); Mass (m/z): 417 (M+23).

Step 6b

Synthesis of 4-(4-((4'-methoxy-3,4,5,6-tetrahydro-[1,1'-biphenyl]-2-yl)methoxy) phenyl)butanoic Acid The title compound was prepared in an analogous manner as described in step 3b of example 3 involving the reaction of the compound obtained in step 6a, methyl 4-(4-((4'-cyano-3,4,5,6-tetrahydro-[1,1'-biphenyl]-2-yl)methoxy) phenyl) butanoate (0.022 g, 0.056 mmol) with LiOH.H$_2$O (0.470 mL, 0.705 mmol) to afford the title compound (0.020 g). Yield: 94%.

$^1$H NMR (500 MHz, CDCl$_3$): δ 7.14-7.12 (d, J=8.5 Hz, 2H), 7.07-7.00 (m, 2H), 6.86 (d, J=8.5 Hz, 2H), 6.75 (d, J=8.5 Hz, 2H), 4.31 (s, 2H), 3.81 (s, 3H), 2.60 (t, J=7.5 Hz, J=15 Hz, 4H), 2.29 (s, 4H), 1.96-1.90 (m, 2H), 1.75 (s, 4H); Mass (m/z): 403 (M+23).

Example 7

Synthesis of 4-(4-((4'-cyclopropyl-3,4,5,6-tetrahydro-[1,1'-biphenyl]-2-yl)methoxy) phenyl)butanoic Acid Step 7a Synthesis of methyl 4-(4-((4'-cyclopropyl-3,4,5,6-tetrahydro-[1,1'-biphenyl]-2-yl)methoxy)phenyl) butanoate The title compound was prepared in an analogous manner as in step 1b of example 1 involving the reaction of methyl 4-(4-((2-bromocyclohex-1-en-1-yl)methoxy)phenyl)butanoate (0.150 g, 0.408 mmol) and (4-cyclopropylphenyl)boronic acid (0.099 g, 0.613 mmol) in presence of sodium bicarbonate (0.086 g, 1.021 mmol) and tetrakis(triphenylphosphine)palladium(0) (5.90 mg, 0.020 mmol) to afford the title compound (0.110 g). Yield: 66.6%

$^1$H NMR (300 MHz, DMSO-d$_6$): δ 7.09 (d, J=8.4 Hz, 2H), 7.04-6.99 (m, 4H), 6.74 (d, J=8.1 Hz, 2H), 4.29 (s, 2H), 3.66 (s, 3H), 2.56 (t, J=7.5 Hz, 15 Hz, 2H), 2.31 (t, J=7.2 Hz, 14.7 Hz, 6H), 1.95-1.85 (m, 3H), 1.17 (s, 4H), 0.98-0.92 (m, 2H), 0.71-0.66 (m, 2H); Mass (m/z): 427.5 (M+23).

Step 7b

Synthesis of 4-(4-((4'-cyclopropyl-3,4,5,6-tetrahydro-[1,1'-biphenyl]-2-yl)methoxy)phenyl)butanoic Acid The title compound was prepared in an analogous manner as described in step 3b of example 3 involving the reaction of methyl 4-(4-((4'-cyclopropyl-3,4,5,6-tetrahydro-[1,1'-biphenyl]-2-yl)methoxy)phenyl)butanoate (compound obtained in step 7a) (0.100 g, 0.247 mmol) with LiOH.H$_2$O (0.989 mL, 1.483 mmol) to afford the title compound (0.089 g). Yield: 92%

$^1$H NMR (300 MHz, DMSO-d$_6$): δ 12.04 (s, 1H), 7.05-6.99 (m, 6H), 6.69-6.67 (m, 2H), 4.56 (s, 2H), 2.24-2.12 (m, 6H), 1.96-1.84 (m, 1H), 1.72-1.64 (m, 6H), 1.32 (s, 2H), 1.20-1.15 (m, 2H), 0.90-0.88 (m, 2H); Mass (m/z): 413 (M+23).

Example 8

Synthesis of 4-(4-((2-(6-amino-5-(trifluoromethyl) pyridin-3-yl)cyclohex-1-en-1-yl)methoxy)phenyl) butanoic Acid Step 8a Synthesis of methyl 4-(4-((2-(6-amino-5-(trifluoromethyl)pyridin-3-yl)cyclohex-1-en-1-yl)methoxy) phenyl)butanoate The title compound was prepared in an analogous manner as in step 2b of example 2 involving the reaction of 5-(4,4,5,5-tetramethyl-1,3,2-dioxaborolan-2-yl)-3-(trifluoromethyl)pyridin-2-amine (0.176 g, 0.613 mmol) and methyl 4-(4-((2-bromocyclohex-1-en-1-yl)methoxy)phenyl) butanoate (0.150 g, 0.408 mmol) in presence of sodium bicarbonate (0.086 g, 1.021 mmol) and tetrakis(triphenylphosphine)palladium(0) (5.90 mg, 0.020 mmol) to afford the title compound (0.125 g). Yield: 68.2%

¹H NMR (300 MHz, DMSO-d₆): δ 8.08 (s, 1H), 7.57 (s, 1H), 7.05 (d, J=8.7 Hz, 2H), 6.74 (d, J=8.7 Hz, 2H), 4.93 (s, 2H), 4.26 (s, 2H), 3.66 (s, 3H), 2.59-2.54 (m, 2H), 2.33-1.95-1.85 (m, 2H), 1.76 (s, 4H), 2.33-2.28 (m, 6H); Mass (m/z): 449 (M+1)

Step 8b

Synthesis of 4-(4-((2-(6-amino-5-(trifluoromethyl) pyridin-3-yl)cyclohex-1-en-1-yl)methoxy)phenyl) butanoic Acid The title compound was prepared in an analogous manner as in step 2c of example 2 involving the reaction of the compound obtained in step 8a, methyl 4-(4-((2-(6-amino-5-(trifluoromethyl)pyridin-3-yl)cyclohex-1-en-1-yl)methoxy) phenyl)butanoate (0.120 g, 0.268 mmol) with LiOH.H₂O (1.070 mL, 1.605 mmol) to afford the title compound (0.090 g). Yield: 77%
¹H NMR (300 MHz, DMSO-d₆): δ 12.02 (s, 1H), 8.04 (s, 1H), 7.57 (s, 1H), 7.04 (d, J=8.4 Hz, 2H), 6.76 (d, J=8.7 Hz, 2H), 6.42 (s, 2H), 4.21 (s, 2H), 2.28-2.14 (m, 6H), 1.74-1.66 (m, 6H), 1.26-1.16 (m, 2H); Mass (m/z): 435 (M+1).

Example 9

Synthesis of 4-(4-((2-(5,6,7,8-tetrahydronaphthalen-2-yl)cyclohex-1-en-1-yl)methoxy) phenyl) butanoic Acid Step 9a Synthesis of methyl 4-(4-((2-(5,6,7,8-tetrahydronaphthalen-2-yl)cyclohex-1-en-1-yl)methoxy) phenyl) butanoate The title compound was prepared in an analogous manner as in step 1b of Example 1 involving the reaction of methyl 4-(4-((2-bromocyclohex-1-en-1-yl)methoxy)phenyl)butanoate (0.150 g, 0.408 mmol) and 5,6,7,8-tetrahydronaphthalen-2-yl)boronic acid (0.108 g, 0.613 mmol) in presence of sodium bicarbonate (0.086 g, 1.021 mmol) and tetrakis (triphenylphosphine)palladium(0) (5.90 mg, 0.020 mmol) to afford the title compound (0.080 g). Yield: 47%
¹H NMR (CDCl₃, 300 MHz): δ 7.30-7.38 (m, 1H), 7.20-7.30 (m, 1H), 6.95-7.15 (m, 6H), 6.79 (d, J=8.7 Hz, 2H), 4.92 (s, 2H), 3.66 (s, 3H), 2.69-2.85 (m, 4H), 2.58 (t, J=7.5 Hz, 2H), 2.31 (t, J=7.5 Hz, 2H), 1.85-2.00 (m, 2H), 1.75-1.85 (m, 4H); Mass (m/z): 455.1 (M+Na⁺).

Step 9b

Synthesis of 4-(4-((2-(5,6,7,8-tetrahydronaphthalen-2-yl)cyclohex-1-en-1-yl)methoxy) phenyl) butanoic Acid The title compound was prepared in an analogous manner as in step 1c Example 1 involving the reaction of the compound obtained in step 9a, methyl 4-(4-((2-(5,6,7,8-tetrahydronaphthalen-2-yl)cyclohex-1-en-1-yl)methoxy) phenyl) butanoate (0.090 g, 0.215 mmol) with LiOH.H₂O (0.860 mL, 1.290 mmol) to afford the title compound (0.080 g). Yield: 92%
¹H NMR (300 MHz, CDCl₃): δ 7.11-6.98 (m, 3H), 6.92-6.84 (m, 2H), 6.76-6.73 (m, 2H), 4.32 (s, 2H), 2.74-2.70 (m, 4H), 2.59 (t, J=7.2 Hz, 15 Hz, 2H), 2.38-2.28 (m, 6H), 1.96-1.89 (m, 2H), 1.78-1.74 (m, 8H); Mass (m/z): 427 (M+23)

Example 10

Synthesis of 4-(4-([1,1'-bi(cyclohexane)]-1,1'-dien-2-ylmethoxy)phenyl) butanoic Acid Step 10a Synthesis of methyl 4-(4-([1,1'-bi(cyclohexane)]-1,1'-dien-2-ylmethoxy)phenyl)butanoate The title compound was prepared in an analogous manner as in step 1b of Example 1 involving the reaction of methyl 4-(4-((2-bromocyclohex-1-en-1-yl)methoxy)phenyl)butanoate (0.150 g, 0.408 mmol) with cyclohex-1-en-1-ylboronic acid (0.077 g, 0.613 mmol) in presence of sodium bicarbonate (0.086 g, 1.021 mmol) and tetrakis(triphenylphosphine)palladium(0) (0.024 mg, 0.020 mmol) to afford the title compound (0.068 g). Yield: 92%
¹H NMR (DMSO-d₆, 300 MHz): δ 7.08-7.05 (d, J=8.7 Hz, 2H), 6.84-6.81 (d, J=8.4 Hz, 2H), 5.39 (bs, 1H), 4.44 (s, 2H), 3.67 (s, 3H), 2.61-2.56 (t, 2H), 2.33-2.30 (t, 2H), 2.16 (bs, 2H), 2.08-1.95 (m, 6H), 1.92-1.87 (t, 2H), 1.70-1.30 (m, 8H); Mass (m/z): 391.4 (M+23)

Step 10b

Synthesis of 4-(4-([1,1'-bi(cyclohexane)]-1,1'-dien-2-ylmethoxy)phenyl) butanoic Acid The title compound was prepared in an analogous manner as in step 1c of Example 1 involving the reaction of the compound obtained in step 10a, methyl 4-(4-([1,1'-bi(cyclohexane)]-1,1'-dien-2-ylmethoxy)phenyl)butanoate (0.100 g, 0.271 mmol) with LiOH.H₂O (1.085 mL, 1.628 mmol) to afford the title compound (0.080 g). Yield: 83%
¹H NMR (DMSO-d₆, 300 MHz): δ 7.09 (d, J=8.7 Hz, 2H), 6.84 (d, J=8.4 Hz, 2H), 4.44 (s, 2H), 2.1 (t, J=7.2 Hz, 15 Hz, 2H), 2.37 (t, J=7.5 Hz, 15 Hz, 2H), 2.16 (s, 2H), 2.08-1.91 (m, 8H), 1.63-1.58 (m, 8H); Mass (m/z): 377 (M+23)

Example 11

Synthesis of 4-(4-((3'-methyl-3,4,5,6-tetrahydro-[1,1'-biphenyl]-2-yl)methoxy) phenyl) butanoic Acid Step 11a Synthesis of methyl 4-(4-((3'-methyl-3,4,5,6-tetrahydro-[1,1'-biphenyl]-2-yl)methoxy)phenyl)butanoate The title compound was prepared in an analogous manner as in step 1b of Example 1 involving the reaction of methyl 4-(4-((2-bromocyclohex-1-en-1-yl)methoxy)phenyl)butanoate (0.150 g, 0.408 mmol) with m-tolylboronic acid (0.083 g, 0.613 mmol) in presence of sodium bicarbonate (0.086 g, 1.02 mmol) and tetrakis(triphenylphosphine)palladium(0) (0.012 g, 0.010 mmol) to afford the title compound (0.110 g). Yield: 71%
¹H NMR (CDCl₃, 300 MHz) δ: 7.22-7.17 (m, 1H), 7.06-6.96 (m, 5H), 6.73 (d, J=8.4 Hz, 2H), 4.29 (s, 2H), 3.66

(s, 3H), 2.56 (t, J=7.2 Hz, 15 Hz, 2H), 2.33-2.28 (m, 9H), 1.95-1.87 (m, 2H), 1.75 (s, 4H). Mass (m/z): 401 (M+23)

Step 11b

Synthesis of 4-(4-((3'-methyl-3,4,5,6-tetrahydro-[1,1'-biphenyl]-2-yl)methoxy) phenyl) butanoic Acid The title compound was prepared in an analogous manner as in step 1c of Example 1 involving the reaction of the compound obtained in step 11a, methyl 4-(4-((3'-methyl-3,4,5,6-tetrahydro-[1,1'-biphenyl]-2-yl)methoxy)phenyl)butanoate (0.100 g, 0.264 mmol) with LiOH.H$_2$O (1.057 mL, 1.585 mmol) to afford the title compound (0.090 g). Yield: 93%

$^1$H NMR (CDCl$_3$, 300 MHz): δ 7.21-7.16 (m, 1H), 7.05-6.95 (m, 5H), 6.71 (d, J=8.4 Hz, 2H), 4.23 (s, 2H), 2.47-2.44 (m, 2H), 2.28-2.23 (m, 7H), 2.13 (t, J=7.2 Hz, 14.4 Hz, 2H), 1.75-1.67 (m, 6H); Mass (m/z): 387 (M+23)

Example 12

Synthesis of 4-(4-((3,4,5,6-tetrahydro-[1,1'-biphenyl]-2-yl)methoxy)phenyl)butanoic Acid Step 12a Synthesis of methyl 4-(4-((3,4,5,6-tetrahydro-[1,1'-biphenyl]-2-yl)methoxy)phenyl)butanoate The title compound was prepared in an analogous manner as in step 1b of Example 1 involving the reaction of methyl 4-(4-((2-bromocyclohex-1-en-1-yl)methoxy)phenyl)butanoate (0.150 g, 0.408 mmol) with phenyl boronic acid (0.075 g, 0.613 mmol) in presence of sodium bicarbonate (0.086 g, 1.02 mmol) and tetrakis(triphenylphosphine)palladium(0) (0.012 g, 0.010 mmol) to afford the title compound (0098 g). Yield: 66%

$^1$H NMR (300 MHz, CDCl$_3$) δ: 7.33-7.28 (m, 2H), 7.23 (s, 1H), 7.20-7.17 (m, 2H), 7.03 (d, J=8.4 Hz, 2H), 6.73 (d, J=8.4 Hz, 2H), 4.29 (s, 2H), 3.66 (s, 3H), 2.58 (t, J=7.5 Hz, 15.3 Hz, 2H), 2.33-2.28 (m, 6H), 1.95-1.87 (m, 2H), 1.75 (s, 4H); Mass (m/z): 387 (M+23)

Step 12b

Synthesis of 4-(4-((3,4,5,6-tetrahydro-[1,1'-biphenyl]-2-yl)methoxy)phenyl)butanoic Acid The title compound was prepared in an analogous manner as in step 1c of Example 1 involving the reaction of the compound obtained in step 12a, methyl 4-(4-((3,4,5,6-tetrahydro-[1,1'-biphenyl]-2-yl)methoxy)phenyl)butanoate (0.090 g, 0.247 mmol) with LiOH.H$_2$O (0.988 mL, 1.48 mmol) to afford the title compound (0.085 g). Yield: 98%.

$^1$H NMR (300 MHz, DMSO-d$_6$): δ 12.03 (s, 1H), 7.34-7.17 (m, 5H), 7.02 (d, J=8.4 Hz, 2H), 6.71 (m, 2H), 4.24 (s, 2H), 2.44 (s, 1H), 2.30-2.13 (m, 6H), 1.73-1.68 (m, 5H), 2.13 (t, J=7.2 Hz, 14.4 Hz, 2H); Mass (m/z): 373 (M+23)

Example 13

4-(4-((2'-methyl-3,4,5,6-tetrahydro-[1,1'-biphenyl]-2-yl)methoxy)phenyl) butanoic Acid Step 13a Synthesis of methyl 4-(4-((2'-methyl-3,4,5,6-tetrahydro-[1,1'-biphenyl]-2-yl)methoxy)phenyl)butanoate The title compound was prepared in an analogous manner as in step 1b of Example 1 involving the reaction of methyl 4-(4-((2-bromocyclohex-1-en-1-yl)methoxy)phenyl)butanoate (0.150 g, 0.408 mmol) with o-tolyl boronic acid (0.083. g, 0.613 mmol) in presence of sodium bicarbonate (0.086 g, 1.02 mmol) and tetrakis(triphenylphosphine)palladium(0) (0.012 g, 0.010 mmol) to afford the title compound (0.105 g). Yield: 68%

$^1$H NMR (300 MHz, CDCl$_3$): δ 7.15-7.12 (m, 3H), 7.01-6.98 (m, 3H), 6.69 (d, J=8.7 Hz, 2H), 4.12 (s, 2H), 3.65 (s, 3H), 2.57 (t, J=7.2 Hz, 15 Hz, 2H), 2.32-2.27 (m, 4H), 2.20 (s, 5H), 1.91-1.86 (m, 2H), 1.77-1.76 (m, 4H); Mass (m/z): 401 (M+23)

Step 13b

Synthesis of 4-(4-((2'-methyl-3,4,5,6-tetrahydro-[1,1'-biphenyl]-2-yl)methoxy)phenyl) butanoic Acid The title compound was prepared in an analogous manner as in step 1c of Example 1 involving the reaction of the compound obtained in step 13a, methyl 4-(4-((2'-methyl-3,4,5,6-tetrahydro-[1,1'-biphenyl]-2-yl)methoxy)phenyl)butanoate (0.095 g, 0.251 mmol) with LiOH.H$_2$O (1.004 mL, 1.506 mmol) to afford the title compound (0.082 g). Yield: 90%

$^1$H NMR (300 MHz, CDCl$_3$): δ 12.07 (s, 1H), 7.16-7.12 (m, 3H), 7.00-6.67 (m, 3H), 6.66 (d, J=8.4 Hz, 2H), 4.09-4.01 (m, 2H), 2.45-2.43 (m, 2H), 2.22 (s, 2H), 2.15-2.12 (m, 7H), 1.70 (s, 6H); Mass (m/z): 387 (M+23)

Example 14

Synthesis of 4-(4-((2-(6-methoxypyridin-3-yl)cyclohex-1-en-1-yl)methoxy)phenyl) butanoic Acid Step 14a Synthesis of methyl 4-(4-((2-(6-methoxypyridin-3-yl)cyclohex-1-en-1-yl)methoxy)phenyl)butanoate The title compound was prepared in an analogous manner as in step 1b of Example 1 involving the reaction of methyl 4-(4-((2-bromocyclohex-1-en-1-yl)methoxy)phenyl)butanoate (0.176 g, 0.479 mmol) with 6-methoxypyridin-3-yl boronic acid (0.110 g, 0.719 mmol) in presence of sodium bicarbonate (0.101 g, 1.198 mmol) and tetrakis(triphenylphosphine)palladium(0) (0.027 mg, 0.024 mmol) to afford the title compound (0.070 g). Yield: 37%

$^1$H NMR (300 MHz, CDCl$_3$): δ 7.99-7.98 (d, J=2, 1 Hz, 1H), 7.43-7.40 (dd, J=8.4 & 2.4 Hz, 1H), 7.04-7.01 (d, J=8.4 Hz, 2H), 6.73-6.68 (m, 3H), 4.28 (s, 2H), 3.92 (s, 3H), 3.66 (s, 3H), 2.58-2.53 (t, 2H), 2.33-2.28 (m, 6H), 1.95-1.87 (m, 2H), 1.75 (m, 4H); Mass (m/z): 396.4 (M+1).

Step 14b

Synthesis of 4-(4-((2-(6-methoxypyridin-3-yl)cyclohex-1-en-1-yl)methoxy)phenyl) butanoic Acid The title compound was prepared in an analogous manner as in step 1c of Example 1 involving the reaction of the compound obtained in step 14a, methyl 4-(4-((2-(6-methoxypyridin-3-yl)cyclohex-1-en-1-yl)methoxy)phenyl) butanoate (0.060 g, 0.152 mmol) with LiOH.H$_2$O (0.606 mL, 0.910 mmol) to afford the title compound (0.046 g). Yield: 80%

$^1$H NMR (300 MHz, DMSO-d$_6$): δ 7.97 (s, 1H), 7.56-7.54 (d, J=6.3 Hz, 1H), 7.03-7.00 (d, J=8.1 Hz, 2H), 6.78-6.71 (m, 3H), 4.23 (s, 2H), 3.79 (s, 3H), 2.27-2.13 (m, 7H), 1.73-1.67 (m, 7H); Mass (m/z): 382.2 (M+23)

Example 15

4-(4-((4'-methyl-3,4,5,6-tetrahydro-[1,1'-biphenyl]-2-yl)methoxy)phenyl) butanoic Acid

Step 15a

Synthesis of methyl 4-(4-((4'-methyl-3,4,5,6-tetrahydro-[1,1'-biphenyl]-2-yl)methoxy)phenyl)butanoate The title compound was prepared in an analogous manner as in step 1b of Example 1 involving the reaction of methyl 4-(4-((2-bromocyclohex-1-en-1-yl)methoxy)phenyl)butanoate (0.175 g, 0.476 mmol) with p-tolylboronic acid (0.097 g, 0.715 mmol) in presence of sodium bicarbonate (0.100 g, 1.19 mmol) and tetrakis(triphenylphosphine)palladium(0) (0.027 mg, 0.024 mmol) to afford the title compound (0.095 g). Yield: 53%

$^1$H NMR (300 MHz, CDCl$_3$): δ 7.13-7.06 (m, 4H), 7.03-7.00 (d, J=8.7 Hz, 2H), 6.73-6.71 (d, J=8.4 Hz, 2H), 4.30 (s, 2H), 3.69 (s, 3H), 2.58-2.53 (m, 2H), 2.33-2.28 (m, 9H), 1.95-1.85 (m, 2H), 1.74 (bt, 4H); Mass (m/z): 401.1 (M+23).

Step 15b

Synthesis of 4-(4-((4'-methyl-3,4,5,6-tetrahydro-[1,1'-biphenyl]-2-yl)methoxy)phenyl) butanoic Acid The title compound was prepared in an analogous manner as in step 1c of Example 1 involving reaction of the compound obtained in step 15a, methyl 4-(4-((4'-methyl-3,4,5,6-tetrahydro-[1,1'-biphenyl]-2-yl)methoxy)phenyl)butanoate (0.085 g, 0.225 mmol) with LiOH.H$_2$O (0.906 mL, 1.347 mmol) to afford the title compound (0.065 g). Yield: 79%.

$^1$H NMR (300 MHz, DMSO-d$_6$): δ 11.77 (bs, 1H), 7.11-7.07 (m, 4H), 7.01-6.98 (d, J=8.4 Hz, 2H), 6.70-6.67 (d, J=8.4 Hz, 2H), 4.22 (s, 2H), 2.43 (m, 2H), 2.24-2.12 (m, 9H), 1.72-1.69 (m, 6H); Mass (m/z): 387.2 (M+23), 362.8 (M-1)

Example 16

Synthesis of 4-(4-((2-(p-tolyl)cyclooct-1-en-1-yl)methoxy)phenyl)butanoic Acid

Step 16a

Synthesis of methyl 4-(4-((2-(p-tolyl)cyclooct-1-en-1-yl)methoxy)phenyl)butanoate The title compound was prepared in an analogous manner as in step 1b of Example 1 involving the reaction of methyl 4-(4-((2-bromocyclohex-1-en-1-yl)methoxy)phenyl)butanoate (0.150 g, 0.379 mmol) with p-tolylboronic acid (0.077 g, 0.569 mmol) in presence of sodium bicarbonate (0.080 g, 0.949 mmol) and tetrakis(triphenylphosphine)palladium(0) (0.027 mg, 0.024 mmol) to afford the title compound (0.090 g). Yield: 58%

$^1$H NMR (300 MHz, CDCl$_3$): δ 7.13-6.99 (m, 6H), 6.71 (d, J=8.4 Hz, 2H), 4.32 (s, 2H), 3.66 (s, 3H), 2.58-2.46 (m, 7H), 2.34 (s, 3H), 2.30-2.27 (m, 2H), 1.94-1.87 (m, 2H), 1.70 (s, 2H), 1.58-1.52 (m, 5H); Mass (m/z): 429 (M+23)

Step 16b

Synthesis of 4-(4-((2-(p-tolyl)cyclo oct-1-en-1-yl)methoxy)phenyl)butanoic Acid

The title compound was prepared in an analogous manner as in step 1c of Example 1 involving the reaction of the compound obtained in step 16a, methyl 4-(4-((2-(p-tolyl)cyclooct-1-en-1-yl)methoxy)phenyl)butanoate (0.085 g, 0.209 mmol) with LiOH.H$_2$O (0.836 mL, 1.25 mmol), to afford the title compound (0.080 mg). Yield: 97%.

$^1$H NMR (300 MHz, CDCl$_3$): δ 7.13-7.00 (m, 6H), 6.71 (d, J=8.4 Hz, 2H), 4.32 (s, 2H), 2.60-2.46 (m, 7H), 2.34 (s, 6H), 1.93-1.88 (m, 3H), 1.70 (s, 3H), 1.28-1.23 (m, 2H); Mass (m/z): 415 (M+23).

Example 17

Synthesis of 4-(4-((2-(m-tolyl)cyclooct-1-en-1-yl)methoxy)phenyl)butanoic Acid

Step 17a

Synthesis of methyl 4-(4-((2-(m-tolyl)cyclooct-1-en-1-yl)methoxy)phenyl)butanoate The title compound was prepared in an analogous manner as in step 1b of Example 1 involving the reaction of methyl 4-(4-((2-bromocyclohex-1-en-1-yl)methoxy)phenyl)butanoate (0.150 g, 0.379 mmol) with m-tolylboronic acid (0.077 g, 0.569 mmol) in presence of sodium bicarbonate (0.080 g, 0.949 mmol) and tetrakis(triphenylphosphine)palladium(0) (0.027 mg, 0.024 mmol) to afford the title compound (0.050 g). Yield: 32%

$^1$H NMR (300 MHz, CDCl$_3$): δ 7.22-7.16 (m, 2H), 7.03-6.94 (m, 4H), 6.71 (d, J=8.4 Hz, 2H), 4.31 (s, 2H), 3.65 (s, 3H), 2.58-2.47 (m, 7H), 2.32 (s, 3H), 2.30-2.27 (m, 2H), 1.94-1.87 (m, 2H), 1.71 (s, 2H), 1.59-1.52 (m, 5H); Mass (m/z): 429 (M+23)

Step 17b

Synthesis of 4-(4-((2-(m-tolyl)cyclooct-1-en-1-yl)methoxy)phenyl)butanoic Acid

The title compound was prepared in an analogous manner as in step 1c of Example 1 involving reaction of the compound obtained in step 17a, methyl 4-(4-((2-(m-tolyl)cyclooct-1-en-1-yl)methoxy)phenyl)butanoate (0.045 g, 0.111 mmol) with LiOH.H$_2$O (0.443 mL, 0.664 mmol) to afford the title compound (0.041 g). Yield: 94%.

$^1$H NMR (300 MHz, CDCl$_3$): δ 7.22-7.17 (m, 1H), 7.06-6.94 (m, 5H), 6.71 (d, J=8.7 Hz, 2H), 4.31 (s, 2H), 2.60-2.47 (m, 7H), 2.37-2.32 (m, 7H), 1.95-1.88 (m, 2H), 1.70 (s, 3H), 1.28-1.23 (m, 2H); Mass (m/z): 415 (M+23).

Example 18

Synthesis of 4-(4-((2-(o-tolyl)cyclooct-1-en-1-yl)methoxy)phenyl)butanoic Acid

Step 18a

Synthesis of methyl 4-(4-((2-(o-tolyl)cyclooct-1-en-1-yl)methoxy)phenyl)butanoate The title compound was prepared in an analogous manner as in step 1b of Example 1 involving the reaction of methyl 4-(4-((2-bromocyclooct-1-en-1-yl)methoxy)phenyl)butanoate (0.150 g, 0.379 mmol) with o-tolylboronic acid (0.077 g, 0.569 mmol) in the presence of sodium bicarbonate (0.080 g, 0.949 mmol) and tetrakis(triphenylphosphine)palladium (0) (0.027 mg, 0.024 mmol) to afford the title compound (0.100 g). Yield: 64%

$^1$H NMR (300 MHz, CDCl$_3$): δ 7.17-7.12 (m, 3H), 7.00-6.96 (m, 3H), 6.67 (d, J=8.7 Hz, 2H), 4.22-4.14 (m, 2H), 3.65 (s, 3H), 2.73-2.69 (m, 2H), 2.56-2.51 (m, 4H), 2.32-2.27 (m, 2H), 2.18-2.12 (m, 5H), 1.93-1.85 (m, 2H), 1.74-1.47 (m, 6H); Mass (m/z): 429 (M+23)

Step 18b

Synthesis of 4-(4-((2-(o-tolyl)cyclooct-1-en-1-yl)methoxy)phenyl)butanoic Acid The title compound was prepared in an analogous manner as in step 1c of Example 1 involving reaction of the compound obtained in step 18a, methyl 4-(4-((2-(o-tolyl)cyclooct-1-en-1-yl)methoxy)phenyl)butanoate (0.095 g, 0.234 mmol) with LiOH.H$_2$O (0.935 mL, 1.40 mmol) to afford the title compound (0.082 g). Yield: 89%.

$^1$H NMR (300 MHz, CDCl$_3$): δ 7.17-7.12 (m, 3H), 7.01-6.96 (m, 3H), 6.67 (d, J=8.4 Hz, 2H), 4.23-4.11 (m, 2H), 2.59-2.49 (m, 4H), 2.33 (t, J=7.5 Hz, 15 Hz, 2H), 2.21 (s, 3H), 2.13-2.05 (m, 2H), 1.80-1.58 (m, 6H), 1.92-1.87 (m, 2H), 1.29-1.25 (m, 2H); Mass (m/z): 415 (M+23).

Example 19

Synthesis of 4-(4-((2-phenylcyclooct-1-en-1-yl)methoxy)phenyl)butanoic Acid

Step 19a

Synthesis of methyl 4-(4-((2-phenylcyclooct-1-en-1-yl)methoxy)phenyl)butanoate The title compound was prepared in an analogous manner as in step 1b of Example 1 involving the reaction of methyl 4-(4-((2-bromocyclooct-1-en-1-yl)methoxy)phenyl)butanoate. (0.150 g, 0.379 mmol) with phenylboronic acid (0.069 g, 0.569 mmol) in the presence of sodium bicarbonate (0.080 g, 0.949 mmol) and tetrakis(triphenylphosphine)palladium (0) (0.027 mg, 0.024 mmol) to afford the title compound (0.098 g). Yield: 63%.

$^1$H NMR (300 MHz, CDCl$_3$): δ 7.36-7.23 (m, 3H), 7.18-7.15 (m, 2H), 7.02 (d, J=8.4 Hz, 2H), 6.70 (d, J=8.4 Hz, 2H), 4.31 (s, 2H), 3.65 (s, 3H), 2.57-2.47 (m, 5H), 2.32-2.27 (m, 2H), 1.94-1.84 (m, 2H), 1.71 (s, 2H), 1.59-1.54 (m, 7H); Mass (m/z): 415 (M+23).

Step 19b

Synthesis of 4-(4-((2-phenylcyclooct-1-en-1-yl)methoxy)phenyl)butanoic Acid The title compound was prepared in an analogous manner as in step 1c of Example 1 involving reaction of the compound obtained in step 19a, methyl 4-(4-((2-phenylcyclooct-1-en-1-yl)methoxy)phenyl)butanoate (0.090 g, 0.229 mmol) with LiOH.H$_2$O (0.917 mL, 1.37 mmol) to afford the title compound (0.080 g). Yield: 92%

$^1$H NMR (300 MHz, CDCl$_3$): δ 7.33-7.29 (m, 3H), 7.18-7.15 (m, 2H), 7.03 (d, J=8.4 Hz, 2H), 6.70 (d, J=8.4 Hz, 2H), 4.31 (s, 2H), 2.60-2.48 (m, 6H), 2.34 (t, J=7.2 Hz, 14.7 Hz, 2H), 1.93-1.88 (m, 2H), 1.71 (s, 2H), 1.60 (s, 6H).

Example 20

Synthesis of 4-(4-((2-(4-cyclopropylphenyl)cyclooct-1-en-1-yl)methoxy)phenyl) butanoic Acid

Step 20a

Synthesis of methyl 4-(4-((2-(4-cyclopropylphenyl)cyclooct-1-en-1-yl)methoxy)phenyl)butanoate The title compound was prepared in an analogous manner as in step 1b of Example 1 involving the reaction of methyl 4-(4-((2-bromocyclooct-1-en-1-yl)methoxy)phenyl)butanoate (0.063 g, 0.159 mmol) with 4-cyclopropylphenyl boronic acid (0.039 g, 0.239 mmol) in the presence of sodium bicarbonate (0.033 g, 0.398 mmol) and tetrakis(triphenylphosphine)palladium(0) (0.005 mg, 0.0048 mmol) to afford the title compound (0.029 g). Yield: 42%

$^1$H NMR (300 MHz, CDCl$_3$): δ 7.08-7.00 (m, 6H), 6.72 (d, J=8.4 Hz, 2H), 4.33 (s, 2H), 3.66 (s, 3H), 2.59-2.47 (m, 6H), 2.31 (t, J=7.5, 15 Hz, 2H), 1.93-1.85 (m, 3H), 1.71 (s, 2H), 1.58-1.54 (m, 5H), 1.27 (s, 1H), 0.99-0.93 (s, 2H), 0.72-0.69 (m, 2H); Mass (m/z): 455 (M+23).

Step 20b

Synthesis of 4-(4-((2-(4-cyclopropylphenyl)cyclooct-1-en-1-yl)methoxy)phenyl) butanoic Acid The title compound was prepared in an analogous manner as in step 1c of Example 1 involving reaction of the compound obtained in step 20a, methyl 4-(4-((2-(4-cyclopropylphenyl)cyclooct-1-en-1-yl)methoxy)phenyl)butanoate (0.025 g, 0.058 mmol) with LiOH.H$_2$O (0.231 mL, 0.347 mmol) to afford the title compound (0.020 g). Yield: 83%

$^1$H NMR (300 MHz, CDCl$_3$): δ 12.01 (s, 1H), 7.03-6.98 (m, 6H), 6.66 (d, J=8.4 Hz, 2H), 4.27 (s, 2H), 2.39 (s, 4H), 2.16 (t, J=7.2, 14.7 Hz, 2H), 1.98-1.87 (m, 1H), 1.73-1.68 (m, 3H), 1.53-1.45 (m, 6H), 1.23-1.16 (m, 2H), 0.92-0.90 (s, 2H), 0.85 (s, 1H), 0.65-0.63 (m, 2H); Mass (m/z): 441 (M+23).

Example 21

Synthesis of 4-(4-((2-(4-(1-cyanocyclopropyl)phenyl)cyclohept-1-en-1-yl)methoxy)phenyl) butanoic Acid

Step 21a

Synthesis of methyl 4-(4-((2-(4-(1-cyanocyclopropyl)phenyl)cyclohept-1-en-1-yl)methoxy)phenyl) butanoate The title compound was prepared in an analogous manner as in step 1b of Example 1 involving the reaction of methyl 4-(4-((2-bromocyclohept-1-en-1-yl)methoxy)phenyl)butanoate (0.150 g, 0.393 mmol) with (4-(1-cyanocyclopropyl)phenyl)boronic acid (0.110 g, 0.590 mmol) in presence of sodium bicarbonate (0.083 g, 0.983 mmol) and tetrakis(triphenylphosphine)palladium(0) (0.023 mg, 0.020 mmol) to afford the title compound (0.074 g). Yield: 42%

$^1$H NMR (300 MHz, DMSO-$d_6$): δ 7.28-7.25 (d, J=8.1 Hz, 2H), 7.17-7.14 (d, J=8.4 Hz, 2H), 7.05-6.97 (m, 2H), 6.69-6.66 (d, J=8.4 Hz, 2H), 4.25 (s, 2H), 3.54 (s, 3H), 2.75-2.70 (t, 2H), 2.56-2.54 (m, 4H), 2.49-2.46 (m, 2H), 2.39-2.34 (m, 2H), 1.78-1.70 (m, 4H), 1.57-1.46 (m, 6H); Mass (m/z): 452.9 (M+23).

Step 21b

Synthesis of 4-(4-((2-(4-(1-cyanocyclopropyl)phenyl)cyclohept-1-en-1-yl)methoxy)phenyl)butanoic Acid The title compound was prepared in an analogous manner as in step 1c of Example 1 involving the reaction of the compound obtained in step 21a, methyl 4-(4-((2-(4-(1-cyanocyclopropyl)phenyl)cyclohept-1-en-1-yl)methoxy)phenyl)butanoate (0.030 g, 0.068 mmol) with LiOH.H$_2$O (0.271 mL, 0.406 mmol) to afford the title compound (0.015 g). Yield: 51%

$^1$H NMR (300 MHz, CDCl$_3$): δ 12.00 (bs, 1H), 7.29-7.28 (d, J=8.0 Hz, 2H), 7.18-7.17 (d, J=8.0 Hz, 2H), 7.03-7.01 (d, J=8.5 Hz, 2H), 6.70-6.69 (d, J=8.0 Hz, 2H), 4.27 (s, 2H), 2.48-2.45 (m, 2H), 2.40-2.39 (m, 2H), 2.18-2.15 (t, 2H), 1.75-1.73 (t, 2H), 1.72-1.69 (m, 4H), 1.52-1.50 (bt, 2H), 1.50-1.46 (m, 2H), 1.27-1.19 (m, 4H); Mass (m/z): 452.6 (M+23), 428.1 (M−1).

Example 22

Synthesis of 4-(4-((2-(p-tolyl)cyclohept-1-en-1-yl)methoxy)phenyl)butanoic Acid

Step 22a

Synthesis of methyl 4-(4-((2-(p-tolyl)cyclohept-1-en-1-yl)methoxy)phenyl)butanoate The title compound was prepared in an analogous manner as in step 1b of Example 1 involving the reaction of methyl 4-(4-((2-bromocyclohept-1-en-1-yl)methoxy)phenyl)butanoate (0.150 g, 0.393 mmol) with p-tolylboronic acid (0.080 g, 0.590 mmol) in presence of sodium bicarbonate (0.083 g, 0.983 mmol) and tetrakis(triphenylphosphine)palladium(0) (0.023 mg, 0.020 mmol) to afford the title compound (0.040 g). Yield: 26%

$^1$H NMR (300 MHz, DMSO-$d_6$): δ 7.13-7.10 (d, J=7.8 Hz, 2H), 7.04-7.01 (d, J=8.1 Hz, 4H), 6.67-6.64 (d, J=8.4 Hz, 2H), 4.26 (s, 2H), 3.54 (s, 3H), 2.75-2.70 (t, 2H), 2.56-2.50 (t, 2H), 2.38-2.34 (m, 2H), 2.26 (s, 3H), 1.77 (bs, 2H), 1.60-1.40 (bm, 5H); Mass (m/z): 401.7 (M+23).

Step 22b

Synthesis of 4-(4-((2-(p-tolyl)cyclohept-1-en-1-yl)methoxy)phenyl)butanoic Acid The title compound was prepared in an analogous manner as in step 1c of Example 1 involving the reaction of the compound obtained in step 22a, methyl 4-(4-((2-(p-tolyl)cyclohept-1-en-1-yl)methoxy)phenyl)butanoate (0.030 g, 0.076 mmol) with LiOH.H$_2$O (0.306 mL, 0.459 mmol) to afford the title compound (0.019 g). Yield: 65.7%

$^1$H NMR (300 MHz, CDCl$_3$): δ 12.03 (bs, 1H), 7.14-7.12 (d, J=7.5 Hz, 2H), 7.05-7.04 (d, J=7.5 Hz, 2H), 7.02-7.00 (d, J=8.0 Hz, 2H), 6.69-6.67 (d, J=8.0 Hz, 2H), 4.28 (s, 2H), 2.48-2.46 (m, 4H), 2.39-2.37 (t, 2H), 2.25 (s, 3H), 2.18-2.15 (t, 2H), 1.78-1.69 (m, 4H), 1.58 (bm, 2H), 1.51 (bm, 2H); Mass (m/z): 401.5 (M+23), 377.1 (M−1).

Example 23

Synthesis of 4-(4-((2-(4-cyclopropylphenyl)cyclodec-1-en-1-yl)methoxy)phenyl) butanoic Acid

Step 23a

Synthesis of methyl 4-(4-((2-(4-cyclopropylphenyl)cyclododec-1-en-1-yl)methoxy)phenyl)butanoate The title compound was prepared in an analogous manner as in step 1b of Example 1 involving the reaction of methyl 4-(4-((2-bromocyclododec-1-en-1-yl)methoxy)phenyl)butanoate (0.150 g, 0.332 mmol) with 4-cyclopropylphenylboronic acid (0.081 g, 0.498 mmol) in presence of sodium bicarbonate (0.070 g, 0.831 mmol) and tetrakistri(phenylphosphine)palladium(0) (0.023 mg, 0.020 mmol) to afford the title compound (0.055 g). Yield: 34%

$^1$H NMR (300 MHz, CDCl$_3$): δ 7.00-6.98 (m, 6H), 6.67 (d, J=8.4 Hz, 2H), 4.33 (s, 2H), 3.66 (s, 3H), 2.57-2.48 (m, 4H), 2.39-2.28 (m, 4H), 1.92-1.87 (m, 2H), 1.66 (s, 2H), 1.42 (m, 9H), 1.26 (s, 6H), 0.97-0.95 (m, 2H), 0.71-0.69 (m, 2H).

Step 23b

Synthesis of 4-(4-((2-(4-cyclopropylphenyl)cyclodec-1-en-1-yl)methoxy)phenyl) butanoic Acid The title compound was prepared in an analogous manner as in step 1c of Example 1 involving the reaction of the compound obtained in step 23a, methyl 4-(4-((2-(4-cyclopropylphenyl)cyclododec-1-en-1-yl)methoxy)phenyl)butanoate (0.050 g, 0.102 mmol) with LiOH.H$_2$O (0.409 mL, 0.614 mmol) to afford the title compound (0.045 g). Yield: 93%

$^1$H NMR (300 MHz, CDCl$_3$): δ 12.01 (s, 1H), 7.01-6.97 (m, 6H), 6.62 (d, J=8.4 Hz, 2H), 4.27 (s, 2H), 2.45 (s, 3H), 2.31 (s, 2H), 2.15 (t, J=7.5, 14.7 Hz, 2H), 1.88 (s, 1H), 1.72-1.61 (m, 4H), 1.36 (bs, 8H), 1.23-1.16 (m, 7H), 0.93-0.91 (m, 2H), 0.66-0.64 (m, 2H); Mass (m/z): 473 (m−1).

Example 24

Synthesis of 4-(4-((2-(o-tolyl)cyclopent-1-en-1-yl)methoxy)phenyl)butanoic Acid

Step 24a

Synthesis of methyl 4-(4-((2-(o-tolyl)cyclopent-1-en-1-yl)methoxy)phenyl)butanoate The title compound was prepared in an analogous manner as in step 1b of Example 1 involving the reaction of methyl 4-(4-((2-bromocyclopent-1-en-1-yl)methoxy)phenyl)butanoate (0.266 g, 0.566 mmol) with o-tolylboronic acid (0.115 g, 0.849 mmol) in presence of sodium bicarbonate (0.119 g, 1.41 mmol) and tetrakis(triphenylphosphine)palladium(0) (0.023 mg, 0.020 mmol) to afford the title compound (0.110 g). Yield: 53%

$^1$H NMR (300 MHz, CDCl$_3$): δ 7.21-7.13 (m, 3H), 7.06-7.00 (m, 3H), 6.73 (d, J=8.4 Hz, 2H), 4.36 (s, 2H), 3.67 (s, 3H), 2.67 (t, J=7.5, 15 Hz, 4H), 2.57 (t, J=7.5, 15.3 Hz, 2H), 2.31 (t, J=7.5, 15 Hz, 2H), 2.23 (s, 3H), 2.07-1.85 (m, 4H).

Step 24b

Synthesis of 4-(4-((2-(o-tolyl)cyclopent-1-en-1-yl)methoxy)phenyl)butanoic Acid The title compound was prepared in an analogous manner as in step 1c of Example 1 involving the reaction of the compound obtained in step 24a, methyl 4-(4-((2-(o-tolyl)cyclopent-1-en-1-yl)methoxy)phenyl)butanoate (0.100 mg, 0.274 mmol) with LiOH.H$_2$O (0.109 mL, 1.64 mmol) to afford the title compound (0.095 g). Yield: 99%

$^1$H NMR (300 MHz, CDCl$_3$): δ 12.10 (s, 1H), 7.20-7.16 (m, 3H), 7.04-6.99 (m, 3H), 6.70 (s, 2H), 4.29 (s, 2H), 2.61-2.59 (m, 3H), 2.50-2.44 (s, 4H), 2.18-2.13 (m, 4H), 1.98-1.92 (m, 2H), 1.73-1.68 (m, 2H).

Example 25

Synthesis of 4-(4-((2-phenylcyclopent-1-en-1-yl)methoxy)phenyl)butanoic Acid

Step 25a

Synthesis of methyl 4-(4-((2-phenylcyclopent-1-en-1-yl)methoxy)phenyl)butanoate The title compound was prepared in an analogous manner as in step 1b of Example 1 involving the reaction of methyl 4-(4-((2-bromocyclopent-1-en-1-yl)methoxy)phenyl)butanoate (0.200 g, 0.566 mmol) with phenylboronic acid (0.104 g, 0.894 mmol) in presence of sodium bicarbonate (0.119 g, 1.41 mmol) and tetrakis(triphenylphosphine)palladium(0) (0.023 mg, 0.020 mmol) to afford the title compound (0.115 g). Yield: 58%

$^1$H NMR (300 MHz, CDCl$_3$): δ 7.38-7.33 (m, 2H), 7.28-7.26 (m, 3H), 7.07 (d, J=8.4 Hz, 2H), 6.80 (d, J=8.7 Hz, 2H), 4.64 (s, 2H), 3.67 (s, 3H), 2.84 (t, J=7.5, 14.7 Hz, 2H), 2.71 (t, J=7.2, 15 Hz, 2H), 2.59 (t, J=7.2, 15 Hz, 2H), 2.32 (t, J=7.5.15 Hz, 2H), 2.05-1.87 (m, 4H).

Step 25b

Synthesis of 4-(4-((2-phenylcyclopent-1-en-1-yl)methoxy)phenyl)butanoic Acid The title compound was prepared in an analogous manner as in step 1c of Example 1 involving the reaction of the compound obtained in step 25a, methyl 4-(4-((2-phenylcyclopent-1-en-1-yl)methoxy)phenyl)butanoate (0.105 g, 0.300 mmol) with LiOH.H$_2$O (0.119 mL, 1.79 mmol) to afford the title compound (0.098 g). Yield: 97%

$^1$H NMR (300 MHz, CDCl$_3$): δ 12.03 (s, 1H), 7.37-7.35 (m, 2H), 7.29-7.27 (m, 3H), 7.06 (d, J=8.4 Hz, 2H), 6.79 (d, J=8.4 Hz, 2H), 4.61 (s, 2H), 2.79 (bs, 2H), 2.63 (bs, 2H), 2.17 (t, J=7.5, 14.7 Hz, 2H), 1.92 (t, J=7.5, 15 Hz, 2H), 1.75 (m, 2H).

Example 26

Synthesis of 4-(4-((2-(4-cyclopropylphenyl)cyclopent-1-en-1-yl)methoxy)phenyl) butanoic Acid

Step 26a

Synthesis of methyl 4-(4-((2-(4-cyclopropylphenyl)cyclopent-1-en-1-yl)methoxy)phenyl) butanoate The title compound was prepared in an analogous manner as in step 1b of Example 1 involving the reaction of methyl 4-(4-((2-bromocyclopent-1-en-1-yl)methoxy)phenyl)butanoate (0.200 g, 0.566 mmol) with (4-cyclopropylphenyl)boronic acid (0.138 g, 0.849 mmol) in presence of sodium bicarbonate (0.119 g, 1.41 mmol) and tetrakis(triphenylphosphine)palladium(0) (0.023 mg, 0.020 mmol) to afford the title compound (0.130 g). Yield: 59%

$^1$H NMR (300 MHz, CDCl$_3$): δ 7.18 (d, J=8.4 Hz, 2H), 7.11-7.04 (m, 4H), 6.80 (d, J=8.7 Hz, 2H), 4.62 (s, 2H), 3.67 (s, 3H), 2.81-2.67 (m, 4H), 2.59 (t, J=7.5, 15 Hz, 2H), 2.32 (t, J=7.2, 15 Hz, 2H), 2.03-1.87 (m, 5H), 1.00-0.94 (m, 2H), 0.73-0.72 (m, 2H).

Step 26b

Synthesis of 4-(4-((2-(4-cyclopropylphenyl)cyclopent-1-en-1-yl)methoxy)phenyl) butanoic Acid The title compound was prepared in an analogous manner as in step 1c of Example 1 involving the reaction of the compound obtained in step 26a, methyl 4-(4-((2-(4-cyclopropylphenyl)cyclopent-1-en-1-yl)methoxy)phenyl) butanoate (0.120 g, 0.307 mmol) with LiOH.H$_2$O (0.122 mL, 1.84 mmol) to afford the title compound (0.090 g). Yield: 77%.

$^1$H NMR (300 MHz, CDCl$_3$): δ 12.07 (s, 1H), 7.17-7.14 (m, 2H), 7.07-7.03 (m, 4H), 6.80 (d, J=8.4 Hz, 2H), 4.59 (s, 2H), 2.75 (bs, 2H), 2.61 (bs, 2H), 2.49 (s, 2H), 2.17 (t, J=7.2, 14.7 Hz, 2H), 1.98-1.87 (m, 2H), 1.72 (t, J=7.5 Hz, 15 Hz, 2H), 0.94-0.91 (m, 2H), 0.66-0.64 (m, 2H).

Example 27

Synthesis of 4-(4-((2-(4-cyclopropylphenyl)cyclohept-1-en-1-yl)methoxy)phenyl)butanoic Acid

Step 27a

Synthesis of methyl 4-(4-((2-(4-cyclopropylphenyl)cyclohept-1-en-1-yl)methoxy)phenyl)butanoate The title compound was prepared in an analogous manner as in step 1b of Example 1 involving the reaction of methyl 4-(4-((2-bromocyclohept-1-en-1-yl)methoxy)phenyl)butanoate. (0.150 g, 0.393 mmol) with (4-cyclopropylphenyl) boronic acid (0.096 g, 0.590 mmol) in presence of sodium bicarbonate (0.083 g, 0.983 mmol) and tetrakis(triphenylphosphine)palladium(0) (0.023 mg, 0.020 mmol) to afford the title compound (0.080 g). Yield: 48%

$^1$H NMR (300 MHz, DMSO-d$_6$): δ 7.28-7.25 (d, J=8.1 Hz, 2H), 7.17-7.14 (d, J=8.4 Hz, 2H), 7.05-6.97 (m, 2H), 6.69-6.66 (d, J=8.4 Hz, 2H), 4.25 (s, 2H), 3.54 (s, 3H), 2.75-2.70 (t, 2H), 2.56-2.50 (t, 2H), 2.49-2.46 (m, 2H), 2.39-2.34 (m, 2H), 1.78-1.70 (m, 4H), 1.57-1.46 (m, 6H); Mass (m/z): 452.9 (M+23)

Step 27b

Synthesis of 4-(4-((2-(4-cyclopropylphenyl)cyclohept-1-en-1-yl)methoxy)phenyl)butanoic acid The title compound was prepared in an analogous manner as in step 1c of Example 1 involving the reaction of the compound obtained in step 27a, methyl 4-(4-((2-(4-cyclopropylphenyl)cyclohept-1-en-1-yl)methoxy)phenyl)butanoate (0.050 g, 0.119 mmol) with LiOH.H$_2$O (0.478 mL, 0.717 mmol) to afford the title compound (0.030 g). Yield: 62%

$^1$H NMR (300 MHz, CDCl$_3$): δ 12.01 (bs, 1H), 7.04-7.00 (m, 6H), 6.96-6.67 (d, J=8.5 Hz, 2H), 4.28 (s, 2H), 2.50-2.46 (m, 2H), 2.38-2.36 (m, 2H), 2.18-2.15 (t, 2H), 1.90-1.86 (m, 1H), 1.78-1.75 (m, 2H), 1.73-1.70 (m, 2H), 1.57 (bt, 2H), 1.50 (bt, 2H), 1.20-1.17 (m, 2H), 0.94-0.90 (m, 2H), 0.66-0.63 (m, 2H); Mass (m/z): 427.2 (M+23), 403 (M−1).

Example 28

Synthesis of 4-(4-((2-(m-tolyl)cyclohept-1-en-1-yl)methoxy)phenyl)butanoic Acid

Step 28a

Synthesis of methyl 4-(4-((2-(m-tolyl)cyclohept-1-en-1-yl)methoxy)phenyl)butanoate The title compound was prepared in an analogous manner as in step 1b of Example 1 involving the reaction of methyl 4-(4-((2-bromocyclohept-1-en-1-yl)methoxy)phenyl)butanoate. (0.200 g, 0.525 mmol) with m-tolylboronic acid (0107 g, 0.787 mmol) in presence of sodium bicarbonate (0.110 g, 1.311 mmol) and tetrakis(triphenylphosphine)palladium(0) (0.030 mg, 0.026 mmol) to afford the title compound (0.125 g). Yield: 60.7%

$^1$H NMR (300 MHz, DMSO-d$_6$): δ 7.21-7.16 (m, 2H), 7.05-6.95 (m, 4H), 6.72-6.69 (d, J=8.7 Hz, 2H), 4.31 (s, 2H), 3.66 (s, 3H), 2.57-2.44 (m, 4H), 2.47-2.44 (m, 2H), 2.31-2.28 (m, 5H), 1.95-1.82 (m, 4H), 1.64 (m, 2H), 1.58 (m, 2H); Mass (m/z): 415.2 (M+23)

Step 28b

Synthesis of 4-(4-((2-(m-tolyl)cyclohept-1-en-1-yl)methoxy)phenyl)butanoic Acid The title compound was prepared in an analogous manner as in step 1c of Example 1 involving the reaction of the compound obtained in step 28a, methyl 4-(4-((2-(m-tolyl)cyclohept-1-en-1-yl)methoxy)phenyl)butanoate (0.100 g, 0.255 mmol) with LiOH.H$_2$O (0.101 mL, 1.529 mmol) to afford the title compound (0.071 g). Yield: 73.6%

$^1$H NMR (300 MHz, DMSO-d$_6$): δ 11.98 (bs, 1H), 7.22-7.17 (m, 2H), 7.05-7.04 (d, J=7.5 Hz, 2H), 7.01-6.99 (m, 4H), 6.69-6.66 (d, J=8.4 Hz, 2H), 4.26 (s, 2H), 2.48-2.36 (m, 4H), 2.24 (s, 3H), 2.17-2.13 (t, 2H), 1.76-1.68 (m, 4H), 1.58 (bm, 2H), 1.51 (bm, 2H), 1.22-1.16 (m, 2H); Mass (m/z): 401.2 (M+23), 377.0 (M−1).

Example 29

Synthesis of 4-(4-((2-(o-tolyl)cyclohept-1-en-1-yl)methoxy)phenyl)butanoic Acid

Step 29a

Synthesis of methyl 4-(4-((2-(m-tolyl)cyclohept-1-en-1-yl)methoxy)phenyl)butanoate The title compound was prepared in an analogous manner as in step 1b of Example 1 involving the reaction of methyl 4-(4-((2-bromocyclohept-1-en-1-yl)methoxy)phenyl)butanoate (0.200 g, 0.525 mmol) with o-tolylboronic acid (0.107 g, 0.787 mmol) in presence of sodium bicarbonate (0.110 g, 1.311 mmol) and tetrakis(triphenylphosphine)palladium(0) (0.030 mg, 0.026 mmol) to afford the title compound (0.180 g). Yield: 87%

$^1$H NMR (300 MHz, DMSO-d$_6$): δ 7.16-7.11 (m, 4H), 7.01-6.98 (d, J=8.7 Hz, 2H), 6.67-6.64 (d, J=8.4 Hz, 2H), 4.15 (s, 2H), 3.65 (s, 3H), 2.57-2.48 (m, 4H), 2.45-2.38 (m, 4H), 2.21 (s, 3H), 1.91-1.40 (m, 8H); Mass (m/z): 415.3 (M+23).

Step 29b

Synthesis of 4-(4-((2-(o-tolyl)cyclohept-1-en-1-yl)methoxy)phenyl)butanoic Acid The title compound was prepared in an analogous manner as in step 1c of Example 1 involving the reaction of the compound obtained in step 29a, methyl 4-(4-((2-(o-tolyl)cyclohept-1-en-1-yl)methoxy)phenyl)butanoate (0.165 g, 0.255 mmol) with LiOH.H$_2$O (0.168 mL, 2.52 mmol) to afford the title compound (0.089 g). Yield: 56%

$^1$H NMR (300 MHz, DMSO-d$_6$): δ12.10 (bs, 1H), 7.18-7.11 (m, 4H), 6.99-6.67 (d, J=8.1 Hz, 2H), 6.63-6.60 (d, J=8.4 Hz, 2H), 4.09 (s, 2H), 2.48-2.36 (m, 4H), 2.29-2.13 (t, 7H), 1.76-1.40 (m, 8H); Mass (m/z): 401.2 (M+23), 377.0 (M−1).

Example 30

Synthesis of 4-(4-((2-phenylcyclododec-1-en-1-yl)methoxy)phenyl)butanoic Acid

Step 30a

Synthesis of methyl 4-(4-((2-phenylcyclododec-1-en-1-yl)methoxy)phenyl)butanoate The title compound was prepared in an analogous manner as in step 1b of Example 1 involving the reaction of methyl 4-(4-((2-bromocyclododec-1-en-1-yl)methoxy)phenyl)butanoate. (0.150 g, 0.332 mmol) with phenylboronic acid (0.068 g, 0.498 mmol) in presence of sodium bicarbonate (0.070 g, 0.83 mmol) and tetrakis(triphenylphosphine)palladium(0) (0.019 mg, 0.017 mmol) to afford the title compound (0.075 g). Yield: 50%

$^1$H NMR (300 MHz, DMSO-d$_6$): 7.33-7.23 (m, 3H), 7.12-1.10 (d, J=6.9 Hz, 2H), 7.00-6.97 (d, J=8.4 Hz, 2H), 6.65-6.63 (d, J=8.7 Hz, 2H), 4.31 (s, 2H), 2.56-2.38 (m, 6H), 2.32-2.27 (m, 2H) 1.91-1.86 (t, 2H), 1.66 (m, 2H), 1.40-1.20 (m, 14H); Mass: 461.3 (M+23).

Step 30b

Synthesis of 4-(4-((2-phenylcyclododec-1-en-1-yl)methoxy)phenyl)butanoic Acid The title compound was prepared in an analogous manner as in step 1c of Example 1 involving the reaction of the compound obtained in step 30a, methyl 4-(4-((2-phenylcyclododec-1-en-1-yl)methoxy)phenyl)butanoate (0.050 g, 0.119 mmol) with LiOH.H$_2$O (0.446 mL, 0.669 mmol) to afford the title compound (0.025 g). Yield: 51.6%

$^1$H NMR (300 MHz, DMSO-d$_6$): δ 12.01 (bs, 1H), 7.36-7.12 (m, 3H), 7.15-1.12 (d, J=7.8 Hz, 2H), 6.99-6.67 (d, J=8.1 Hz, 2H), 6.61-6.59 (d, J=8.4 Hz, 2H), 4.26 (s, 2H), 2.49-2.42 (m, 2H), 2.33 (m, 2H) 2.17-2.13 (t, 2H), 1.72-1.63 (m, 4H), 1.50-1.17 (m, 16H); Mass: 457.2 (M+23), 433.0 (M−1).

Example 31

Synthesis of 4-(4-((-2-(p-tolyl)cyclododec-1-en-1-yl)methoxy)phenyl)butanoic Acid

Step 31a

Synthesis of Methyl 4-(4-((-2-(p-tolyl)cyclododec-1-en-1-yl)methoxy)phenyl)butanoate The title compound was prepared in an analogous manner as in step 1b of Example 1 involving the reaction of methyl 4-(4-((2-bromocyclododec-1-en-1-yl)methoxy)phenyl)butanoate (0.150 g, 0.332 mmol) with p-tolylboronic acid (0.068 g, 0.498 mmol) in presence of sodium bicarbonate (0.070 g, 0.831 mmol) and tetrakis(triphenylphosphine)palladium(0) (0.019 mg, 0.017 mmol) to afford the title compound (0.095 g). Yield: 61.8%

$^1$H NMR (300 MHz, DMSO-d$_6$): δ 7.13-7.10 (d, J=7.8 Hz, 2H), 7.01-6.97 (m, 4H), 6.66-6.63 (d, J=8.7 Hz, 2H), 4.33 (s, 2H), 3.65 (s, 3H), 2.56-2.45 (m, 4H), 2.45-2.28 (m, 7H), 1.91-1.86 (m, 2H), 1.74-1.69 (m, 4H), 1.40-1.26 (m, 12H); Mass: 485 (M+23).

Step 31b

Synthesis of 4-(4-((-2-(p-tolyl)cyclododec-1-en-1-yl)methoxy)phenyl)butanoic Acid The title compound was prepared in an analogous manner as in step 1c of Example 1 involving the reaction of the compound obtained in step 31a, methyl 4-(4-((-2-(p-tolyl)cyclododec-1-en-1-yl)methoxy)phenyl)butanoate (0.080 g, 0.173 mmol) with LiOH.H$_2$O (0.691 mL, 1.037 mmol) to afford the title compound (0.045 g). Yield: 58%

$^1$H NMR (300 MHz, DMSO-d$_6$): δ 12.01 (bs, 1H), 7.15-7.12 (d, J=7.8 Hz, 2H), 7.03-7.01 (d, J=8.1 Hz, 2H), 6.99-6.97 (d, J=8.4 Hz, 2H), 6.62-6.59 (d, J=8.4 Hz, 2H), 4.27 (s, 2H), 2.49-2.45 (m, 2H), 2.40-2.28 (m, 5H), 2.18-2.13 (t, 2H), 1.72-1.67 (m, 4H), 1.50-1.17 (m, 16H); Mass (m/z): 471.3 (M+23), 447.1 (M−1).

Example 32

4-(4-((2-(2,3-dihydrobenzofuran-5-yl)cyclohept-1-en-1-yl)methoxy)phenyl)butanoic Acid

Step 32a

Synthesis of methyl 4-(4-((2-(2,3-dihydrobenzofuran-5-yl)cyclohept-1-en-1-yl)methoxy) phenyl)butanoate The title compound was prepared in an analogous manner as in step 1b of Example 1 involving the reaction of methyl 4-(4-((2-bromocyclohept-1-en-1-yl)methoxy)phenyl)butanoate (0.150 g, 0.393 mmol) with (2,3-dihydrobenzofuran-5-yl)boronic acid (0.097 g, 0.590 mmol) in presence of sodium bicarbonate (0.083 g, 0.983 mmol) and tetrakis(triphenylphosphine)palladium(0) (0.023 mg, 0.020 mmol) to afford the title compound (0.110 g). Yield: 66.5%

Step 32b

Synthesis of 4-(4-((2-(2,3-Dihydrobenzofuran-5-yl)cyclohept-1-en-1-yl)methoxy)phenyl) butanoic Acid The title compound was prepared in an analogous manner as in step 1c of Example 1 involving the reaction of the compound obtained in step 32a, methyl 4-(4-((2-(2,3-dihydrobenzofuran-5-yl)cyclohept-1-en-1-yl)methoxy)phenyl)butanoate (0.100 g, 0.238 mmol) with LiOH.H$_2$O (0.951 mL, 1.427 mmol), to afford the title compound (0.056 g). Yield: 58%

$^1$H NMR (300 MHz, DMSO-d$_6$): δ 11.96 (bs, 1H), 7.02-7.00 (m, 3H), 6.86-6.83 (d, J=8.4 Hz, 1H), 6.69-6.67 (m, 3H), 4.52-4.46 (t, 2H), 4.30 (s, 2H), 3.15-3.09 (t, 2H), 2.48-2.44 (m, 4H), 2.37 (m, 2H), 2.18-2.13 (t, 2H), 1.74-1.69 (m, 4H), 1.56-1.49 (m, 4H).

Example 33

Synthesis of 4-(4-((2-(2,3-dihydrobenzofuran-5-yl)cyclohex-1-en-1-yl)methoxy)phenyl)butanoic Acid

Step 33a

Synthesis of methyl 4-(4-((2-(2,3-dihydrobenzofuran-5-yl)cyclohex-1-en-1-yl)methoxy) phenyl)butanoate The title compound was prepared in an analogous manner as in step 1b of Example 1 involving the reaction of methyl 4-(4-((2-bromocyclohex-1-en-1-yl)methoxy)phenyl)butanoate. (0.170 g, 0.463 mmol) with (2,3-dihydrobenzofuran-5-yl)boronic acid (0.114 g, 0.694 mmol) in presence of sodium bicarbonate (0.097 g, 1.15 mmol) and tetrakis(triphenylphosphine)palladium(0) (0.027 mg, 0.023 mmol) to afford the title compound (0.120 g). Yield: 64%.

Step 33b

Synthesis of 4-(4-((2-(2,3-dihydrobenzofuran-5-yl)cyclohex-1-en-1-yl)methoxy)phenyl) butanoic Acid The title compound was prepared in an analogous manner as in step 1c of Example 1 involving the reaction of the compound obtained in step 33a, methyl 4-(4-((2-(2,3-dihydrobenzofuran-5-yl)cyclohex-1-en-1-yl)methoxy) phenyl)butanoate (0.050 g, 0.119 mmol) with LiOH.H$_2$O (0.446 mL, 0.669 mmol) to afford the title compound (0.110 g). Yield: 66.5%

$^1$H NMR (300 MHz, DMSO-d$_6$): δ 12.02 (bs, 1H), 7.04-7.01 (m, 3H), 6.90-6.87 (d, J=8.4 Hz, 1H), 6.73-6.66 (m, 3H), 4.51-4.45 (t, 2H), 4.26 (s, 2H), 3.13-3.08 (t, 2H), 2.48-2.44 (m, 2H), 2.19-2.14 (m, 6H), 1.74-1.66 (m, 6H); Mass (m/z): 415.2 (M+23), 391.0 (M−1).

Example 34

Synthesis of 4-(4-((2-(2,3-dihydrobenzofuran-5-yl)cyclopent-1-en-1-yl)methoxy)phenyl)butanoic Acid Step 34a Synthesis of methyl 4-(4-((2-(2,3-dihydrobenzofuran-5-yl)cyclopent-1-en-1-yl)methoxy) phenyl)butanoate The title compound was prepared in an analogous manner as in step 1b of Example 1 involving the reaction of methyl 4-(4-((2-bromocyclopent-1-en-1-yl)methoxy)phenyl)butanoate (0.200 g, 0.566 mmol) with (2,3-dihydrobenzofuran-5-yl)boronic acid (0.139 g, 0.849 mmol) in presence of sodium bicarbonate (0.119 g, 1.415 mmol) and tetrakis(triphenylphosphine)palladium(0) (0.033 mg, 0.028 mmol) to afford the title compound (0.110 g). Yield: 49.5%

Step 34b

Synthesis of 4-(4-((2-(2,3-dihydrobenzofuran-5-yl)cyclopent-1-en-1-yl)methoxy)phenyl) butanoic Acid The title compound was prepared in an analogous manner as in step 1c of Example 1 involving the reaction of the compound obtained in step 34a, methyl 4-(4-((2-(2,3-dihydrobenzofuran-5-yl)cyclopent-1-en-1-yl)methoxy)phenyl)butanoate (0.080 g, 0.204 mmol) with LiOH.H$_2$O (0.815 mL, 1.22 mmol), to afford the title compound (0.054 g). Yield: 70%

$^1$H NMR (300 MHz, DMSO-d$_6$): δ 11.89 (bs, 1H), 7.15 (bs, 1H), 7.06-6.99 (m, 3H), 6.79-6.73 (m, 3H), 4.59 (bs, 2H), 4.54-4.48 (t, 2H), 3.18-3.12 (t, 2H), 2.73 (bt, 2H), 2.59 (bt, 2H), 2.50-2.46 (m, 2H), 2.19-2.15 (t, 2H), 1.90-1.86 (t, 2H), 1.75-1.70 (t, 2H); Mass (m/z): 401.2 (M+23), 377.0 (M−1).

Example 35

Synthesis of 4-(4-((2-(p-tolyl)cyclopent-1-en-1-yl)methoxy)phenyl)butanoic Acid

Step 35a

Synthesis of methyl 4-(4-((2-(p-tolyl)cyclopent-1-en-1-yl)methoxy)phenyl)butanoate The title compound was prepared in an analogous manner as in step 1b of Example 1 involving the reaction of methyl 4-(4-((2-bromocyclopent-1-en-1-yl)methoxy)phenyl)butanoate (0.200 g, 0.566 mmol) with p-tolylboronic acid (0.115 g, 0.849 mmol) in presence of sodium bicarbonate (0.119 g, 1.41 mmol) and tetrakis(triphenylphosphine)palladium(0) (0.033 mg, 0.028 mmol) to afford the title compound (0.105 g). Yield: 51%

Step 35b

Synthesis of 4-(4-((2-(p-tolyl)cyclopent-1-en-1-yl)methoxy)phenyl)butanoic Acid

The title compound was prepared in an analogous manner as in step 1c of Example 1 involving the reaction of the compound obtained in step 35a, methyl 4-(4-((2-(p-tolyl)cyclopent-1-en-1-yl)methoxy)phenyl)butanoate (0.095 g, 0.261 mmol) with LiOH.H$_2$O (0.104 mL, 1.56 mmol) to afford the title compound (0.060 g). Yield: 66%

$^1$H NMR (300 MHz, DMSO-d$_6$): δ 12.03 (bs, 1H), 7.17 (bs, 4H), 7.06-7.03 (d, J=8.4 Hz, 2H), 6.79-6.76 (d, J=8.4 Hz, 2H), 4.59 (s, 2H), 2.75 (bt, 2H), 2.61 (bt, 2H), 2.50-2.46 (m, 2H), 2.29 (s, 3H), 2.19-2.14 (t, 2H), 1.92-1.87 (t, 2H), 1.75-1.70 (t, 2H); Mass (m/z): 349.0 (M−1).

Example 36

Synthesis of 4-(4-((2-(m-tolyl)cyclopent-1-en-1-yl)methoxy)phenyl)butanoic Acid

Step 36a

Synthesis of methyl 4-(4-((2-(m-tolyl)cyclopent-1-en-1-yl)methoxy)phenyl)butanoate The title compound was prepared in an analogous manner as in step 1b of Example 1 involving the reaction of methyl 4-(4-((2-bromocyclopent-1-en-1-yl)methoxy)phenyl)butanoate (0.200 g, 0.566 mmol) with m-tolylboronic acid (0.115 g, 0.849 mmol) in presence of sodium bicarbonate (0.119 g, 1.41 mmol) and tetrakis(triphenylphosphine)palladium(0) (0.033 mg, 0.028 mmol) to afford the title compound (0.055 g). Yield: 27%

Step 36b

Synthesis of 4-(4-((2-(m-tolyl)cyclopent-1-en-1-yl)methoxy)phenyl)butanoic Acid

The title compound was prepared in an analogous manner as in step 1c of Example 1 involving the reaction of the compound obtained in step 36a, methyl 4-(4-((2-(m-tolyl)cyclopent-1-en-1-yl)methoxy)phenyl)butanoate (0.050 g, 0.137 mmol) with LiOH.H$_2$O (0.549 mL, 0.823 mmol) to afford the title compound (0.034 g). Yield: 70%

$^1$H NMR (300 MHz, DMSO-d$_6$): δ 12.01 (bs, 1H), 7.27-7.22 (m, 1H), 7.08-7.03 (m, 5H), 6.79-6.76 (d, J=8.4 Hz, 2H), 4.59 (s, 2H), 2.76 (bt, 2H), 2.62 (bt, 2H), 2.49-2.46 (m, 2H), 2.27 (s, 3H), 2.19-2.14 (t, 2H), 1.93-1.88 (t, 2H), 1.75-1.70 (t, 2H); Mass (m/z): 349.0 (M−1).

Example 37

4-(4-((2-(5-methylthiophen-2-yl)cyclohept-1-en-1-yl)methoxy)phenyl)butanoic Acid Step 37a Synthesis of methyl 4-(4-((2-(5-methylthiophen-2-yl)cyclohept-1-en-1-yl)methoxy)phenyl) butanoate The title compound was prepared in an analogous manner as in step 1b of Example 1 involving the reaction of methyl 4-(4-((2-bromocyclohept-1-en-1-yl)methoxy)phenyl)butanoate. (0.200 g, 0.525 mmol) with (5-methylthiophen-2-yl)boronic acid (0.261 g, 1.83 mmol) in presence of sodium bicarbonate (0.110 g, 1.31 mmol) and tetrakis(triphenylphosphine)palladium(0) (0.030 mg, 0.026 mmol) to afford the title compound (0.090 g). Yield: 43%

Step 37b

Synthesis of 4-(4-((2-(5-methylthiophen-2-yl)cyclohept-1-en-1-yl)methoxy)phenyl)butanoic Acid The title compound was prepared in an analogous manner as in step 1c of Example 1 involving the reaction of the compound obtained in step 37a, methyl 4-(4-((2-(5-methylthiophen-2-yl)cyclohept-1-en-1-yl)methoxy)phenyl)butanoate (0.080 g, 0.201 mmol) with LiOH.H$_2$O (0.803 mL, 1.20 mmol) to afford the title compound (0.035 g). Yield: 45%

$^1$H NMR (300 MHz, DMSO-d$_6$): δ 11.97 (s, 1H), 7.05-7.02 (d, J=8.1 Hz, 2H), 6.75-6.73 (d, J=8.1 Hz, 2H), 6.65 (bs, 2H), 4.49 (s, 2H), 2.55-2.50 (m, 2H), 2.50-2.46 (m, 2H), 2.40 (bs, 5H), 2.19-2.14 (t, 2H), 1.75-1.73 (m, 4H), 1.53-1.46 (m, 4H); Mass (m/z): 383.0 (M−1), 407.2 (M+23).

Example 38

Synthesis of 4-(4-((2-(pyridin-3-yl)cyclohept-1-en-1-yl)methoxy)phenyl)butanoic Acid Step 38a Synthesis of methyl 4-(4-((2-(pyridin-3-yl)cyclohept-1-en-1-yl)methoxy)phenyl)butanoate The title compound was prepared in an analogous manner as in step 1b of Example 1 involving the reaction of methyl 4-(4-((2-bromocyclohept-1-en-1-yl)methoxy)phenyl)butanoate. (0.100 g, 0.262 mmol) with pyridin-3-yl-boronic acid (0.048 g, 0.393 mmol) in presence of sodium bicarbonate (0.055 g, 0.656 mmol) and s tetrakis(triphenylphosphine)palladium(0) (0.015 mg, 0.013 mmol) to afford the title compound (0.059 g). Yield: 59%

Step 38b

Synthesis of 4-(4-((2-(pyridin-3-yl)cyclohept-1-en-1-yl)methoxy)phenyl)butanoic Acid The title compound was prepared in an analogous manner as in step 1c of Example 1 involving the reaction of the compound obtained in step 38a, methyl 4-(4-((2-(pyridin-3-yl)cyclohept-1-en-1-yl)methoxy)phenyl)butanoate (0.049 g, 0.129 mmol) with LiOH.H$_2$O (0.516 mL, 0.775 mmol) to afford the title compound (0.035 g). Yield: 74%

$^1$H NMR (300 MHz, DMSO-d$_6$): δ 12.04 (s, 1H), 8.45-8.36 (m, 2H), 7.60 (d, J=7.8 Hz, 1H), 7.39-7.34 (m, 1H), 7.03 (d, J=8.4 Hz, 2H), 6.71 (d, J=8.4 Hz, 2H), 4.25 (s, 2H), 2.45 (s, 4H), 2.16 (t, J=7.2 Hz, 14.7 Hz, 2H), 1.80 (s, 4H), 1.74-1.69 (m, 4H), 1.23-1.16 (m, 2H).

Example 39

Synthesis of 4-(4-((2-(4-methoxyphenyl)cyclohept-1-en-1-yl)methoxy)phenyl)butanoic Acid Step 39a Synthesis of methyl 4-(4-((2-(4-methoxyphenyl)cyclohept-1-en-1-yl)methoxy)phenyl) butanoate The title compound was prepared in an analogous manner as in step 1b of Example 1 involving the reaction of methyl 4-(4-((2-bromocyclohept-1-en-1-yl)methoxy)phenyl)butanoate. (0.100 g, 0.262 mmol) with (4-methoxyphenyl) boronic acid (0.060 g, 0.393 mmol) in presence of sodium bicarbonate (0.055 g, 0.656 mmol) and tetrakis(triphenylphosphine)palladium(0) (0.030 mg, 0.026 mmol) to afford the title compound (0.060 g). Yield: 56%.

Step 39b

Synthesis of 4-(4-((2-(4-methoxyphenyl)cyclohept-1-en-1-yl)methoxy)phenyl)butanoic Acid The title compound was prepared in an analogous manner as in step 1c of Example 1 involving the reaction of the compound obtained in step 39a, methyl 4-(4-((2-(4-methoxyphenyl)cyclohept-1-en-1-yl)methoxy)phenyl) butanoate (0.055 g, 0.135 mmol) with LiOH.H$_2$O (0.539 mL, 0.808 mmol) to afford the title compound (0.050 g). Yield: 94%.

$^1$H NMR (300 MHz, DMSO-d$_6$): δ 12.02 (s, 1H), 7.09-6.99 (m, 4H), 6.89 (d, J=8.7 Hz, 2H), 6.69 (d, J=8.7 Hz, 2H), 4.29 (s, 2H), 3.73 (s, 3H), 2.35 (m, 4H), 2.16 (t, J=7.2 Hz, 14.7 Hz, 2H), 1.76-1.69 (m, 4H), 1.57-1.50 (m, 4H); 2.50 (2H).

Example 40

Synthesis of 4-(4-((2-(6-methoxypyridin-3-yl)cyclohept-1-en-1-yl)methoxy)phenyl)butanoic Acid Step 40a Synthesis of methyl 4-(4-((2-(6-methoxypyridin-3-yl)cyclohept-1-en-1-yl)methoxy)phenyl) butanoate The title compound was prepared in an analogous manner as in step 1b of Example 1 involving the reaction of methyl 4-(4-((2-bromocyclohept-1-en-1-yl)methoxy)phenyl)butanoate (0.100 g, 0.262 mmol) with (6-methoxypyridin-3-yl)boronic acid (0.060 g, 0.393 mmol) in presence of sodium bicarbonate (0.055 g, 0.656 mmol) and tetrakis(triphenylphosphine)palladium(0) (0.030 mg, 0.026 mmol) to afford the title compound (0.070 g). Yield: 65%

Step 40b

Synthesis of 4-(4-((2-(6-methoxypyridin-3-yl)cyclohept-1-en-1-yl)methoxy)phenyl)butanoic Acid The title compound was prepared in an analogous manner as in step 1c of Example 1 involving the reaction of the compound obtained in step 40a, methyl 4-(4-((2-(6-methoxypyridin-3-yl)cyclohept-1-en-1-yl)methoxy)phenyl) butanoate (0.065 g, 0.159 mmol) with LiOH.H$_2$O (0.423 mL, 0.635 mmol) to afford the title compound (0.059 g). Yield: 94%

$^1$H NMR (300 MHz, DMSO-d$_6$): δ 12.02 (s, 1H), 7.93 (s, 1H), 7.54 (d, J=8.4 Hz, 1H), 7.04 (d, J=8.1 Hz, 2H), 6.82 (d, J=8.7 Hz, 1H), 6.72 (m, 2H), 4.28 (s, 2H), 3.82 (s, 3H), 2.16-2.14 (m, 2H), 1.77-1.69 (m, 4H), 1.58 (s, 4H), 1.23-1.17 (m, 2H); 2.50 (4H).

Example 41

4-(4-((2-(bicyclo[4.2.0]octa-1(6),2,4-trien-3-yl)cyclohept-1-en-1-yl)methoxy)phenyl) butanoic Acid

Step 41a

Synthesis of methyl 4-(4-((2-(bicyclo[4.2.0]octa-1(6),2,4-trien-3-yl)cyclohept-1-en-1-yl)methoxy)phenyl)butanoate The title compound was prepared in an analogous manner in step 1b of Example 1 involving the reaction of methyl 4-(4-((2-bromocyclohept-1-en-1-yl)methoxy)phenyl)butanoate. (0.150 g, 0.393 mmol) with bicyclo[4.2.0]octa-1(6),2,4-trien-3-ylboronic acid (0.087 g, 0.590 mmol) in presence of sodium bicarbonate (0.083 g, 0.983 mmol) and tetrakis(triphenylphosphine)palladium(0) (0.023 mg, 0.020 mmol) to afford the title compound (0.120 g). Yield: 75%

$^1$H NMR (300 MHz, CDCl$_3$): δ 7.76-7.73 (m, 2H), 7.21 (d, J=8.4 Hz, 1H), 7.07-6.99 (m, 2H), 6.70-6.68 (m, 2H), 4.36 (s, 2H), 3.66 (s, 3H), 2.85 (s, 3H), 2.65-2.49 (m, 6H), 2.33-2.28 (m, 2H), 1.92-1.87 (m, 4H), 1.69 (s, 2H), 1.60 (s, 3H). Mass (m/z): 427 (M+23).

Step 41b

Synthesis of 4-(4-((2-(bicyclo[4.2.0]octa-1(6),2,4-trien-3-yl)cyclohept-1-en-1-yl)methoxy) phenyl) butanoic Acid The title compound was prepared in an analogous manner in step 1c of Example 1 involving the reaction of the compound obtained in step 41a, methyl 4-(4-((2-(bicyclo[4.2.0]octa-1(6),2,4-trien-3-yl)cyclohept-1-en-1-yl)methoxy)phenyl)butanoate (0.110 g, 0.272 mmol) with LiOH.H$_2$O (0.108 mL, 1.63 mmol) to afford the title compound (0.100 g). Yield: 94%

$^1$H NMR (300 MHz, DMSO-d$_6$): 12.03 (s, 1H), 7.02-6.99 (m, 3H), 6.95 (d, J=7.8 Hz, 1H), 6.85 (s, 1H), 6.69 (d, J=8.4 Hz, 2H), 4.27 (s, 2H), 4.06-3.99 (m, 1H), 3.10 (s, 4H), 2.35 (s, 3H), 2.16 (t, J=7.5 Hz, J=14.7 Hz, 2H), 1.99 (s, 2H), 1.76-1.69 (m, 5H), 1.23-1.15 (m, 3H). Mass (m/z): 413 (M+23)

Example 42

Synthesis of 4-(4-((2-(2-methylbenzo[d]thiazol-5-yl)cyclohept-1-en-1-yl)methoxy)phenyl)butanoic Acid

Step 42a

Synthesis of methyl 4-(4-((2-(2-methylbenzo[d]thiazol-5-yl)cyclohept-1-en-1-yl)methoxy)phenyl) butanoate The title compound was prepared in an analogous manner as in step 1b of Example 1 involving the reaction of methyl 4-(4-((2-bromocyclohept-1-en-1-yl)methoxy)phenyl)butanoate. (0.150 g, 0.393 mmol) with (2-methylbenzo[d]thiazol-5-yl)boronic acid (0.114 g, 0.590 mmol) in presence of sodium bicarbonate (0.083 g, 0.983 mmol) and tetrakis(triphenylphosphine)palladium(0) (0.023 mg, 0.020 mmol) to afford the title compound (0.130 g). Yield: 73%

$^1$H NMR (300 MHz, CDCl$_3$): δ 7.04-6.99 (m, 4H), 6.87 (s, 1H), 6.73 (d, J=8.4 Hz, 2H), 4.34 (s, 2H), 3.67 (s, 3H), 3.17 (s, 3H), 2.60-2.55 (m, 4H), 2.47-2.44 (m, 2H), 2.34-2.29 (m, 2H), 1.96-1.84 (m, 4H), 1.64 (s, 4H). Mass (m/z): 450 (M+1).

Step 42b

Synthesis of 4-(4-((2-(bicyclo[4.2.0]octa-1(6),2,4-trien-3-yl)cyclohept-1-en-1-yl)methoxy) phenyl) butanoic Acid The title compound was prepared in an analogous manner as in step 1c of Example 1 involving the reaction of the compound obtained in step 42a, methyl 4-(4-((2-(2-methylbenzo[d]thiazol-5-yl)cyclohept-1-en-1-yl)methoxy)phenyl)butanoate (0.120 g, 0.267 mmol) with LiOH.H$_2$O (0.106 mL, 1.60 mmol) to afford the title compound (0.108 g). Yield: 93%

$^1$H NMR: (300 MHz, DMSO-d$_6$): δ 12.01 (s, 1H), 7.99 (d, J=8.4 Hz, 1H), 7.65 (s, 1H), 7.21 (d, J=8.4 Hz, 1H), 7.01 (d, J=8.7 Hz, 2H), 6.70 (d, J=8.7 Hz, 2H), 4.30 (s, 2H), 2.77 (s, 3H), 2.56-2.44 (m, 6H), 2.15 (t, J=7.2 Hz, J=14.7 Hz, 2H), 1.81 (s, 2H), 1.73-1.65 (m, 4H), 1.55 (s, 2H). Mass (m/z): 436 (M+1).

Example 43

Synthesis of 4-(4-((2-(p-tolyl)cyclohept-1-en-1-yl)methoxy)phenyl)butanoate metformin Salt Metformin (0.034 g, 0.262 mmol) in dry THF (1.5 mL) was stirred under argon atmosphere for 15 minutes. 4-(4-((2-(p-tolyl)cyclohept-1-en-1-yl)methoxy)phenyl)butanoic acid (0.100 g, 0.262 mmol) was added to the suspension obtained and stirred the mixture for 4 h. To the reaction mixture was added hexane (10 mL), stirred for 10 minutes and solvent was decanted from the mixture. The residue obtained was dried over high vacuum to afford the title compound (0.115 g). Yield: 86%

$^1$H NMR (500 MHz, DMSO-d$_6$): δ 7.8-7.14 (5H), 7.14-7.12 (d, J=7.8 Hz, 2H), 7.05-7.04 (d, J=7.8 Hz, 2H), 7.00-6.97 (d, J=8.4 Hz, 2H), 6.66-6.63 (d, J=8.40 Hz, 2H), 4.27 (s, 2H), 2.90 (s, 6H), 2.50-2.39 (m, 6H), 2.27 (s, 3H), 1.83-1.81 (m, 4H), 1.66-1.51 (m, 6H); Mass (m/z): 401.5 (M+23), 377.1 (M−1).

Example 44

Synthesis of 4-(4-((2-(p-tolyl)cyclohept-1-en-1-yl)methoxy)phenyl)butanoate, piperazine-1,4-diium Salt Piperazine (0.023 g, 0.262 mmol) in dry THF (1.5 mL) was stirred under argon atmosphere for 15 minutes. 4-(4-((2-(p-tolyl)cyclohept-1-en-1-yl)methoxy)phenyl)butanoic acid (0.200 g, 0.524 mmol) was added to the suspension obtained and the mixture was stirred for 4 h. The reaction mixture was stirred in hexane (10 mL) for 10 minutes, the solvent was decanted out and the mass obtained was dried over high vacuum to afford the title compound (0.200 g). Yield: 88%

$^1$H NMR (500 MHz, DMSO-d$_6$): δ 7.14-7.12 (d, J=7.8 Hz, 4H), 7.05-6.98 (m, 8H), 7.00-6.97 (d, J=8.4 Hz, 4H), 6.68-6.65 (d, J=8.40 Hz, 4H), 4.27 (s, 4H), 2.67 (s, 8H), 2.50-2.39 (m, 12H), 2.27 (s, 6H), 1.83-1.81 (m, 8H), 1.66-1.51 (m, 12H); Mass (m/z): 401.5 (M+23), 377.1 (M−1)

Example 45

Synthesis of 4-(4-((2-(p-tolyl)cyclohept-1-en-1-yl)methoxy)phenyl)butanoate, 2-hydroxyethanaminium Salt Ethanolamine (0.024 g, 0.396 mmol) in dry THF (1.5 mL) was stirred under argon atmosphere for 15 minutes. 4-(4-((2-(p-tolyl)cyclohept-1-en-1-yl)methoxy)phenyl)butanoic acid (0.150 g, 0.396 mmol) was added to the suspension obtained and the mixture was stirred for 24 hours. The reaction mixture was then concentrated, triturated with ethyl acetate/hexane (20%, 10 mL), stirred for 3 hours and solvent was decanted out to afford the title compound (0.150 g). Yield: 84%

$^1$H NMR (500 MHz, DMSO-d$_6$): δ 7.14-7.11 (d, J=7.5 Hz, 2H), 7.05-6.98 (m, 4H), 6.67-6.65 (d, J=7.8 Hz, 2H), 4.27 (s, 2H), 3.44-3.40 (t, 2H), 2.65-2.50 (t, 2H), 2.50-2.46 (m, 4H), 2.45-2.39 (m, 4H), 2.27 (s, 3H), 2.04-2.02 (t, 2H), 1.78-1.69 (m, 4H), 1.58-1.50 (m, 4H); Mass (m/z): 401.5 (M+23), 377.1 (M−1).

Example 46

Synthesis of 4-(4-((2-(p-tolyl)cyclohept-1-en-1-yl)methoxy)phenyl)butanoate, sodium Salt 4-(4-((2-(p-tolyl)cyclohept-1-en-1-yl)methoxy)phenyl) butanoic acid (0.209 g, 0.552 mmol) in dry THF (1.5 mL) was stirred and sodium hydroxide (0.022 g, 0.552 mmol) was added to it followed by addition of water (0.1 mL). The reaction mixture was stirred for overnight. The reaction mixture was then concentrated and triturated with ethyl acetate (5 mL) to afford the title compound (0.110 g). Yield: 66.5%

$^1$H NMR (500 MHz, DMSO-d$_6$): δ 7.14-7.12 (d, J=7.8 Hz, 2H), 7.05-6.96 (m, 4H), 6.66-6.63 (d, J=8.4 Hz, 2H), 4.27 (s, 2H), 2.50-2.46 (m, 4H), 2.43-2.39 (m, 4H), 2.27 (s, 3H), 1.81-1.79 (m, 4H), 1.64-1.59 (m, 6H); Mass (m/z): 401.5 (M+23), 377.1 (M−1).

Example 47

Synthesis of 4-(4-((4-(p-tolyl)-5,6-dihydro-2H-pyran-3-yl)methoxy)phenyl)butanoic Acid

Step 47a

Synthesis of methyl 4-(4-((4-bromo-5,6-dihydro-2H-pyran-3-yl)methoxy)phenyl)butanoate A mixture of 4-bromo-5-(bromomethyl)-3,6-dihydro-2H-pyran (1 g, 3.91 mmol), methyl 4-(4-hydroxyphenyl)butanoate (0.835 g, 4.30 mmol), cesium carbonate (1.910 g, 5.86 mmol) in acetonitrile (5 mL), was stirred at room temperature for 8 h. After the completion of reaction, ethyl acetate (30 mL) was added to the reaction mixture and filtered. The filtrate was concentrated and the obtained material was purified by column chromatography (10%, ethyl acetate/pet ether) to afford the title compound (0.605 g). Yield: 41.9%

$^1$H NMR (500 MHz, DMSO-d$_6$): δ 7.11 (d, J=8.4 Hz, 2H), 6.85 (d, J=8.4 Hz, 2H), 4.69 (s, 2H), 4.28 (s, 2H), 3.85-3.82 (m, 2H), 3.67 (s, 3H), 2.64-2.57 (m, 4H), 2.32 (t, J=7.5 Hz, 2H), 1.97-1.87 (m, 2H).

Step 47b

Synthesis of methyl 4-(4-((4-(p-tolyl)-5,6-dihydro-2H-pyran-3-yl)methoxy)phenyl)butanoate The title compound was prepared in an analogous manner as in step 1b of Example 1 involving the reaction of methyl 4-(4-((4-bromo-5,6-dihydro-2H-pyran-3-yl)methoxy)phenyl)butanoate (0.068 g, 0.184 mmol) with p-tolylboronic acid (0.038 g, 0.276 mmol) in presence of sodium bicarbonate (0.039 g, 0.460 mmol) and tetrakis(triphenylphosphine)palladium(0) (0.0026 g, 0.009 mmol) to afford the title compound (0.030 g). Yield: 42%

$^1$H NMR (300 MHz, CDCl$_3$) δ: 1H NMR, DMSO (300 HZ): δ 7.41-7.39 (m, 4H), 7.05 (d, J=5.1 Hz, 2H), 6.74 (d, J=4.8 Hz, 2H), 4.39 (s, 2H), 3.96-3.93 (m, 2H), 3.67 (s, 3H), 2.59-2.56 (m, 2H), 2.48 (s, 2H), 2.36 (s, 3H), 2.33-2.30 (m, 2H), 1.94-1.88 (m, 2H), 1.27 (s, 2H; Mass: 403 (M+23).

Step 47c

Synthesis of 4-(4-((4-(p-tolyl)-5,6-dihydro-2H-pyran-3-yl)methoxy)phenyl)butanoic Acid The title compound was prepared in an analogous manner as in step 1c of Example 1 involving the reaction of the compound obtained in step 47b, methyl 4-(4-((4-(p-tolyl)-5,6-dihydro-2H-pyran-3-yl)methoxy)phenyl)butanoate (0.025 g, 0.066 mmol) with LiOH.H$_2$O (0.246 mL, 0.396 mmol) to afford the title compound (0.020 g). Yield: 83%

$^1$H NMR (300 MHz, CDCl$_3$) δ: 12.02 (s, 1H), 7.16 (s, 4H), 7.05 (d, J=4.8 Hz, 1H), 6.75 (d, J=4.8 Hz, 1H), 4.34 (s, 2H), 4.23 (s, 2H), 3.82 (t, J=3.3 Hz, 6.6 Hz, 2H), 2.40 (s, 2H), 2.28 (s, 3H), 2.18-2.16 (m, 2H), 1.75-1.17 (m, 2H), 1.27-1.24 (m, 2H); Mass (m/z): 389 (M+23).

Example 48

Synthesis of 4-(4-((4-(4-(1-cyanocyclopropyl)phenyl)-5,6-dihydro-2H-pyran-3-yl)methoxy)phenyl)butanoic Acid

Step 48a

Synthesis of methyl 4-(4-((4-(4-(1-cyanocyclopropyl)phenyl)-5,6-dihydro-2H-pyran-3-yl)methoxy)phenyl)butanoate The title compound was prepared in an analogous manner as in step 1b of Example 1 involving the reaction of methyl 4-(4-((4-bromo-5,6-dihydro-2H-pyran-3-yl)methoxy)phenyl)butanoate (0.150 g, 0.406 mmol) with (4-(1-cyanocyclopropyl)phenyl)boronic acid (0.137 g, 0.731 mmol) in presence of sodium bicarbonate (0.085 g, 1.01 mmol) and tetrakis(triphenylphosphine) palladium(0) (0.006 g, 0.020 mmol) to afford the title compound (0.067 g). Yield: 37%

$^1$H NMR (300 MHz, CDCl$_3$) δ: 7.29 (s, 4H), 7.04 (d, J=8.1 Hz, 2H), 6.75 (d, J=8.4 Hz, 2H), 4.31 (s, 2H), 4.22 (s, 2H), 3.81 (s, 2H), 3.55 (s, 3H), 2.39 (s, 3H), 2.25 (t, J=7.2 Hz, 14.7, 2H), 1.78-1.71 (m, 4H), 1.49-1.47 (m, 3H); Mass (m/z): 454 (M+23).

Step 48b

Synthesis of 4-(4-((4-(4-(1-cyanocyclopropyl)phenyl)-5,6-dihydro-2H-pyran-3-yl)methoxy) phenyl) butanoic Acid The title compound was prepared in an analogous manner as in step 1c of Example 1 involving the reaction of the compound obtained in step 48a, methyl 4-(4-((4-(4-(1-cyanocyclopropyl)phenyl)-5,6-dihydro-2H-pyran-3-yl)methoxy)phenyl)butanoate (0.060 g, 0.139 mmol) with LiOH.H$_2$O (0.556 mL, 0.834 mmol) to afford the title compound (0.050 g). Yield: 86%.

$^1$H NMR (300 MHz, CDCl$_3$) δ: 11.94 (s, 1H), 7.29 (s, 4H), 7.05 (d, J=8.4 Hz, 2H), 6.75 (d, J=8.4 Hz, 2H), 4.32 (s, 2H), 4.23 (s, 2H), 3.81 (d, J=5.4 Hz, 2H), 2.40 (s, 3H), 2.15 (t, J=7.5 Hz, 14.7 Hz, 2H), 1.73-1.69 (m, 4H), 1.52-1.48 (m, 2H), 1.26-1.16 (m, 3H); Mass (m/z): 440 (M+23).

Example 49

Synthesis of 4-(4-((4-(5,6,7,8-tetrahydronaphthalen-2-yl)-5,6-dihydro-2H-pyran-3-yl)methoxy)phenyl)butanoic Acid Step 49a Synthesis of methyl 4-(4-((4-(5,6,7,8-tetrahydronaphthalen-2-yl)-5,6-dihydro-2H-pyran-3-yl)methoxy)phenyl)butanoate The title compound was prepared in an analogous manner as in step 1b of Example 1 involving the reaction of methyl 4-(4-((4-bromo-5,6-dihydro-2H-pyran-3-yl)methoxy)phenyl)butanoate (0.078 g, 0.211 mmol) with (5,6,7,8-tetrahydronaphthalen-2-yl)boronic acid (0.054 g, 0.317 mmol) in presence of sodium bicarbonate (0.044 g, 0.528 mmol) and tetrakis(triphenylphosphine) palladium(0) (0.003 g, 0.001 mmol) to afford the title compound (0.064 g). Yield: 72%

$^1$H NMR (300 MHz, CDCl$_3$) δ: 7.05-7.02 (m, 3H), 6.96 (d, J=9.6 Hz, 2H), 6.75 (d, J=8.4 Hz, 2H), 4.40 (s, 2H), 3.93 (m, 2H), 3.66 (s, 3H), 2.76-2.72 (m, 4H), 2.57 (t, J=7.5 Hz, 14.7 Hz, 4H), 2.46 (m, 2H), 2.31 (t, J=7.5 Hz, 15 Hz, 2H), 1.95-1.85 (m, 2H), 1.79 (s, 4H); Mass (m/z): 443 (M+23).

Step 49b

Synthesis of 4-(4-((4-(5,6,7,8-tetrahydronaphthalen-2-yl)-5,6-dihydro-2H-pyran-3-yl)methoxy)phenyl)butanoic Acid The title compound was prepared in an analogous manner as in step 1c of Example 1 involving the reaction of the compound obtained in step 49a, methyl 4-(4-((4-(5,6,7,8-tetrahydronaphthalen-2-yl)-5,6-dihydro-2H-pyran-3-yl)methoxy)phenyl)butanoate (0.060 g, 0.143 mmol) with LiOH.H$_2$O (0.571 mL, 0.856 mmol) to afford the title compound (0.050 g).

Yield: 83%

$^1$H NMR (300 MHz, CDCl$_3$) δ: 12.02 (s, 1H), 7.05-6.99 (m, 3H), 6.96 (d, J=8.4 Hz, 2H), 6.76 (d, J=8.1 Hz, 2H), 4.32 (s, 2H), 4.21 (s, 2H), 3.79 (s, 2H), 2.66-2.60 (m, 4H), 2.37 (s, 4H), 2.15 (t, J=7.2 Hz, 14.4 Hz, 2H), 1.74-1.68 (m, 6H); Mass (m/z): 429 (M+23).

Example 50

Synthesis of 4-(4-((2-(p-tolyloxy)cyclohex-1-en-1-yl)methoxy)phenyl)butanoic Acid Step 50a Synthesis of methyl 4-(4-((2-(p-tolyloxy)cyclohex-1-en-1-yl)methoxy)phenyl)butanoate A mixture of methyl 4-(4-((2-bromocyclohex-1-en-1-yl)methoxy)phenyl)butanoate (0.100 g, 0.272 mmol), p-cresol (0.035 g, 0.327 mmol), potassium phosphate (0.116 g, 0.546 mmol) and di-tert-butyl(2',6'-diphenyl-[1,1':4',1''-terphenyl]-2-yl)phosphine (0.0035 g. 0.008 mmol) was stirred in dry toluene (5 mL) and flushed with argon for 5 minutes. Palladium acetate (0.0012 g, 0.005 mmol) was added to the stirred mixture and again flushed for 5 min. The reaction mixture was heated at 110° C. for 6 hours. After the completion of reaction, the reaction mixture was cooled to room temperature and concentrated. The reaction mass obtained was quenched by ammonium chloride solution (20 mL). The aqueous layer was extracted with ethyl acetate (4×20 mL), the combined organic layer was dried over sodium sulphate, concentrated to afford the title compound (0.075 g) which was purified by column chromatography (0-10%, ethyl acetate/pet ether). Yield: 70%

$^1$H NMR (300 MHz, CDCl$_3$): δ 7.117.05 (m, 4H), 6.87-6.82 (m, 4H), 4.58 (s, 2H), 3.67 (s, 3H), 2.61-2.56 (t, 2H), 2.35-2.31 (m, 7), 2.11 (t, 2H), 1.97-1.87 (m, 2H), 1.73 (m, 4H).

Step 50b

Synthesis of 4-(4-((2-(p-tolyloxy)cyclohex-1-en-1-yl)methoxy)phenyl)butanoic Acid The title compound was prepared in an analogous manner as in step 1c of Example 1 involving the reaction of the compound obtained in step 50a, methyl 4-(4-((2-(p-tolyloxy)cyclohex-1-en-1-yl)methoxy)phenyl)butanoate (0.075 g, 0.190 mmol) with LiOH.H$_2$O (0.756 mL, 1.14 mmol) to afford the title compound (0.065 g). Yield: 90%

$^1$H NMR (300 MHz, CDCl$_3$): δ 7.10-7.05 (m, 4H), 6.87-6.81 (m, 4H), 4.58 (s, 2H), 2.63-2.58 (t, 2H), 2.39-2.34 (m, 4H), 2.31 (s, 3H), 2.11 (bt, 2H), 1.96-1.91 (m, 2H), 1.71-1.70 (m, 4H); Mass (m/z): 379.1 (M−1), 403.2 (M+23).

Example 51

Synthesis of 4-(4-((2-phenoxycyclohex-1-en-1-yl)methoxy)phenyl)butanoic Acid

Step 51a

Synthesis of methyl 4-(4-((2-phenoxycyclohex-1-en-1-yl)methoxy)phenyl)butanoate

A mixture of methyl 4-(4-((2-bromocyclohex-1-en-1-yl)methoxy)phenyl)butanoate (0.225 g, 0.613 mmol), phenol (0.069 g, 0.735 mmol), potassium phosphate (0.260 g, 1.22 mmol) and di-tert-butyl(2',6'-diphenyl-[1,1':4',1''-terphenyl]-2-yl)phosphine (0.008 g, 0.018 mmol) were stirred in dry toluene (5 mL) and flushed with argon for 5 minutes. Palladium acetate (0.0028 g, 0.012 mmol) was added to the mixture and again flushed for 5 minutes. The reaction mixture was heated at 110° C. for 6 hours. The reaction mixture cooled to room temperature, concentrated, quenched by ammonium chloride solution (20 mL). The aqueous layer was extracted with ethyl acetate (4×20 mL), the combined organic layer was dried over sodium sulphate and concentrated to afford the title compound (0.090 g) which was purified by column chromatography (0-10%, ethyl acetate/petroleum ether). Yield: 39%

$^1$H NMR (300 MHz, DMSO-d$_6$): δ 7.34-7.29 (m, 2H), 7.05-6.98 (m, 3H), 6.93-6.91 (d, J=8.1 Hz, 2H), 6.82-6.79 (d, J=8.4 Hz, 2H), 4.59 (s, 2H), 3.56 (s, 3H), 2.51-2.49 (m, 4H), 2.28-2.23 (m, 2H), 2.04 (bt, 2H), 1.78-1.66 (m, 6H); Mass (m/z): 403.1 (M+23).

Step 51b

Synthesis of 4-(4-((2-phenoxycyclohex-1-en-1-yl)methoxy)phenyl)butanoic Acid The title compound was prepared in an analogous manner as in step 1c of Example 1 involving the reaction of the compound obtained in step 51a, methyl 4-(4-((2-phenoxycyclohex-1-en-1-yl)methoxy)phenyl)butanoate (0.080 g, 0.210 mmol) with LiOH.H$_2$O (0.790 mL, 1.26 mmol) to afford the title compound (0.056 g). Yield: 73%

$^1$H NMR (300 MHz, DMSO-d$_6$): δ 12.03 (s, 1H), 7.34-7.29 (m, 2H), 7.05-6.98 (m, 3H), 6.94-6.91 (d, J=9.0 Hz, 2H), 6.82-6.79 (d, J=8.7 Hz, 2H), 4.66 (s, 2H), 2.51-2.49 (m, 2H), 2.23-2.21 (m, 4H), 2.07 (bt, 2H), 1.74-1.67 (m, 6H); Mass (m/z): 366.1 (M−1), 386.2 (M+23).

Example 52

Synthesis of 4-(4-((2-(p-tolyloxy)cyclohept-1-en-1-yl)methoxy)phenyl)butanoic Acid

Step 52a

Synthesis of methyl 4-(4-((2-(p-tolyloxy)cyclohept-1-en-1-yl)methoxy)phenyl)butanoate A mixture of methyl 4-(4-((2-bromocyclohept-1-en-1-yl)methoxy)phenyl)butanoate (0.150 g, 0.393 mmol), p-cresol (0.051 g, 0.472 mmol), potassium phosphate (0.167 g, 0.787 mmol) and di-tert-butyl(2',6'-diphenyl-[1,1':4',1''-terphenyl]-2-yl)phosphine (0.005 g, 0.012 mmol) was stirred in dry toluene (5 mL) and flushed with argon for 5 minutes. Palladium acetate (0.002 g, 0.008 mmol) was added to the mixture and again flushed for 5 minutes. The reaction mixture was heated at 110° C. for 6 hours. After the completion of reaction, the reaction mixture was cooled to room temperature and concentrated. The reaction mass obtained was quenched by ammonium chloride solution (20 mL). The aqueous layer was extracted with ethyl acetate (4×20 mL), the combined organic layer was dried over sodium sulphate and concentrated to afford the title compound (0.029 g) which was purified by column chromatography (0-10%, ethyl acetate/petroleum ether). Yield: 18%

$^1$H NMR (300 MHz, CDCl$_3$): δ 7.11-7.03 (m, 4H), 6.86-6.81 (m, 4H), 4.58 (s, 2H), 3.67 (s, 3H), 2.61-2.56 (m, 2H), 2.35-2.30 (m, 8H), 1.94-1.75 (m, 5H), 1.58 (s, 4H).

Step 52b

Synthesis of 4-(4-((2-(p-tolyloxy)cyclohept-1-en-1-yl)methoxy)phenyl)butanoic Acid The title compound was prepared in an analogous manner as in step 1c of Example 1 involving the reaction of the compound obtained in step 52a, methyl 4-(4-((2-(p-tolyloxy)cyclohept-1-en-1-yl)methoxy)phenyl)butanoate (0.025 g, 0.061 mmol) with LiOH.H$_2$O (0.245 mL, 0.367 mmol) to afford the title compound (0.020 g). Yield: 83%

$^1$H NMR (300 MHz, DMSO-d$_6$): δ 12.03 (s, 1H), 7.13 (d, J=7.8 Hz, 2H), 7.04 (d, J=7.8 Hz, 2H), 6.82 (d, J=8.4 Hz, 4H), 4.46 (s, 2H), 2.23 (s, 3H), 2.16 (s, 2H), 1.72-1.69 (m, 4H), 1.57-1.50 (m, 4H), 1.51 (s, 4H), 1.23-1.16 (m, 4H); Mass (m/z): 417 (m+23).

Example 53

Synthesis of 4-(4-((4'-(1-cyanocyclopropyl)-4-methyl-3,4,5,6-tetrahydro-[1,1'-biphenyl]-2-yl)methoxy) phenyl)butanoic Acid

Step 53a

Synthesis of methyl 4-(4-((2-bromo-5-methylcyclohex-1-en-1-yl)methoxy)phenyl)butanoate A mixture of 1-bromo-2-(bromomethyl)-4-methylcyclohex-1-ene (0.970 g, 3.62 mmol), methyl 4-(4-hydroxyphenyl)butanoate (0.844 g, 4.32 mmol), cesium carbonate (3.54 g, 10.86 mmol) in acetonitrile (10 mL), was stirred at room temperature for 8 hours. After the completion of reaction, the reaction mass was diluted with ethyl acetate (50 mL) and filtered. The organic layer was concentrated and the residue obtained was purified by column chromatography (10%, ethyl acetate/petroleum ether) to afford the title compound (0.865 g).

Yield: 62%

Step 53b

Synthesis of methyl 4-(4-((4'-(1-cyanocyclopropyl)-4-methyl-3,4,5,6-tetrahydro-[1,1'-biphenyl]-2-yl)methoxy)phenyl)butanoate The title compound was prepared in an analogous manner as in step 1b of Example 1 involving the reaction of methyl 4-(4-((2-bromo-5-methylcyclohex-1-en-1-yl)methoxy)phenyl)butanoate (0.150 g, 0.393 mmol) with (4-(1-cyanocyclopropyl)phenyl)boronic acid (0.147 g, 0.787 mmol) in presence of sodium bicarbonate (0.083 g, 0.983 mmol) and tetrakis(triphenylphosphine)palladium(0) (0.006 g, 0.020 mmol) to afford the title compound (0.085 g). Yield: 49%

$^1$H NMR (300 MHz, DMSO-d$_6$): δ 7.27-7.18 (m, 4H), 7.02 (d, J=7.5 Hz, 2H), 6.71 (d, J=8.4 Hz, 2H), 4.26 (s, 2H), 3.51 (s, 3H), 2.31-2.22 (m, 5H), 1.83-1.70 (m, 7H), 1.50-1.46 (m, 2H), 1.28-1.21 (m, 2H), 0.99 (d, J=5.7 Hz, 3H); Mass (m/z): 466 (M+23).

Step 53c

Synthesis of 4-(4-((4'-(1-cyanocyclopropyl)-4-methyl-3,4,5,6-tetrahydro-[1,1'-biphenyl]-2-yl)methoxy) phenyl)butanoic Acid The title compound was prepared in an analogous manner as in step 1c of Example 1 involving the reaction of the compound obtained in step 53b, methyl 4-(4-((4'-(1-cyanocyclopropyl)-4-methyl-3,4,5,6-tetrahydro-[1,1'-biphenyl]-2-yl)methoxy)phenyl) butanoate (0.075 g, 0.169 mmol) with LiOH.H$_2$O (0.676 mL, 1.01 mmol) to afford the title compound (0.070 g). Yield: 96%

$^1$H NMR (300 MHz, DMSO-d$_6$): δ 11.89 (s, 1H), 7.28-7.19 (m, 4H), 7.02 (d, J=8.4 Hz, 2H), 6.72 (d, J=8.4 Hz, 2H), 4.27-4018 (m, 2H), 2.32 (s, 2H), 2.15 (t, J=7.2 Hz, 14.7 Hz,

2H), 1.73-1.70 (m, 5H), 1.51-1.46 (m, 2H), 1.32-1.15 (m, 5H), 1.00 (d, J=6 Hz, 3H); Mass (m/z): 452 (M+23).

Example 54

Synthesis of 4-(4-((4-fluoro-4'-methyl-3,4,5,6-tetrahydro-[1,1'-biphenyl]-2-yl)methoxy)phenyl) butanoic Acid Step 54a Synthesis of methyl 4-(4-((2-bromo-5-fluorocyclohex-1-en-1-yl)methoxy)phenyl)butanoate A mixture of 1-bromo-2-(bromomethyl)-4-fluorocyclohex-1-ene (0.111 g, 0.408 mmol). methyl 4-(4-hydroxyphenyl)butanoate (0.079 g, 0.408 mmol), cesium carbonate (0.133 g, 0.408 mmol) in acetonitrile (5 mL), was stirred at room temperature for 8 hours. After the completion of reaction, the reaction mass was diluted with ethyl acetate (25 mL) and filtered through celite bed, the organic layer was concentrated and the mass obtained was purified by column chromatography (10%, ethyl acetate/petroleum ether) to afford the title compound (0.120 g). Yield: 76%

Step 54b

Synthesis of methyl 4-(4-((4-fluoro-4'-methyl-3,4,5,6-tetrahydro-[1,1'-biphenyl]-2-yl)methoxy)phenyl) butanoate The title compound was prepared in an analogous manner as in step 1b of Example 1 involving the reaction of methyl 4-(4-((2-bromo-5-fluorocyclohex-1-en-1-yl)methoxy)phenyl)butanoate (0.065 g, 0.169 mmol) with p-tolylboronic acid (0.047 g, 0.337 mmol) in presence of sodium bicarbonate (0.035 g, 0.422 mmol) and tetrakis(triphenylphosphine) palladium(0) (0.010 g, 0.008 mmol) to afford the title compound (0.035 g). Yield: 53%

$^1$H NMR (500 MHz, CDCl$_3$): δ 7.16-7.14 (d, J=7.5 Hz, 2H), 7.09-7.07 (d, J=8.0 Hz, 2H), 7.06-7.03 (m, 2H), 6.75-6.71 (m, 2H), 5.11-5.10 (m, 1H), 4.39-4.30 (m, 2H), 3.67 (s, 3H), 2.50-2.45 (m, 4H), 2.40-2.36 (m, 2H), 2.28 (s, 3H), 2.18-2.15 (t, 2H), 1.98-1.80 (m, 2H), 1.75-1.69 (m, 2H); Mass: 419 (M+23).

Step 54c

Synthesis of 4-(4-((4-fluoro-4'-methyl-3,4,5,6-tetrahydro-[1,1'-biphenyl]-2-yl)methoxy)phenyl) butanoic Acid The title compound was prepared in an analogous manner as in step 1c of Example 1 involving the reaction of methyl 4-(4-((4-fluoro-4'-methyl-3,4,5,6-tetrahydro-[1,1'-biphenyl]-2-yl)methoxy)phenyl)butanoate (0.030 g, 0.076 mmol) with LiOH.H$_2$O (0.303 mL, 0.454 mmol), to afford the title compound (0.014 g). Yield: 48%

$^1$H NMR (500 MHz, DMSO-d$_6$): δ 12.00 (bs, 1H), 7.16-7.14 (d, J=7.5 Hz, 1H), 7.10-7.09 (d, J=8.0 Hz, 1H), 7.04-7.02 (d, J=8.5 Hz, 1H), 6.73-6.71 (d, J=8.5 Hz, 1H), 5.11-5.01 (m, 1H), 4.29 (s, 2H), 2.50-2.45 (m, 4H), 2.40-2.36 (m, 2H), 2.28 (s, 3H), 2.18-2.15 (t, 2H), 1.98-1.80 (m, 2H), 1.75-1.69 (m, 2H); Mass (m/z): 381 (M−1), 405.2 (M+23).

Example 55

Synthesis of ethyl 4-(5-((4-(6-methoxypyridin-3-yl)-5,6-dihydro-2H-pyran-3-yl)methoxy)pyridin-2-yl) butanoic Acid Step 55a Synthesis of methyl 4-(6-methoxypyridin-3-yl)-5,6-dihydro-2H-pyran-3-carbaldehyde A mixture of 4-bromo-5,6-dihydro-2H-pyran-3-carbaldehyde (250 mg, 1.309 mmol), (6-methoxypyridin-3-yl)boronic acid (300 mg, 1.963 mmol) and potassium carbonate (452 mg, 3.27 mmol) was stirred in dioxane:water (4:1) mixture and purged with argon for 5 minutes. Tetrakis (triphenylphosphine) palladium(0) (76 mg, 0.065 mmol) was added to the mixture and stirred at 110° C. for 5 hours. The reaction mixture was then cooled to room temperature, diluted with ethyl acetate (25 mL), filtered and the filtrate was concentrated to afford the title compound (0.250 g) which was purified by column chromatography (0-10% ethyl acetate/petroleum ether). Yield: 87%

$^1$H NMR (300 MHz, CDCl$_3$): δ 9.57 (bs, 1H), 8.12 (d, J=2.4 Hz, 1H), 7.56-7.52 (dd, J=8.7 & J=2.4 Hz, 1H), 6.83 (d, J=8.7 Hz, 1H), 4.49 (bt, 2H), 4.00 (s, 3H), 3.94 (t, 2H), 2.67-2.63 (m, 2H); Mass (m/z): 220 (M+1)

Step 55b

Synthesis of (4-(6-methoxypyridin-3-yl)-5,6-dihydro-2H-pyran-3-yl)methanol

The compound obtained in step 55a, 4-(6-methoxypyridin-3-yl)-5,6-dihydro-2H-pyran-3-carbaldehyde (250 mg, 1.140 mmol) was stirred in methanol at 0° C. followed by addition of sodium borohydride (21.57 mg, 0.570 mmol) The reaction mixture was stirred for 4 h. After the completion of the reaction, the reaction mixture was concentrated and poured to crushed ice, neutralized with 2N HCL solution and extracted with dichloromethane (3×75 mL). The combined organic layer was washed with brine (25 mL), dried over sodium sulfate and concentrated to afford the title compound (0.235 g). Yield: 93%.

$^1$H NMR (300 MHz, CDCl$_3$): δ 8.03 (d, J=2.1 Hz, 1H), 7.48-7.44 (dd, J=8.4 & J=2.1 Hz, 1H), 6.76 (d, J=8.4 Hz, 1H), 4.49 (bt, 2H), 4.00 (s, 3H), 4.07 (bt, 2H), 4.00-3.91 (m, 5H), 2.41 (bt, 2H); Mass (m/z): 223 (M+1).

Step 55c

Synthesis of 5-(5-(bromomethyl)-3,6-dihydro-2H-pyran-4-yl)-2-methoxypyridine

The compound obtained in step 55b, (4-(6-methoxypyridin-3-yl)-5,6-dihydro-2H-pyran-3-yl)methanol (220 mg, 0.994 mmol) was stirred in dry DCM (10 mL). Pyridine (7.87 mg, 0.099 mmol) was added to it and the mixture was stirred at 0° C. Phosphorous tribromide (0.047 mL, 0.497 mmol) was added to the mixture and stirred for 3 h. The reaction mixture was then diluted with dichloromethane (20 mL) and washed with saturated solution of sodium bicarbonate (25 mL) and brine (25 mL). The organic layer was dried over sodium sulfate and concentrated under vacuum to afford the title compound (0.283 g), which is used as such for the next step.

Step 55d

Synthesis of 5-(benzyloxy)-2-bromopyridine

A mixture of benzylbromide (3.24 g, 18.97 mmol), 6-bromopyridin-3-ol (3 g, 17.24 mmol) and cesium carbonate (8.43 g, 25.90 mmol) in dry acetonitrile (50 mL) was stirred overnight at room temperature. After the completion of the reaction, the reaction mixture was diluted with ethyl acetate (80 mL) and filtered. The filtrate was concentrated under vacuum to afford the title compound (4.05 g). Yield: 89%

$^1$H NMR (300 MHz, CDCl$_3$): δ 8.15 (s, 1H), 7.42-7.37 (m, 5H), 7.19-7.15 (m, 1H), 5.11 (s, 2H).

Step 55e

Synthesis of ethyl 4-(5-(benzyloxy)pyridin-2-yl)butanoate

The compound obtained in step 55d, 5-(benzyloxy)-2-bromopyridine (3 g, 11.36 mmol) was stirred in dry THF (30 mL) under argon atmosphere followed by addition of a solution of (4-ethoxy-4-oxobutyl)zinc(II) bromide in THF (25 mL, 0.5M, 12.49 mmol). 1,3-Bis(2,6-diisopropylphenyl)imidazol-2-ylidene](3-chloropyridyl)palladium(II)dichloride (0.386 g, 0.568 mmol) was added to the mixture and the mixture was stirred overnight at room temperature. The reaction mixture was then decomposed with saturated solution of ammonium chloride (50 mL), extracted with ethyl acetate (3×100 mL). The combined organic layer was washed with brine (25 mL), dried over sodium sulfate and concentrated. The crude material obtained was purified by column chromatography (0-10% ethyl acetate/petroleum ether) to afford the title compound (2.2 g). Yield: 64%

$^1$H NMR (300 MHz, DMSO-d$_6$): δ 8.31 (m, 1H), 7.45-7.34 (m, 5H), 7.22-7.18 (m, 1H), 7.09-7.07 (d, J=8.4 Hz, 1H), 5.10 (s, 2H), 4.17-4.10 (q, 2H), 2.81-2.76 (t, 2H), 2.38-2.33 (t, 2H), 2.10-2.00 (m, 2H), 1.28 (t, 3H).

Step 55f

Synthesis of ethyl 4-(5-hydroxypyridin-2-yl)butanoate

The compound obtained in step 55e, ethyl 4-(5-(benzyloxy)pyridin-2-yl)butanoate (0.370 g, 1.23 mmol) was suspended in ethanol (15 mL) and palladium over carbon (7 mg) was added to the mixture and the reaction mixture was stirred for 3 hours under hydrogen atmosphere (40 psi) at room temperature. After the completion of reaction, the reaction mixture was filtered, washed with ethanol (15 mL) and concentrated to afford the title compound (0.220 g). Yield: 85%

$^1$H NMR (300 MHz, DMSO-d$_6$): δ 8.22 (m, 1H), 7.25-7.23 (m, 1H), 7.13-7.10 (d, J=8.4 Hz, 1H), 4.16-4.09 (q, 2H), 2.82-2.77 (t, 2H), 2.378-2.33 (t, 2H), 2.04-2.00 (m, 2H), 1.27 (t, 3H).

Step 55 g

Synthesis of ethyl 4-(5-((4-(6-methoxypyridin-3-yl)-5,6-dihydro-2H-pyran-3-yl)methoxy)pyridin-2-yl)butanoate A mixture of the compound obtained in step 55c, 5-(5-(bromomethyl)-3,6-dihydro-2H-pyran-4-yl)-2-methoxypyridine (100 mg, 0.352 mmol) and cesium carbonate (172 mg, 0.528 mmol) was stirred in dry acetonitrile (10 mL) followed by addition of the compound obtained in step 55f, ethyl 4-(5-hydroxypyridin-2-yl)butanoate (73.6 mg, 0.352 mmol). The reaction mixture was stirred overnight at room temperature. The reaction mixture was then diluted with ethyl acetate (20 mL) and filtered. The filtrate was concentrated and the material obtained was purified by column chromatography (0-10% ethyl acetate/petroleum ether) to afford the title compound (0.120 g). Yield: 80%

$^1$H NMR (300 MHz, CDCl$_3$): δ 8.13 (d, 1H), 8.04 (d, J=2.1 Hz, 1H), 7.48-7.45 (dd, J=8.4 & J=2.1 Hz, 1H), 7.07-7.04 (m, 2H), 6.76 (d, J=8.4 Hz, 1H), 4.42-4.38 (m, 4H), 4.13 (q, 2H), 3.97-3.95 (m, 5H), 2.77 (t, 2H), 2.46 (bt, 2H), 2.34 (t, 2H), 2.03 (bt, 2H), 1.28-1.24 (m, 3H); Mass (m/z): 413.1 (M+1)

Step 55 h

Synthesis of ethyl 4-(5-((4-(6-methoxypyridin-3-yl)-5,6-dihydro-2H-pyran-3-yl)methoxy)pyridin-2-yl) butanoic Acid The title compound was prepared in an analogous manner as in step 1c of Example 1 involving the reaction of the compound obtained in step 55 g, ethyl 4-(5-((4-(6-methoxypyridin-3-yl)-5,6-dihydro-2H-pyran-3-yl)methoxy)pyridin-2-yl)butanoate (70 mg, 0.170 mmol) in THF: methanol (4:1) with LiOH.H$_2$O (0.679 mL, 1.018 mmol) to afford the title compound (0.052 g). Yield: 80%

$^1$H NMR (300 MHz, DMSO-d$_6$): δ 8.13 (bs, 1H), 8.03 (bs, 1H), 7.47 (d, J=8.4 Hz, 1H), 7.14 (m, 2H), 6.77 (d, J=8.4 Hz, 1H), 4.44-4.38 (m, 4H), 3.95 (s, 3H), 2.90 (t, 2H), 2.47 (bt, 2H), 2.39 (bt, 2H), 2.05 (bt, 2H); Mass (m/z): 385.1 (M+1).

Example 56

Synthesis of 4-(4-((4-(4-Cyanophenyl)-5,6-dihydro-2H-pyran-3-yl)methoxy)phenyl)butanoic Acid

Step 56a

Synthesis of methyl 4-(4-((4-(4-cyanophenyl)-5,6-dihydro-2H-pyran-3-yl)methoxy) phenyl)butanoate The title compound was prepared in an analogous manner as Example 1 involving the reaction of methyl 4-(4-((4-bromo-5,6-dihydro-2H-pyran-3-yl)methoxy)phenyl)butanoate (0.100. g, 0.271 mmol) with (4-cyanophenyl)boronic acid (0.060. g, 0.406 mmol) and potassium carbonate (0.094 g, 0.677 mmol) in the presence of (tetrakistriphenylphosphine) palladium(0) (0.016 g, 0.014 mmol) according to general procedure B (as described herein above). Yield: 45.8%.

Step 56b

Synthesis of 4-(4-((4-(4-cyanophenyl)-5,6-dihydro-2H-pyran-3-yl)methoxy)phenyl)butanoic Acid The title compound was prepared in an analogous manner as Example 1 involving the reaction of methyl 4-(4-((4-(4-cyanophenyl)-5,6-dihydro-2H-pyran-3-yl)methoxy) phenyl) butanoate (0.025 g, 0.064 mmol) with LiOH.H$_2$O (0.255 mL, 0.383 mmol), according to general procedure C (as described herein above). Yield: 83%.

$^1$H NMR (300 MHz, CDCl$_3$) δ: 7.67-7.64 (d, J=8.4 Hz, 2H), 7.37-7.35 (d, J=8.1 Hz, 2H), 7.08-7.06 (d, J=8.4 Hz,

2H), 6.73-6.71 (d, J=8.4 Hz, 2H), 4.40 (s, 2H), 4.30 (s, 2H), 3.99-3.95 (t, 2H), 2.64-2.59 (m, 2H), 2.47 (bs, 2H), 2.39-2.34 (t, 2H), 1.98-1.91 (m, 2H); Mass: 376 (M−1).

Example 57

Synthesis of 4-(4-((4-(6-methoxypyridin-3-yl)-5,6-dihydro-2H-pyran-3-yl)methoxy) phenyl) butanoic Acid Step 57a Synthesis of methyl 4-(4-((4-(6-methoxypyridin-3-yl)-5,6-dihydro-2H-pyran-3-yl)methoxy)phenyl) butanoate The title compound was prepared in an analogous manner as Example 1 involving the reaction of methyl 4-(4-((4-bromo-5,6-dihydro-2H-pyran-3-yl)methoxy)phenyl)butanoate (0.100. g, 0.271 mmol) with (6-methoxypyridin-3-yl)boronic acid (0.062. g, 0.406 mmol) and potassium carbonate (0.094 g, 0.677 mmol) in the presence of (tetrakistriphenylphosphine) palladium(0) (0.016 g, 0.014 mmol) according to general procedure B (as described herein above). Yield: 44.1%.

$^1$H NMR (300 MHz, CDCl$_3$) δ: 8.06-8.05 (d, J=2.1 Hz, 1H), 7.49-7.45 (dd, J=2.4; 8.4 Hz, 1H), 7.07-7.04 (d, J=8.4 Hz, 2H), 6.76-6.72 (m, 3H), 4.39 (s, 2H), 4.37 (s, 2H), 3.97-3.94 (m, 5H), 3.67 (s, 3H), 2.61-2.56 (t, 2H), 2.46 (t, 2H), 2.35-2.30 (t, 2H), 1.97-1.87 (m, 2H); Mass: 398.1 (M+1)

Step 57b

Synthesis of 4-(4-((4-(6-methoxypyridin-3-yl)-5,6-dihydro-2H-pyran-3-yl)methoxy)phenyl) butanoic Acid The title compound was prepared in an analogous manner as Example 1 involving the reaction of methyl 4-(4-((4-(6-methoxypyridin-3-yl)-5,6-dihydro-2H-pyran-3-yl)methoxy)phenyl)butanoate (0.025 g, 0.063 mmol) with LiOH.H$_2$O (0.252 mL, 0.377 mmol), according to general procedure C (as described herein above). Yield: 77%.

$^1$H NMR (300 MHz, CDCl$_3$) δ: 8.01 (s, 1H), 7.49-7.45 (d, J=8.7 Hz, 1H), 7.08-7.06 (d, J=8.4 Hz, 2H), 6.76-6.73 (d, 3H), 4.40 (s, 2H), 4.38 (s, 2H), 3.97-3.94 (m, 5H), 2.64-2.60 (t, 2H), 2.45 (t, 2H), 2.38-2.34 (t, 2H), 1.97-1.92 (m, 2H); Mass: 384.1 (M+1)

Example 58

Synthesis of 4-(4-((4-(2-methoxypyrimidin-5-yl)-5,6-dihydro-2H-pyran-3-yl)methoxy) phenyl)butanoic Acid Step 58a Synthesis of methyl 4-(4-((4-(2-(dimethylamino)pyrimidin-5-yl)-5,6-dihydro-2H-pyran-3-yl)methoxy)phenyl)butanoate The title compound was prepared in an analogous manner as Example 1 involving the reaction of methyl 4-(4-((4-bromo-5,6-dihydro-2H-pyran-3-yl)methoxy)phenyl)butanoate (0.200. g, 0.542 mmol) with (2-(dimethylamino)pyrimidin-5-yl)boronic acid (0.136 g, 0.812 mmol) and potassium carbonate (0.187 g, 1.354 mmol) in the presence of (tetrakistriphenylphosphine) palladium(0) (0.031 g, 0.027 mmol) according to general procedure B (as described herein above). Yield: 43.3%.

$^1$H NMR (300 MHz, CDCl$_3$): δ 8.24 (s, 2H), 7.08-7.05 (d, J=8.4 Hz, 2H), 6.77-6.74 (d, J=8.4 Hz, 2H), 4.39 (s, 2H), 4.38 (s, 2H), 3.96-3.93 (s, 2H), 3.68 (s, 3H), 3.21 (s, 6H), 2.61-2.56 (t, 2H), 2.43 (bt, 2H), 2.35-2.30 (t, 2H), 1.97-1.87 (m, 2H); Mass: 412.2 (M+1).

Step 58b

Synthesis of 4-(4-((4-(2-(dimethylamino)pyrimidin-5-yl)-5,6-dihydro-2H-pyran-3-yl) methoxy)phenyl) butanoic Acid The title compound was prepared in an analogous manner as Example 1 involving the reaction of methyl 4-(4-((4-(2-(dimethylamino)pyrimidin-5-yl)-5,6-dihydro-2H-pyran-3-yl)methoxy)phenyl)butanoate (0.050 g, 0.122 mmol) with LiOH.H$_2$O (0.486 mL, 0.729 mmol), according to general procedure C (as described herein above). Yield: 50.6%.

$^1$H NMR (300 MHz, CDCl$_3$): δ 8.17 (s, 2H), 7.10-7.07 (d, J=8.4 Hz, 2H), 6.78-6.75 (d, J=8.4 Hz, 2H), 4.40 (s, 4H), 3.96-3.93 (s, 2H), 3.19 (s, 6H), 2.66-2.61 (t, 2H), 2.42 (bt, 2H), 2.38-2.33 (t, 2H), 2.00-1.95 (m, 2H)

Example 59

Synthesis of 4-(4-((4-(2-methoxypyrimidin-5-yl)-5,6-dihydro-2H-pyran-3-yl)methoxy) phenyl)butanoic Acid Step 59a Synthesis of methyl 4-(4-((4-(2-methoxypyrimidin-5-yl)-5,6-dihydro-2H-pyran-3-yl)methoxy)phenyl) butanoate The title compound was prepared in an analogous manner as Example 1 involving the reaction of methyl 4-(4-((4-bromo-5,6-dihydro-2H-pyran-3-yl)methoxy)phenyl)butanoate (0.200. g, 0.542 mmol) with (2-methoxypyrimidin-5-yl)boronic acid (0.125 g, 0.812 mmol) and potassium carbonate (0.187 g, 1.354 mmol) in the presence of (tetrakistriphenylphosphine) palladium(0) (0.031 g, 0.027 mmol) according to general procedure B (as described herein above). Yield: 48%.

$^1$H NMR (300 MHz, CDCl$_3$): δ 8.43 (s, 2H), 7.08-7.06 (d, J=8.4 Hz, 2H), 6.76-6.73 (d, J=8.4 Hz, 2H), 4.40 (s, 2H), 4.32 (s, 2H), 4.03 (s, 3H), 3.99-3.95 (t, 2H), 3.67 (s, 3H), 2.61-2.56 (t, 2H), 2.47 (bt, 2H), 2.35-2.30 (t, 2H), 1.97-1.87 (m, 2H); Mass: 399.1 (M+1)

Step 59 b

Synthesis of 4-(4-((4-(2-methoxypyrimidin-5-yl)-5,6-dihydro-2H-pyran-3-yl)methoxy) phenyl) butanoic Acid The title compound was prepared in an analogous manner as Example 1 involving the reaction of 4-(4-((4-(2-methoxypyrimidin-5-yl)-5,6-dihydro-2H-pyran-3-yl)methoxy)phenyl)butanoic acid (0.050 g, 0.125 mmol) with LiOH.H$_2$O (0.502 mL, 0.753 mmol), according to general procedure C (as described herein above). Yield: 43%.

Example 60

Synthesis of 4-(4-((4-(4-morpholinophenyl)-5,6-dihydro-2H-pyran-3-yl)methoxy) phenyl) butanoic Acid

Step 61a

Synthesis of methyl 4-(4-((4-(4-morpholinophenyl)-5,6-dihydro-2H-pyran-3-yl)methoxy) phenyl)butanoate The title compound was prepared in an analogous manner as Example 1 involving the reaction of methyl 4-(4-((4-bromo-5,6-dihydro-2H-pyran-3-yl)methoxy)phenyl)butanoate (0.100. g, 0.277 mmol) with (4-morpholinophenyl) boronic acid (0.084 g, 0.406 mmol) and potassium carbonate (0.094 g, 0.677 mmol) in the presence of (tetrakistriphenylphosphine) palladium(0) (0.016 g, 0.014 mmol) according to general procedure B (as described herein above). Yield: 72.8%.
$^1$H NMR (300 MHz, CDCl$_3$) δ: 7.19-7.16 (d, J=8.7 Hz, 2H), 7.07-7.04 (d, J=8.4 Hz, 2H), 6.91-6.88 (d, J=8.7 Hz, 2H), 6.76-6.73 (d, J=8.4 Hz, 2H), 4.40 (s, 2H), 4.38 (s, 2H), 3.96-3.93 (t, 2H), 3.89-3.86 (t, 4H), 3.68 (s, 3H), 3.20-3.17 (t, 4H), 2.61-2.56 (t, 2H), 2.48 (bs, 2H), 2.35-2.30 (t, 2H), 1.97-1.87 (m, 2H); Mass: 452 (M+1).

Step 60b

Synthesis of 4-(4-((4-(4-morpholinophenyl)-5,6-dihydro-2H-pyran-3-yl)methoxy)phenyl) butanoic Acid The title compound was prepared in an analogous manner as Example 1 involving the reaction of methyl 4-(4-((4-(4-morpholinophenyl)-5,6-dihydro-2H-pyran-3-yl)methoxy) phenyl)butanoate (0.025 g, 0.055 mmol) with LiOH.H$_2$O (0.221 mL, 0.332 mmol), according to general procedure C (as described herein above). Yield: 43%.
$^1$H NMR (300 MHz, CDCl$_3$) δ: 7.19-7.16 (d, J=8.7 Hz, 2H), 7.07-7.04 (d, J=8.4 Hz, 2H), 6.91-6.88 (d, J=8.7 Hz, 2H), 6.76-6.73 (d, J=8.4 Hz, 2H), 4.41 (s, 2H), 4.37 (s, 2H), 3.96-3.92 (t, 2H), 3.89-3.86 (t, 4H), 3.20-3.17 (t, 4H), 2.64-2.59 (t, 2H), 2.48 (bs, 2H), 2.39-2.34 (t, 2H), 1.98-1.88 (m, 2H); Mass: 438 (M+1), 436 (M−1)

Example 61

Synthesis of 4-(4-((4-(5-methylthiophen-2-yl)-5,6-dihydro-2H-pyran-3-yl)methoxy)phenyl) butanoic Acid

Step 61a

Synthesis of methyl 4-(4-((4-(5-methylthiophen-2-yl)-5,6-dihydro-2H-pyran-3-yl)methoxy)phenyl) butanoate The title compound was prepared in an analogous manner as Example 1 involving the reaction of methyl 4-(4-((4-bromo-5,6-dihydro-2H-pyran-3-yl)methoxy)phenyl)butanoate (0.150. g, 0.406 mmol) with (5-methylthiophen-2-yl)boronic acid (0.173 g, 1.219 mmol) and potassium carbonate (0.225 g, 1.625 mmol) in the presence of (tetrakistriphenylphosphine) palladium(0) (0.023 g, 0.020 mmol) according to general procedure B (as described herein above). Yield: 76%.
$^1$H NMR (300 MHz, CDCl$_3$) δ: 7.10-7.07 (d, J=8.7 Hz, 2H), 6.83-6.67 (m, 3H), 6.67 (m, 1H), 4.61 (s, 2H), 4.38 (s, 2H), 3.94-3.90 (t, 2H), 3.68 (s, 3H), 2.63-2.58 (t, 2H), 2.53 (bs, 2H), 2.48 (s, 3H), 2.36-2.31 (t, 2H), 1.98-1.88 (m, 2H); Mass: 409.1 (M+23)

Step 61b

Synthesis of 4-(4-((4-(5-methylthiophen-2-yl)-5,6-dihydro-2H-pyran-3-yl)methoxy)phenyl) butanoic Acid The title compound was prepared in an analogous manner as Example 1 involving the reaction of methyl 4-(4-((4-(5-methylthiophen-2-yl)-5,6-dihydro-2H-pyran-3-yl)methoxy) phenyl)butanoate (0.100 g, 0.259 mmol) with LiOH.H$_2$O (1.033 mL, 1.549 mmol), according to general procedure C (as described herein above). Yield: 54.7%.
$^1$H NMR (300 MHz, CDCl$_3$) δ: 7.11-7.08 (d, J=8.7 Hz, 2H), 6.83-6.80 (m, 3H), 6.67 (m, 1H), 4.61 (s, 2H), 4.38 (s, 2H), 3.94-3.90 (t, 2H), 2.65-2.60 (t, 2H), 2.53 (bs, 2H), 2.48 (s, 3H), 2.40-2.35 (t, 2H), 1.97-1.92 (m, 2H)

Example 62

Synthesis of Sodium 4-(4-((4-(p-tolyl)-5,6-dihydro-2H-pyran-3-yl)methoxy)phenyl) butanoate Sodium hydroxide (8.44 mg, 0.205 mmol) and 2-drops of water were added to a solution of 4-(4-((4-(p-tolyl)-5,6-dihydro-2H-pyran-3-yl)methoxy)phenyl)butanoic acid (0.075 g, 0.205 mmol) in anhydrous THF (2 mL) at room temperature. The white precipitate was separated from the reaction mixture after 15 minutes. The reaction mixture was stirred for 12 hours at room temperature, diluted with 4 mL of THF and filtered. The filterate obtained was washed with ethyl acetate (50%) in hexane and dried under vacuum to obtain white crystalline title compound (0.060 g). Yield: 74.6%
$^1$H NMR (300 MHz, DMSO-d$_6$) δ: 7.16 (s, 4H), 7.03-7.00 (d, J=8.1 Hz, 2H), 6.72-6.70 (d, J=8.1 Hz, 2H), 4.33 (s, 2H), 4.23 (s, 2H), 3.81 (t, 2H), 2.45-2.40 (m, 4H), 2.28 (s, 3H), 1.86-1.84 (t, 2H), 1.66-1.64 (m, 2H)

Example 63

Synthesis of Calcium salt of 4-(4-((4-(p-tolyl)-5,6-dihydro-2H-pyran-3-yl)methoxy)phenyl) butanoic Acid Calcium hydroxide (8.09 mg, 0.109 mmol) and 2-drops of water were added to the solution of 4-(4-((4-(p-tolyl)-5,6-dihydro-2H-pyran-3-yl)methoxy)phenyl)butanoic acid (0.080 g, 0.218 mmol) in anhydrous 1,4-Dioxane (2 mL) at room temperature. The reaction mixture was stirred for 3 hours. After the completion of the reaction, white precipitate was separated. The precipitate obtained was filtered, washed with THF (5 mL×2) and dried under vacuum to obtain the title compound (0.060 g). Yield: 68.8%

---

$^1$H NMR (300 MHz, CDCl$_3$): δ 8.38 (s, 2H), 7.10-7.07 (d, J=8.4 Hz, 2H), 6.75-6.72 (d, J=8.4 Hz, 2H), 4.41 (s, 2H), 4.33 (s, 2H), 4.03 (s, 3H), 3.99-3.95 (t, 2H), 2.66-2.61 (t, 2H), 2.46 (bt, 2H), 2.39-2.34 (t, 2H), 2.02-1.94 (m, 2H); Mass: 385.2 (M+1)

¹H NMR (300 MHz, DMSO-d₆) δ: 7.15 (s, 4H), 7.02-7.00 (d, J=8.1 Hz, 2H), 6.72-6.69 (d, J=7.8 Hz, 2H), 4.32 (s, 2H), 4.22 (s, 2H), 3.81 (t, 2H), 2.45-2.40 (m, 4H), 2.27 (s, 3H), 1.92 (t, 2H), 1.66 (m, 2H)

Example 64

Synthesis of Piperazine salt of 4-(4-((4-(p-tolyl)-5,6-dihydro-2H-pyran-3-yl)methoxy) phenyl) butanoic Acid Piperazine (0.0108 g, 0.126 mmol) was added to a solution of 4-(4-((4-(p-tolyl)-5,6-dihydro-2H-pyran-3-yl)methoxy)phenyl)butanoic acid (0.092 g, 0.251 mmol) in anhydrous THF (2 mL) at room temperature. The white precipitate was separated from the reaction mixture after 15 minutes. The reaction mixture was stirred for 12 hours at room temperature, diluted with 4 mL of THF and filtered. The filtrate obtained was washed with ethyl acetate (50%) in hexane and dried under vacuum to obtain the title compound (0.080 g). Yield: 77%
¹H NMR (300 MHz, DMSO-d₆) δ: 7.16 (s, 4H), 7.04-7.01 (d, J=8.4 Hz, 2H), 6.73-6.71 (d, J=8.4 Hz, 2H), 4.32 (s, 2H), 4.22 (s, 2H), 3.80 (t, 2H), 2.70 (s, 4H), 2.45-2.40 (m, 4H), 2.28 (s, 3H), 2.14-2.09 (t, 2H), 1.68-1.61 (m, 2H)

Example 65

Synthesis of Metformin salt of 4-(4-((4-(p-tolyl)-5,6-dihydro-2H-pyran-3-yl)methoxy) phenyl) butanoic Acid Metformin (0.0282 g, 0.218 mmol) was added to a solution of 4-(4-((4-(p-tolyl)-5,6-dihydro-2H-pyran-3-yl)methoxy)phenyl)butanoic acid (0.080 g, 0.218 mmol) in anhydrous THF (2 mL) at room temperature. The white precipitate was separated from the reaction mixture after 15 minutes. The reaction mixture was stirred for 2 hours at room temperature, diluted with 4 mL of THF and filtered. The filtrate obtained was washed with ethyl acetate (50%) in hexane and air dried under vacuum to obtain the title compound (0.070 g). Yield: 67%
¹H NMR (300 MHz, DMSO-d₆) δ: 7.16 (s, 4H), 7.03-7.00 (d, J=8.4 Hz, 2H), 6.73-6.70 (d, J=8.4 Hz, 2H), 4.33 (s, 2H), 4.23 (s, 2H), 3.83 (t, 2H), 2.90 (s, 6H), 2.45-2.40 (m, 4H), 2.28 (s, 3H), 1.86-1.82 (t, 2H), 1.68-1.61 (m, 2H); Mass: 365.1 (M−1, FB mass)

Example 66

Synthesis of 3-(4-((2-(5,6,7,8-tetrahydronaphthalen-2-yl)cyclohept-1-en-1-yl)methoxy) phenyl)propanoic Acid Step 66a Synthesis of Methyl 3-(4-((2-bromocyclohept-1-en-1-yl)methoxy)phenyl)propanoate 1-bromo-2-(bromomethyl)cyclohept-1-ene (1.487 g, 5.55 mmol) and methyl 3-(4-hydroxyphenyl)propanoate (1.0 g, 5.55 mmol) were stirred in acetonitrile (10 mL). Cesium carbonate (2.71 g, 8.32 mol) was added and the reaction mixture was stirred at room temperature for overnight. After the completion of the reaction, reaction mixture was filtered and washed with acetonitrile (30 mL), the filtrate obtained was concentrated. The crude reaction mass obtained was purified using ethyl acetate/pet ether to obtain the title compound (1.1 g). Yield: 54%.
¹H NMR (300 MHz, CDCl₃): δ 7.12-7.09 (d, J=8.7 Hz, 2H), 6.86-6.83 (d, J=8.7 Hz, 2H), 4.64 (s, 2H), 3.67 (s, 3H), 2.9-2.87 (t, 2H), 2.82-2.78 (m, 2H), 2.63-2.58 (t, 2H), 2.37-2.33 (m, 2H), 1.92-1.88 (t, 2H), 1.74-1.70 (m, 2H), 1.62-1.58 (m, 2H), 1.49-1.44 (m, 2H); Mass: 390.3 (M+23)

Step 66b

Synthesis of methyl 3-(4-((2-(5,6,7,8-tetrahydronaphthalen-2-yl)cyclohept-1-en-1-yl)methoxy) phenyl)propanoate The title compound was prepared in an analogous manner as Example 1 involving the reaction of methyl 3-(4-((2-bromocyclohept-1-en-1-yl)methoxy)phenyl)propanoate (0.150 g, 0.408 mmol) with (5,6,7,8-tetrahydronaphthalen-2-yl)boronic acid (0.108 g, 0.613 mmol) and sodium bicarbonate (0.086 g, 1.021 mmol) in the presence of (tetrakistriphenylphosphine) palladium(0) (0.024 g, 0.020 mmol) according to general procedure B (as described herein above). Yield: 41%.
¹H NMR (DMSO-d₆, 300 MHz): δ 7.05-6.95 (m, 3H), 6.84-6.81 (d, J=9.0 Hz, 2H), 6.69-6.66 (d, J=10.8 Hz, 2H), 4.27 (s, 2H), 3.54 (s, 3H), 2.75-2.71 (m, 2H), 2.62-2.56 (m, 4H), 2.54-2.50 (m, 2H), 2.49-2.40 (m, 2H), 2.34-2.28 (m, 2H), 1.77 (bs, 2H), 1.69 (bs, 4H), 1.50-1.40 (m, 4H)

Step 66c

Synthesis of 3-(4-((2-(5,6,7,8-tetrahydronaphthalen-2-yl)cyclohept-1-en-1-yl)methoxy) phenyl) propanoic Acid The title compound was prepared in an analogous manner as Example 1 involving the reaction of methyl 3-(4-((2-(5,6,7,8-tetrahydronaphthalen-2-yl)cyclohept-1-en-1-yl)methoxy)phenyl)propanoate (0.050 g, 0.119 mmol) with LiOH.H₂O (0.478 mL, 0.717 mmol), according to general procedure C (as described herein above). Yield: 47.6%.
¹H NMR (500 MHz, DMSO-d₆): δ 12.17 (s, 1H), 7.06-7.04 (d, J=8.5 Hz, 2H), 6.99-6.97 (d, J=8.0 Hz, 1H), 6.85-6.83 (m, 2H), 6.69-6.68 (d, J=8.5 Hz, 2H), 4.28 (s, 2H), 2.75-2.64 (m, 6H), 2.50-2.43 (m, 4H), 2.34-2.28 (m, 2H), 1.78-1.77 (bs, 2H), 1.70 (bs, 4H), 1.57 (bs, 2H), 1.51 (bs, 2H); Mass 427.2 (M+23).

Example 67

Synthesis of 3-(4-((2-(p-tolyl)cyclohept-1-en-1-yl) methoxy)phenyl)propanoic Acid Step 67a Synthesis of Methyl 3-(4-((2-(p-tolyl)cyclohept-1-en-1-yl)methoxy)phenyl)propanoate The title compound was prepared in an analogous manner as Example 1 involving the reaction of methyl 3-(4-((2-bromocyclohept-1-en-1-yl)methoxy)phenyl)propanoate (0.150 g, 0.408 mmol) with p-tolylboronic acid (0.083 g, 0.613 mmol) and sodium bicarbonate (0.086 g, 1.021 mmol) in the presence of (tetrakistriphenylphosphine) palladium(0) (0.024 g, 0.020 mmol) according to general procedure B (as described herein above).

¹H NMR (DMSO-d₆, 300 MHz): δ 7.13-7.10 (d, J=7.8 Hz, 2H), 7.04-7.01 (d, J=8.1 Hz, 4H), 6.67-6.64 (d, J=8.4 Hz, 2H), 4.26 (s, 2H), 3.54 (s, 3H), 2.75-2.70 (t, 2H), 2.56-2.50 (t, 2H), 2.49-2.46 (m, 2H), 2.38-2.34 (m, 2H), 2.26 (s, 3H), 1.77 (bs, 2H), 1.60-1.40 (bm, 4H); Mass: 401.7 (M+23)

Step 67b

Synthesis of 3-(4-((2-(p-tolyl)cyclohept-1-en-1-yl)methoxy)phenyl)propanoic Acid The title compound was prepared in an analogous manner as Example 1 involving the reaction of Methyl 3-(4-((2-(p-tolyl)cyclohept-1-en-1-yl)methoxy)phenyl)propanoate (0.040 g, 0.106 mmol) with LiOH.H₂O (0.423 mL, 0.717 mmol), according to general procedure C (as described herein above). Yield: 62.3%.
¹H NMR (500 MHz, DMSO-d₆): δ 12.10 (bs, 1H), 7.14-7.12 (d, J=8.0 Hz, 2H), 7.05-7.04 (d, J=7.0 Hz, 4H), 6.68-6.66 (d, J=8.5 Hz, 2H), 4.27 (s, 2H), 2.72-2.69 (m, 2H), 2.48-2.43 (m, 4H), 2.39-2.37 (t, 2H), 2.27 (s, 3H), 1.78 (m, 2H), 1.58 (bm, 2H), 1.51 (bm, 2H); Mass: 387.40 (M+23).

Example 68

Synthesis of 3-(4-((2-(4-cyclopropylphenyl)cyclohept-1-en-1-yl)methoxy)phenyl)propanoic Acid Step 68a Synthesis of methyl 3-(4-((2-(4-cyclopropylphenyl)cyclohept-1-en-1-yl)methoxy) phenyl) propanoate The title compound was prepared in an analogous manner as Example 1 involving the reaction of methyl 3-(4-((2-bromocyclohept-1-en-1-yl)methoxy)phenyl)propanoate (0.150 g, 0.408 mmol) with (4-cyclopropylphenyl)boronic acid (0.099 g, 0.613 mmol) and sodium bicarbonate (0.086 g, 1.021 mmol) in the presence of (tetrakistriphenylphosphine) palladium(0) (0.024 g, 0.020 mmol) according to general procedure B (as described herein above). Yield: 39.3%.
¹H NMR (DMSO-d₆, 300 MHz): δ 7.04-7.01 (bs, 6H), 6.67-6.65 (d, J=8.1 Hz, 2H), 4.26 (s, 2H), 3.54 (s, 3H), 2.75-2.70 (t, 2H), 2.56-2.50 (t, 2H), 2.49-2.46 (m, 2H), 2.38-2.34 (m, 2H), 1.86 (m, 1H), 1.77 (bs, 2H), 1.60-1.40 (bm, 4H), 0.92-0.86 (m, 2H), 0.64-0.62 (m, 2H); Mass: 427.6 (M+23).

Step 68b

Synthesis of 3-(4-((2-(4-cyclopropylphenyl)cyclohept-1-en-1-yl)methoxy)phenyl)propanoic Acid The title compound was prepared in an analogous manner as Example 1 involving the reaction of methyl 3-(4-((2-(4-cyclopropylphenyl)cyclohept-1-en-1-yl)methoxy) phenyl) propanoate (0.050 g, 0.124 mmol) with LiOH.H₂O (0.494 mL, 0.742 mmol), according to general procedure C (as described herein above). Yield: 54%.
¹H NMR (500 MHz, DMSO-d₆): δ 7.06-7.03 (bs, 6H), 6.68-6.67 (d, J=8.1 Hz, 2H), 4.27 (s, 2H), 2.72-2.69 (t, 2H), 2.58-2.44 (m, 4H), 2.38-2.36 (m, 2H), 1.90-1.86 (m, 1H), 1.78 (bs, 2H), 1.57 (bt, 2H), 1.51 (bt, 2H), 1.27-1.24 (m, 2H), 1.19-1.17 (m, 2H); Mass: 413.4 (M+23)

Example 69

Synthesis of 3-(4-((2-(4-(1-cyanocyclopropyl)phenyl)cyclohept-1-en-1-yl)methoxy)phenyl) propanoic Acid Step 69a Synthesis of methyl 3-(4-((2-(4-(1-cyanocyclopropyl)phenyl)cyclohept-1-en-1-yl)methoxy) phenyl) propanoate The title compound was prepared in an analogous manner as Example 1 involving the reaction of methyl 3-(4-((2-bromocyclohept-1-en-1-yl)methoxy)phenyl)propanoate (0.150 g, 0.408 mmol) with (4-(1-cyanocyclopropyl)phenyl) boronic acid (0.115 g, 0.613 mmol) and sodium bicarbonate (0.086 g, 1.021 mmol) in the presence of (tetrakistriphenylphosphine) palladium(0) (0.024 g, 0.020 mmol) according to general procedure B (as described herein above). Yield: 37%.
¹H NMR (300 MHz, DMSO-d₆): δ 7.28-7.25 (d, J=8.1 Hz, 2H), 7.17-7.14 (d, J=8.4 Hz, 2H), 7.05-6.97 (m, 2H), 6.69-6.66 (d, J=8.4 Hz, 2H), 4.25 (s, 2H), 3.54 (s, 3H), 2.75-2.70 (t, 2H), 2.56-2.50 (t, 2H), 2.49-2.46 (m, 2H), 2.39-2.34 (m, 2H), 1.78-1.70 (m, 4H), 1.57-1.46 (m, 6H); Mass: 452.9 (M+23)

Step 69b

Synthesis of 3-(4-((2-(4-(1-cyanocyclopropyl)phenyl)cyclohept-1-en-1-yl)methoxy)phenyl) propanoic Acid The title compound was prepared in an analogous manner as Example 1 involving the reaction of methyl 3-(4-((2-(4-(1-cyanocyclopropyl)phenyl)cyclohept-1-en-1-yl)methoxy) phenyl)propanoate (0.035 g, 0.081 mmol) with LiOH.H₂O (0.325 mL, 0.489 mmol), according to general procedure C (as described herein above). Yield: 62%.
¹H NMR (500 MHz, DMSO-d₆): δ 7.06-7.03 (bs, 6H), 6.68-6.67 (d, J=8.1 Hz, 2H), 4.27 (s, 2H), 2.72-2.69 (t, 2H), 2.58-2.44 (m, 4H), 2.38-2.36 (m, 2H), 1.90-1.86 (m, 1H), 1.78 (bs, 2H), 1.57 (bt, 2H), 1.51 (bt, 2H), 1.27-1.24 (m, 2H), 1.19-1.17 (m, 2H); Mass: 413.4 (M+23).

Example 70

Synthesis of 4-(5-((4'-methyl-3,4,5,6-tetrahydro-[1,1'-biphenyl]-2-yl)methoxy)pyridin-2-yl)butanoic Acid Step 70a Synthesis of 4'-methyl-3,4,5,6-tetrahydro-[1,1'-biphenyl]-2-carbaldehyde 2-Bromocyclohexe-1-carbaldehyde (1.0 g, 5.29 mmol), p-tolyl boronic acid (1.079 g, 7.93 mmol) and potassium carbonate (1.82 g, 13.22 mmol) were stirred in dioxane:water (4:1) mixture and purged with argon for 5 minutes. (Tetrakistriphenylphosphine)palladium(0) (0.306 g, 0.264 mmol) was added and stirred at 110° C. for 5 hours. The reaction mixture was cooled, diluted with ethyl acetate and filtered through celite. The filtrate obtained was concentrated. The crude product was purified by column chromatography using Ethyl acetate/Pet ether to obtain the title compound (0.875 g). Yield: 82%.

$^1$H NMR (300 MHz, CDCl$_3$): δ 9.51 (s, 1H), 7.22-7.19 (d, J=8.1, 2H), 7.15-7.12 (d, J=7.8 Hz, 2H), 2.57-2.53 (m, 2H), 2.40-2.36 (m, 5H), 1.83-1.73 (m, 4H).

Step 70b

Synthesis of (4'-methyl-3,4,5,6-tetrahydro-[1,1'-biphenyl]-2-yl)methanol

Methyl 4-(p-tolyl)-5,6-dihydro-2H-pyran-3-carbaldehyde (0.800 g, 4.00 mmol) was stirred in methanol at 0° C. Sodium borohydride (0.076 g, 2.00 mmol) was added in small quantity over a period of 10 minutes. The reaction mixture was stirred for 4 hours, concentrated and poured over crushed ice, neutralized with 2N HCl solution and extracted thrice with dichloromethane (75 mL). Organic layer obtained was washed with brine and dried over sodium sulfate and concentrated to obtain the title product (0.400 g). Yield: 50.7%.

$^1$H NMR (300 MHz, CDCl$_3$): δ 7.16-7.14 (d, J=7.5, 2H), 7.07-7.04 (d, J=7.8 Hz, 2H), 3.96 (s, 2H), 2.30 (s, 3H), 2.28 (bs, 4H), 1.74 (bs, 4H).

Step 70c

Synthesis of 6-(bromomethyl)-4'-methyl-2,3,4,5-tetrahydro-1,1'-biphenyl (4'-methyl-3,4,5,6-tetrahydro-[1,1'-biphenyl]-2-yl)methanol (0.150 g, 0.742 mmol) was stirred in dry DCM (10 mL). Catalytic amount of pyridine (7.87 mg, 0.099 mmol) was added to it and stirred at 0° C. Phosphorous tribromide (0.100 g, 0.371 mmol) was slowly added and stirred at same temperature for 3 hours. The reaction mixture was diluted with dichloromethane and washed with saturated solution of sodium bicarbonate and brine. Organic layer obtained was dried over sodium sulfate and concentrated (0.177 g). Yield: 90%.

Step 70d

Synthesis of 5-(benzyloxy)-2-bromopyridine

A mixture of Benzylbromide (3.24, 18.97 mmol), 6-bromopyridin-3-ol (3 g, 17.24 mmol) and cesium carbonate (8.43 g, 25.90 mmol) in dry acetonitrile (50 mL) was stirred overnight at room temperature. After completion of the reaction, the reaction mixture was diluted with ethyl acetate (80 mL) and filtered. The filtrate was concentrated under vacuum to give the title compound (4.05). Yield: 89%

$^1$H NMR (300 MHz, CDCl$_3$): δ 8.15 (s, 1H), 7.42-7.37 (m, 5H), 7.19-7.15 (m, 1H), 5.11 (s, 2H).

Step 70e

Synthesis of ethyl 4-(5-(benzyloxy)pyridin-2-yl)butanoate 5-(Benzyloxy)-2-bromopyridine (3.00 g, 11.36 mmol) was stirred in dry THF under argon atmosphere. A 0.5M solution of (4-ethoxy-4-oxobutyl)zinc(II) bromide in THF (25 mL, 12.49 mmol) was added carefully. After complete addition of (4-ethoxy-4-oxobutyl)zinc(II) bromide PEPPSI-IPr catalyst (0.386 mmol, 0.568 mmol) was added and reaction stirred at RT overnight. Reaction mixture was decomposed with saturated solution of ammonium chloride (50 mL) and extracted with ethyl acetate (3×100 mL). Organic layer washed with brine, dried and concentrated. The crude product was purified over silica gel using ethyl acetate/pet ether as eluent to obtain ethyl 4-(5-(benzyloxy) pyridin-2-yl)butanoate (2.2 g). Yield: 64%

$^1$H NMR (300 MHz, CDCl$_3$): δ 8.31 (m, 1H), 7.45-7.34 (m, 5H), 7.22-7.18 (m, 1H), 7.09-7.07 (d, J=8.4 Hz, 1H), 5.10 (s, 2H), 4.17-4.10 (q, 2H), 2.81-2.76 (t, 2H), 2.38-2.33 (t, 2H), 2.10-2.00 (m, 2H), 1.28 (t, 3H).

Step 70f

Synthesis of ethyl 4-(5-hydroxypyridin-2-yl)butanoate

Ethyl 4-(5-(benzyloxy)pyridin-2-yl)butanoate (0.370 g, 1.23 mmol) was suspended in ethanol (15 mL). Palladium over carbon (7 mg) was added very carefully to the mixture and the reaction mixture was set for hydrogenation at 40 psi for 3 hours. Reaction mixture filtered through celite washed with 15 mL ethanol and concentrated to give required product (0.22 g).

Yield: 85%

$^1$H NMR (300 MHz, CDCl$_3$): δ 8.22 (m, 1H), 7.25-7.23 (m, 1H), 7.13-7.10 (d, J=8.4 Hz, 1H), 4.16-4.09 (q, 2H), 2.82-2.77 (t, 2H), 2.378-2.33 (t, 2H), 2.04-2.00 (m, 2H), 1.27 (t, 3H).

Step 70 g

Synthesis of Ethyl 4-(5-((4'-methyl-3,4,5,6-tetrahydro-[1,1'-biphenyl]-2-yl)methoxy)pyridin-2-yl) butanoate A mixture of compound obtained in step 70c, 6-(bromomethyl)-4'-methyl-2,3,4,5-tetrahydro-1,1'-biphenyl (0.150 g, 0.566 mmol) and Cesium carbonate (0.276 g, 0.848 mmol) was stirred in dry acetonitrile. To the mixture was then added ethyl 4-(5-hydroxypyridin-2-yl)butanoate (0.118 g, 0.566 mmol) and stirred overnight. The reaction mixture was diluted with ethyl acetate and filtered. The filtrate obtained was concentrated and purified over silica gel using ethyl acetate/pet ether as eluent (0.160 g).

Yield: 72%.

$^1$H NMR (300 MHz, CDCl$_3$): δ 8.14 (d, 1H), 7.15-7.06 (m, 4H), 6.99 (bs, 2H), 4.36 (s, 2H), 4.14-4.12 (m, 2H), 2.78-2.73 (t, 2H), 2.35-2.28 (m, 7H), 2.05-2.00 (t, 2H), 1.76 (bs, 4H), 1.66-1.61 (t, 2H), 1.28-1.23 (m, 3H); Mass: 394.2 (M+1)

Step 70 h

Synthesis of 4-(5-((4'-methyl-3,4,5,6-tetrahydro-[1,1'-biphenyl]-2-yl)methoxy)pyridin-2-yl)butanoic Acid The title compound was prepared in an analogous manner as Example 1 involving the reaction of ethyl 4-(5-((4'-methyl-3,4,5,6-tetrahydro-[1,1'-biphenyl]-2-yl)methoxy) pyridin-2-yl)butanoate (0.100 g, 0.254 mmol) in THF with LiOH.H$_2$O (1.017 mL, 1.525 mmol) at to afford the title compound (0.024 g).

$^1$H NMR (300 MHz, CDCl$_3$): δ 8.07 (d, 1H), 7.17-7.05 (m, 6H), 4.39 (s, 2H), 2.92-2.88 (t, 2H), 2.41-2.36 (m, 7H), 2.27 (bs, 2H), 2.06-2.01 (t, 2H), 1.76 (bs, 4H); Mass: 366.1 (M+1), 364.1 (M−1).

Example 71

Synthesis of 4-(5-((3,4,5,6-tetrahydro-[1,1'-biphenyl]-2-yl)methoxy)pyridin-2-yl)butanoic Acid

Step 71a

Synthesis of 3,4,5,6-tetrahydro-[1,1'-biphenyl]-2-carbaldehyde

The compound 2-bromocyclohex-1-enecarbaldehyde (1.0 g, 5.29 mmol), phenylboronic acid (0.967 g, 7.93 mmol) and potassium carbonate (1.82 g, 13.22 mmol) were stirred in dioxane: water (4:1) mixture and purged with argon for 5 minutes. (Tetrakistriphenylphosphine)palladium(0) (0.306 g, 0.264 mmol) was added and stirred at 110° C. for 5 hours. Reaction mixture cooled diluted with ethyl acetate and filtered through celite. The filtrate obtained was concentrated. The crude product was purified by column chromatography using Ethyl acetate/Pet ether as eluent to obtain the title compound (0.900 g). Yield: 99%.

$^1$H NMR (300 MHz, CDCl$_3$): δ 9.50 (s, 1H), 7.40-7.38 (m, 3H), 7.26-7.23 (m, 2H), 2.56-2.54 (m, 2H), 2.39-2.37 (m, 2H), 1.84-1.72 (m, 4H).

Step 71b

Synthesis of (3,4,5,6-tetrahydro-[1,1'-biphenyl]-2-yl)methanol

Compound 3,4,5,6-tetrahydro-[1,1'-biphenyl]-2-carbaldehyde (0.870 g, 4.67 mmol) was stirred in Methanol at 0° C. Sodium borohydride (0.088 g, 2.34 mmol) was added in small lots over a period of 10 min. The reaction mixture was stirred for 4 hours, concentrated, poured over crushed ice, neutralized with 2N HCl solution and extracted thrice with dichloromethane (75 mL). The organic layer obtained was washed with brine and dried over sodium sulfate and concentrated to obtain (3,4,5,6-tetrahydro-[1,1'-biphenyl]-2-yl)methanol (0.830 g). Yield: 97%.

$^1$H NMR (300 MHz, CDCl$_3$): δ 7.40-7.32 (m, 3H), 7.18-7.15 (m, 2H), 3.96 (s, 2H), 2.29 (bs, 4H), 1.76 (bs, 4H).

Step 71c

Synthesis of 6-(bromomethyl)-2,3,4,5-tetrahydro-1,1'-biphenyl

Compound (3,4,5,6-tetrahydro-[1,1'-biphenyl]-2-yl)methanol (0.200 g, 1.062 mmol) was stirred in dry DCM (10 mL). Catalytic amount of pyridine (7.87 mg, 0.099 mmol) was added and stirred at 0° C. Phosphorous tribromide (0.144 g, 0.531 mmol) was slowly added and stirred at same temperature for 3 hours. The reaction mixture was diluted with dichloromethane and washed with saturated solution of sodium bicarbonate and brine. Organic layer obtained was dried over sodium sulfate and concentrated to obtain the title compound (0.200 g). Yield: 75%

Step 71d

Synthesis of 5-(benzyloxy)-2-bromopyridine

A mixture of benzylbromide (3.24 g, 18.97 mmol), 6-bromopyridin-3-ol (3 g, 17.24 mmol) and cesium carbonate (8.43 g, 25.90 mmol) in dry acetonitrile (50 mL) was stirred overnight at room temperature. After completion of the reaction, the reaction mixture was diluted with ethyl acetate (80 mL) and filtered. The filtrate obtained was concentrated under vacuum to give the title compound (4.05 g). Yield: 89%.

$^1$H NMR (300 MHz, CDCl$_3$): δ 8.15 (s, 1H), 7.42-7.37 (m, 5H), 7.19-7.15 (m, 1H), 5.11 (s, 2H).

Step 71e

Synthesis of ethyl 4-(5-(benzyloxy)pyridin-2-yl)butanoate

The compound obtained in step 71d, 5-(benzyloxy)-2-bromopyridine (3.00 g, 11.36 mmol) was stirred in dry THF under argon atmosphere. A 0.5M solution of (4-ethoxy-4-oxobutyl)zinc(II) bromide in THF (25 mL, 12.49 mmol) was added carefully. After complete addition of (4-ethoxy-4-oxobutyl)zinc(II) bromide PEPPSI-IPr catalyst (0.386 mmol, 0.568 mmol) was added and the reaction was stirred at RT for overnight. The reaction mixture was decomposed with saturated solution of ammonium chloride (50 mL) and extracted with ethyl acetate (3×100 mL). Organic layer obtained was washed with brine, dried and concentrated. The crude product was purified over silica gel using ethyl acetate/pet ether as eluent to obtain the title compound (2.2 g). Yield: 64%

$^1$H NMR (300 MHz, CDCl$_3$): δ 8.31 (m, 1H), 7.45-7.34 (m, 5H), 7.22-7.18 (m, 1H), 7.09-7.07 (d, J=8.4 Hz, 1H), 5.10 (s, 2H), 4.17-4.10 (q, 2H), 2.81-2.76 (t, 2H), 2.38-2.33 (t, 2H), 2.10-2.00 (m, 2H), 1.28 (t, 3H).

Step 71f

Synthesis of ethyl 4-(5-hydroxypyridin-2-yl)butanoate

The compound obtained in step 71e, ethyl 4-(5-(benzyloxy)pyridin-2-yl)butanoate (0.370 g, 1.23 mmol) was suspended in ethanol (15 mL). Palladium over carbon (7 mg) was added to the mixture and the reaction mixture was set for hydrogenation at 40 psi for 3 hours. The reaction mixture was filtered through celite washed with 15 mL ethanol and concentrated to obtain the title compound (0.220 g). Yield: 85%

$^1$H NMR (300 MHz, CDCl$_3$): δ 8.22 (m, 1H), 7.25-7.23 (m, 1H), 7.13-7.10 (d, J=8.4 Hz, 1H), 4.16-4.09 (q, 2H), 2.82-2.77 (t, 2H), 2.378-2.33 (t, 2H), 2.04-2.00 (m, 2H), 1.27 (t, 3H).

Step 71 g

Synthesis of ethyl 4-(5-((3,4,5,6-tetrahydro-[1,1'biphenyl]-2-yl) methoxy)pyridine-2-yl) butanoate A mixture obtained in step 71c, 6-(bromomethyl)-2,3,4,5-tetrahydro-1,1'-biphenyl (0.200 g, 0.796 mmol) and Cesium carbonate (0.389 g, 1.14 mmol) were stirred in dry acetonitrile. To the reaction mixture ethyl 4-(5-hydroxypyridin-2-yl)butanoate (0.167 g, 0.796 mmol) was added and stirred overnight. The reaction mixture was diluted with ethyl acetate and filtered. The filtrate obtained was concentrated and purified over silica gel using ethyl acetate/pet ether as eluent to obtain the title compound (0.128 g). Yield: 90%.

$^1$H NMR (300 MHz, CDCl$_3$): δ 8.13 (m, 1H), 7.40-7.24 (m, 3H), 7.19-7.17 (m, 2H), 7.02-6.99 (m, 2H), 4.35 (s, 2H), 4.16-4.09 (q, 2H), 2.78-2.73 (t, 2H), 2.36-2.30 (t, 6H), 2.08-2.00 (m, 2H), 1.77 (bs, 4H), 1.28 (t, 3H); Mass: 380.1 (M+1).

Step 71 h

Synthesis of 4-(5-((3,4,5,6-tetrahydro-[1,1'-biphenyl]-2-yl)methoxy)pyridin-2-yl)butanoic Acid The title compound was prepared in an analogous manner as Example 1 involving the reaction of ethyl 4-(5-((3,4,5,6-tetrahydro-[1,1'biphenyl]-2-yl) methoxy)pyridine-2-yl) butanoate. (0.175 g, 0.461 mmol) in THF with LiOH.H$_2$O (1.906 mL, 2.86 mmol) to obtain the title compound (0.152 g). Yield: 87%.

$^1$H NMR (300 MHz, CDCl$_3$): δ 8.07 (m, 1H), 7.34-7.28 (m, 3H), 7.18-7.16 (m, 2H), 7.10 (m, 2H), 4.38 (s, 2H), 2.90-2.88 (t, 2H), 2.36-2.28 (t, 6H), 2.03-2.00 (m, 2H), 1.77 (bs, 4H); Mass: 352.1 (M+1)

Biological Assays

Representative compounds of Formula (I) of the present invention (referred to as test compounds) were tested for their activity using the assays and the methods described below Beta (β) arrestin 2 Interaction Assay (BRET assay) was performed using CHO-K1 cells stably expressing the GPR120 receptor using β-galactosidase (Beta gal) enzyme fragment complementation assay. The measurement of GPR120 activation upon agonist activation was directly provided by β-arrestin recruitment. One day before the β-arrestin 2 assay, CHO-K1 cells were seeded and incubated overnight at 37° C. in a 5% CO$_2$ humidified atmosphere. Cells were treated with the test compounds in the various concentrations ranging from 30 μM to 1 nM and incubated for 2 hours for GPCR (GPR120) activation. Extent of Arrestin recruitment was measured by adding detection reagents for Beta gal complementation assay and was further incubated for 1 hour. The chemi-luminescent signal was detected on Polar Star (BMG Labtech). The dose-response curve was analyzed using Sigma Plot/Graph Pad. The EC$_{50}$ (concentration of the test compounds where 50% of compounds' maximal activity is observed) values were calculated from the dose-response curve.

TABLE 1

EC$_{50}$ values of compounds of Examples

| Compound of Example No. | EC$_{50}$ (nM) |
| --- | --- |
| Compound of Example 1 | ++ |
| Compound of Example 4 | ++ |
| Compound of Example 6 | ++ |
| Compound of Example 7 | +++ |
| Compound of Example 8 | ++ |
| Compound of Example 9 | +++ |
| Compound of Example 10 | ++ |
| Compound of Example 14 | ++ |
| Compound of Example 15 | +++ |
| Compound of Example 21 | ++ |
| Compound of Example 22 | +++ |
| Compound of Example 48 | ++ |
| Compound of Example 49 | ++ |
| Compound of Example 50 | ++ |
| Compound of Example 53 | ++ |
| Compound of Example 54 | ++ |

The EC$_{50}$ (nM) values of the compounds are presented in Table 1 wherein:
+++ corresponds to EC$_{50}$ ranging from 50 nM to 500 nM;
++ corresponds to EC$_{50}$ ranging from 500 nM to 5000 nM;
+ corresponds to EC$_{50}$ ranging from 5000 nM to 10000 nM;

Conclusion: The EC$_{50}$ values determined for the compounds of the present invention is indicative of GPR120 agonist activity of the compounds of the present invention.

We claim:
1. A compound of Formula (I)

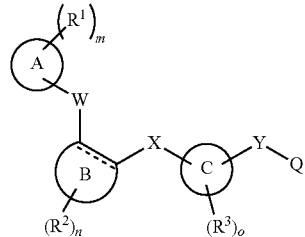

Formula (I)

or a tautomer, a stereoisomer, a geometrical isomer, a pharmaceutically acceptable salt, a prodrug, an N-oxide, a S-oxide or a carboxylic acid isostere thereof;
wherein:
Ring A is 5- to 12-membered carbocycle, 5- to 12-membered heterocyclyl; (C$_6$-C$_{10}$)aryl, or 5- to 12-membered heteroaryl; provided that when q is 1 or 2, and W is a bond, then (C$_6$-C$_{10}$)aryl excludes naphthyl;
Ring B is 5- to 12-membered carbocycle;
Ring C is (C$_6$-C$_{10}$)aryl;
W represents a bond, —(CR$^5$R$^6$)$_p$—, —O—, —S— or —NR$^7$—;
X is —CR$^5$R$^6$—X$^1$— or —X$^1$—CR$^5$R$^6$—, wherein X$^1$ is O, S or NR$^7$
Y is —(C(R$^4$)$_2$)$_q$—;
Q is —CO$_2$M, —CONH$_2$, —CONH[(C$_1$-C$_6$)alkyl], —CON[(C$_1$-C$_6$)alkyl]$_2$, —CONHSO$_2$(C$_1$-C$_6$)alkyl or a carboxylic acid isostere;
M is hydrogen, deuterium or (C$_1$-C$_6$)alkyl;
------ represents a single bond or a double bond;
R$^1$ at each occurrence is independently selected from the group consisting of hydrogen, halogen, (C$_1$-C$_6$)alkyl, (C$_1$-C$_6$)alkenyl, halo(C$_1$-C$_6$)alkyl, (C$_1$-C$_6$)alkoxy, hydroxy, (C$_3$-C$_{10}$)cycloalkyl, heterocyclyl, (C$_6$-C$_{10}$) aryl, heteroaryl, (C$_6$-C$_{10}$)aryloxy, cyano, oxo, —NR$^7$R$^8$, —C(O)NR$^7$R$^8$, —C(S)NR$^7$R$^8$, —S(O)$_r$R$^9$ and —C(O)R$^{10}$;
R$^2$ at each occurrence is independently selected from the group consisting of hydrogen, halogen, (C$_1$-C$_6$)alkyl, (C$_1$-C$_6$)alkenyl, halo(C$_1$-C$_6$)alkyl, (C$_1$-C$_6$)alkoxy, hydroxy, (C$_3$-C$_{10}$)cycloalkyl, heterocyclyl, (C$_6$-C$_{10}$) aryl, heteroaryl, (C$_6$-C$_{10}$)aryloxy, cyano, oxo, —NR$^7$R$^8$, —C(O)NR$^7$R$^8$, —C(S)NR$^7$R$^8$, —S(O)$_r$R$^9$ and —C(O)R$^{10}$;
R$^3$ at each occurrence is independently selected from the group consisting of hydrogen, halogen, (C$_1$-C$_6$)alkyl, (C$_1$-C$_6$)alkoxy, hydroxy, (C$_3$-C$_{10}$)cycloalkyl, heterocyclyl, (C$_6$-C$_{10}$)aryl, heteroaryl, cyano, –NR$^7$R$^8$, —S(O)$_r$R$^9$ and —C(O)R$^{10}$;
R$^4$ at each occurrence is independently selected from the group consisting of hydrogen, (C$_1$-C$_6$)alkyl, halo(C$_1$-C$_6$)alkyl and halogen; or
two R$^4$ groups, together with the carbon atom to which they are attached can combine to form a (C$_3$-C$_{10}$) cycloalkyl or heterocyclyl;
R$^5$ and R$^6$ are independently selected from the group consisting of hydrogen, deuterium, (C$_1$-C$_6$)alkyl, halo (C$_1$-C$_6$)alkyl and halogen; or R$^5$ and R$^6$ together with the carbon atom to which they are attached can combine to form
i) 5- to 12-membered carbocycle or
ii) 5- to 12-membered heterocyclyl containing 1, 2, 3 or 4 heteroatoms independently selected from the group consisting of N, O and S;

R$^7$ and R$^8$ are independently selected from the group consisting of hydrogen, hydroxy, (C$_1$-C$_6$)alkyl, (C$_1$-C$_6$)alkenyl, halo(C$_1$-C$_6$)alkyl, (C$_1$-C$_6$)alkoxy, (C$_3$-C$_{10}$)cycloalkyl, heterocyclyl, (C$_6$-C$_{10}$)aryl, heteroaryl, (C$_6$-C$_{10}$)aryloxy, —S(O)$_t$R$^9$; or R$^7$ and R$^8$, together with the nitrogen atom to which they are attached combine to form heterocyclyl;

R$^9$ and R$^{10}$ are independently selected from the group consisting of hydrogen, hydroxy, (C$_1$-C$_6$)alkyl, halo(C$_1$-C$_6$)alkyl, (C$_1$-C$_6$)alkoxy, (C$_3$-C$_{10}$)cycloalkyl, heterocyclyl, (C$_6$-C$_{10}$)aryl, heteroaryl and —NR$^7$R$^8$;

m is 0, 1, 2 or 3;
n is 0, 1, 2 or 3;
o is 0, 1 or 2;
p is 1 or 2;
q is 1, 2, 3 or 4;
t is 0, 1 or 2;
wherein:

(C$_1$-C$_6$)alkyl is unsubstituted or substituted with one or more groups independently selected from the group consisting of (C$_1$-C$_6$)alkyl, (C$_1$-C$_6$)alkenyl, halogen, halo(C$_1$-C$_6$)alkyl, hydroxy, (C$_1$-C$_6$)alkoxy, halo(C$_1$-C$_6$)alkoxy, (C$_3$-C$_{10}$)cycloalkyl, (C$_6$-C$_{10}$)aryl, (C$_6$-C$_{10}$)aryloxy, heterocyclyl, heteroaryl, amino, cyano, nitro, —NH(C$_1$-C$_6$)alkyl, —N[(C$_1$-C$_6$)alkyl]$_2$, —C(O)(C$_1$-C$_6$)alkyl, —C(O)O(C$_1$-C$_6$)alkyl, —C(O)NH$_2$, —C(O)NH(C$_1$-C$_6$)alkyl, —C(O)N[(C$_1$-C$_6$)alkyl]$_2$ and —C(O)NHSO$_2$(C$_1$-C$_6$)alkyl;

(C$_3$-C$_{10}$)cycloalkyl is unsubstituted or substituted with one or more groups independently selected from the group consisting of (C$_1$-C$_6$)alkyl, (C$_1$-C$_6$)alkenyl, halogen, halo(C$_1$-C$_6$)alkyl, hydroxy, (C$_1$-C$_6$)alkoxy, halo(C$_1$-C$_6$)alkoxy, amino, cyano and nitro;

carbocycle is a 5- to 12-membered ring which is unsubstituted or substituted with one or more groups independently selected from the group consisting of (C$_1$-C$_6$)alkyl, (C$_1$-C$_6$)alkenyl, halo(C$_1$-C$_6$)alkyl, hydroxy, halogen, (C$_1$-C$_6$)alkoxy, halo(C$_1$-C$_6$)alkoxy, (C$_6$-C$_{10}$)aryl, (C$_3$-C$_{10}$)cycloalkyl, heteroaryl, heterocyclyl, amino, cyano, nitro, —C(O)O(C$_1$-C$_6$)alkyl, —C(O)NR$^7$R$^8$ and —S(O)$_t$R$^9$; wherein R$^7$, R$^8$, R$^9$ and t are as defined above;

heterocyclyl is a 5- to 12-membered ring which is unsubstituted or substituted with one or more groups independently selected from the group consisting of (C$_1$-C$_6$)alkyl, (C$_1$-C$_6$)alkenyl, halogen, halo(C$_1$-C$_6$)alkyl, hydroxy, (C$_1$-C$_6$)alkoxy, halo(C$_1$-C$_6$)alkoxy, (C$_3$-C$_{10}$)cycloalkyl, (C$_6$-C$_{10}$)aryl, heterocyclyl, heteroaryl, amino, cyano, nitro, oxo, —NR$^7$R$^8$, —C(O)NR$^7$R$^8$, —S(O)$_t$R$^9$ and —C(O)R$^{10}$; wherein R$^7$, R$^8$, R$^9$, R$^{10}$ and t are as defined above;

(C$_6$-C$_{10}$)aryl is unsubstituted or substituted with one or more groups independently selected from the group consisting of (C$_1$-C$_6$)alkyl, (C$_1$-C$_6$)alkenyl, halogen, halo(C$_1$-C$_6$)alkyl, hydroxy, (C$_1$-C$_6$)alkoxy, halo(C$_1$-C$_6$)alkoxy, (C$_3$-C$_{10}$)cycloalkyl, (C$_6$-C$_{10}$)aryl, heterocyclyl, heteroaryl, amino, cyano, nitro, —C(O)O(C$_1$-C$_6$)alkyl, —C(O)NR$^7$R$^8$ and —S(O)$_t$R$^9$; wherein R$^7$, R$^8$, R$^9$ and t are as defined above;

heteroaryl is a 5- to 12-membered ring which is unsubstituted or substituted with one or more groups independently selected from the group consisting of (C$_1$-C$_6$)alkyl, (C$_1$-C$_6$)alkenyl, halogen, halo(C$_1$-C$_6$)alkyl, hydroxy, (C$_1$-C$_6$)alkoxy, halo(C$_1$-C$_6$)alkoxy, (C$_3$-C$_{10}$)cycloalkyl, (C$_6$-C$_{10}$)aryl, heterocyclyl, heteroaryl, amino, cyano, nitro, —C(O)NR$^7$R$^8$ and —S(O)$_t$R$^9$; wherein R$^7$, R$^8$, R$^9$ and t are as defined above.

2. The compound according to claim 1, wherein Ring A is 5- to 12-membered carbocycle which is unsubstituted or substituted with one or more groups of R$^1$; wherein R$^1$ is as defined above; or a tautomer, a stereoisomer, a geometrical isomer, a pharmaceutically acceptable salt, a prodrug, an N-oxide, a S-oxide or a carboxylic acid isostere thereof.

3. The compound according to claim 1, wherein Ring A is 5- to 12-membered heterocyclyl containing 1, 2, 3 or 4 heteroatoms independently selected from the group consisting of N, O and S, wherein said heterocyclyl is unsubstituted or substituted with one or more groups of R$^1$, wherein R$^1$ is as defined above; or a tautomer, a stereoisomer, a geometrical isomer, a pharmaceutically acceptable salt, a prodrug, an N-oxide, a S-oxide or a carboxylic acid isostere thereof.

4. The compound according to claim 1, wherein Ring A is (C$_6$-C$_{10}$)aryl; which is unsubstituted or substituted with one or more groups of R$^1$; wherein R$^1$ is as defined above; or a tautomer, a stereoisomer, a geometrical isomer, a pharmaceutically acceptable salt, a prodrug, an N-oxide, a S-oxide or a carboxylic acid isostere thereof.

5. The compound according to claim 1, wherein Ring A is 5- to 12-membered heteroaryl containing 1, 2, 3 or 4 heteroatoms independently selected from the group consisting of N, O and S, wherein said heteroaryl is unsubstituted or which is substituted with one or more groups of R$^1$; wherein R$^1$ is as defined above; or a tautomer, a stereoisomer, a geometrical isomer, a pharmaceutically acceptable salt, a a prodrug, an N-oxide, a S-oxide or a carboxylic acid isostere thereof.

6. The compound according to claim 1, wherein Ring B is saturated or partially unsaturated 5- to 12-membered carbocycle, which is unsubstituted or substituted with one or more groups of R$^2$; wherein R$^2$ is as defined above; or a tautomer, a stereoisomer, a geometrical isomer, a pharmaceutically acceptable salt, a prodrug, an N-oxide, a S-oxide or a carboxylic acid isostere thereof.

7. The compound according to claim 1, wherein Ring C is (C$_6$-C$_{10}$)aryl which is unsubstituted or substituted with one or more groups of R$^3$; wherein R$^3$ is as defined above; or a tautomer, a stereoisomer, a geometrical isomer, a pharmaceutically acceptable salt, a prodrug, an N-oxide, a S-oxide or a carboxylic acid isostere thereof.

8. The compound according to claim 1, wherein W represents a bond.

9. The compound according to claim 1, wherein W is —O—.

10. The compound according to claim 1, wherein Y is —(C(R$^4$)$_2$)$_q$—; q is 1, 2, 3 or 4 and R$^4$ is as defined above.

11. The compound according to claim 1, wherein Y is —(C(R$^4$)$_2$)$_q$—; q is 3 or 4 and R$^4$ is as defined above.

12. The compound according to claim 1, wherein Y is —(C(R$^4$)$_2$)$_q$—; q is 3 and R$^4$ at each occurrence is independently selected from hydrogen or (C$_1$-C$_6$)alkyl.

13. The compound according to claim 1, wherein Q is —CO$_2$M and M is hydrogen or (C$_1$-C$_6$)alkyl.

14. The compound according to claim 1, represented by Formula Ia

Formula Ia

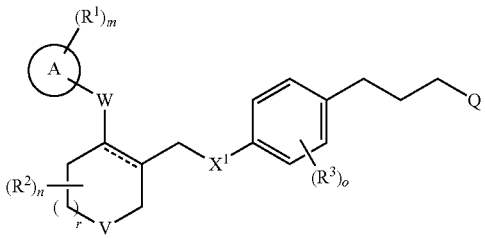

or a tautomer, a stereoisomer, a geometrical isomer, a pharmaceutically acceptable salt, a prodrug, an N-oxide, a S-oxide or a carboxylic acid isostere thereof:
wherein,
Ring A is 5- to 12-membered carbocycle, 5- to 12-membered heterocyclyl, $(C_6-C_{10})$aryl or 5- to 12-membered heteroaryl;
W represents a bond, —O—, —S— or —NR—;
$X^1$ is —O—, —S—, or —NR$^7$—, V is —CR$^5$R$^6$—, —O—, —S— or —NR$^7$—;
Q is —CO$_2$M, —CONH$_2$, —CONH[(C$_1$-C$_6$)alkyl], —CON[(C$_1$-C$_6$)alkyl]$_2$, —CONHSO$_2$(C$_1$-C$_6$)alkyl or a carboxylic acid isostere;
M is hydrogen, deuterium or (C$_1$-C$_6$)alkyl;
------ represents a single bond or a double bond;
wherein,
$R^1$ at each occurrence is independently selected from the group consisting of hydrogen, halogen, (C$_1$-C$_6$)alkyl, (C$_1$-C$_6$)alkenyl, halo(C$_1$-C$_6$)alkyl, (C$_1$-C$_6$)alkoxy, hydroxy, (C$_3$-C$_{10}$)cycloalkyl, heterocyclyl, (C$_6$-C$_{10}$)aryl, heteroaryl, (C$_6$-C$_{10}$)aryloxy, cyano, oxo, —NR$^7$R$^8$, —C(O)NR$^7$R$^8$, —C(S)NR$^7$R$^8$, —S(O)$_r$R$^9$ and —C(O)R$^{10}$;
$R^2$ at each occurrence is independently selected from the group consisting of hydrogen, halogen, (C$_1$-C$_6$)alkyl, (C$_1$-C$_6$)alkenyl, halo(C$_1$-C$_6$)alkyl, (C$_1$-C$_6$)alkoxy, hydroxy, (C$_3$-C$_{10}$)cycloalkyl, heterocyclyl, (C$_6$-C$_{10}$)aryl, heteroaryl, (C$_6$-C$_{10}$)aryloxy, cyano, oxo, —NR$^7$R$^8$, —C(O)NR$^7$R$^8$, —C(S)NR$^7$R$^8$, —S(O)$_r$R$^9$ and —C(O)R$^{10}$;
$R^3$ at each occurrence is independently selected from the group consisting of hydrogen, halogen, (C$_1$-C$_6$)alkyl, (C$_1$-C$_6$)alkoxy, hydroxy, (C$_3$-C$_{10}$)cycloalkyl, heterocyclyl, (C$_6$-C$_{10}$)aryl, heteroaryl, cyano, —NR$^7$R$^8$, —S(O)$_r$R$^9$ and —C(O)R$^{10}$;
$R^5$ and $R^6$ are independently selected from the group consisting of hydrogen, deuterium, (C$_1$-C$_6$)alkyl, halo(C$_1$-C$_6$)alkyl and halogen; or
$R^5$ and $R^6$ together with the carbon atom to which they are attached can combine to form
 i) 5- to 12-membered carbocycle or
 ii) 5- to 12-membered heterocyclyl containing 1, 2, 3 or 4 heteroatoms independently selected from the group consisting of N, O and S;
$R^7$ and $R^8$ are independently selected from the group consisting of hydrogen, hydroxy, (C$_1$-C$_6$)alkyl, (C$_1$-C$_6$)alkenyl, halo(C$_1$-C$_6$)alkyl, (C$_1$-C$_6$)alkoxy, (C$_3$-C$_{10}$)cycloalkyl, heterocyclyl, (C$_6$-C$_{10}$)aryl, heteroaryl, (C$_6$-C$_{10}$)aryloxy, —S(O)$_r$R$^9$; or
$R^7$ and $R^8$, together with the nitrogen atom to which they are attached combine to form heterocyclyl;
$R^9$ and $R^{10}$ are independently selected from the group consisting of hydrogen, hydroxy, (C$_1$-C$_6$)alkyl, halo (C$_1$-C$_6$)alkyl, (C$_1$-C$_6$)alkoxy, (C$_3$-C$_{10}$)cycloalkyl, heterocyclyl, (C$_6$-C$_{10}$)aryl, heteroaryl and —NR$^7$R$^8$;
m is 0, 1, 2 or 3;
n is 0, 1, 2 or 3;
o is 0, 1 or 2;
r is 0, 1, 2, 3 or 7;
t is 0, 1 or 2;
wherein:
(C$_1$-C$_6$)alkyl is unsubstituted or substituted with one or more groups independently selected from the group consisting of (C$_1$-C$_6$)alkyl, (C$_1$-C$_6$)alkenyl, halogen, halo(C$_1$-C$_6$)alkyl, hydroxy, (C$_1$-C$_6$)alkoxy, halo(C$_1$-C$_6$)alkoxy, (C$_3$-C$_{10}$)cycloalkyl, (C$_6$-C$_{10}$)aryl, (C$_6$-C$_{10}$)aryloxy, heterocyclyl, heteroaryl, amino, cyano, nitro, —NH(C$_1$-C$_6$)alkyl, —N[(C$_1$-C$_6$)alkyl]$_2$, —C(O)(C$_1$-C$_6$)alkyl, —C(O)O(C$_1$-C$_6$)alkyl, —C(O)NH$_2$, —C(O)NH(C$_1$-C$_6$)alkyl, —C(O)N[(C$_1$-C$_6$)alkyl]$_2$ and —C(O)NHSO$_2$(C$_1$-C$_6$)alkyl;
(C$_3$-C$_{10}$)cycloalkyl is unsubstituted or substituted with one or more groups independently selected from the group consisting of (C$_1$-C$_6$)alkyl, (C$_1$-C$_6$)alkenyl, halogen, halo(C$_1$-C$_6$)alkyl, hydroxy, (C$_1$-C$_6$)alkoxy, halo (C$_1$-C$_6$)alkoxy, amino, cyano and nitro;
carbocycle is a 5- to 12-membered ring which is unsubstituted or substituted with one or more groups independently selected from the group consisting of (C$_1$-C$_6$)alkyl, (C$_1$-C$_6$)alkenyl, halo(C$_1$-C$_6$)alkyl, hydroxy, halogen, (C$_1$-C$_6$)alkoxy, halo(C$_1$-C$_6$)alkoxy, (C$_6$-C$_{10}$)aryl, (C$_3$-C$_{10}$)cycloalkyl, heteroaryl, heterocyclyl, amino, cyano, nitro, —C(O)O(C$_1$-C$_6$)alkyl, —C(O)NR$^7$R$^8$ and —S(O)$_t$R$^9$; wherein R$^7$, R$^8$, R$^9$ and t are as defined above;
heterocyclyl is a 5- to 12-membered ring which is unsubstituted or substituted with one or more groups independently selected from the group consisting of (C$_1$-C$_6$)alkyl, (C$_1$-C$_6$)alkenyl, halogen, halo(C$_1$-C$_6$)alkyl, hydroxy, (C$_1$-C$_6$)alkoxy, halo(C$_1$-C$_6$)alkoxy, (C$_3$-C$_{10}$)cycloalkyl, (C$_6$-C$_{10}$)aryl, heterocyclyl, heteroaryl, amino, cyano, nitro, oxo, —NR$^7$R$^8$, —C(O)NR$^7$R$^8$, —S(O)$_t$R$^9$ and —C(O)R$^{10}$; wherein R$^7$, R$^8$, R$^9$, R$^{10}$ and t are as defined above;
(C$_6$-C$_{10}$)aryl is unsubstituted or substituted with one or more groups independently selected from the group consisting of (C$_1$-C$_6$)alkyl, (C$_1$-C$_6$)alkenyl, halogen, halo(C$_1$-C$_6$)alkyl, hydroxy, (C$_1$-C$_6$)alkoxy, halo(C$_1$-C$_6$)alkoxy, (C$_3$-C$_{10}$)Cycloalkyl, (C$_6$-C$_{10}$)aryl, heterocyclyl, heteroaryl, amino, cyano, nitro, —C(O)O(C$_1$-C$_6$)alkyl, —C(O)NR R$^8$ and —S(O)$_t$R$^9$; wherein R$^7$, R$^8$, R$^9$ and t are as defined above;
heteroaryl is a 5- to 12-membered ring which is unsubstituted or substituted with one or more groups independently selected from the group consisting of (C$_1$-C$_6$)alkyl, (C$_1$-C$_6$)alkenyl, halogen, halo(C$_1$-C$_6$)alkyl, hydroxy, (C$_1$-C$_6$)alkoxy, halo(C$_1$-C$_6$)alkoxy, (C$_3$-C$_{10}$)cycloalkyl, (C$_6$-C$_{10}$)aryl, heterocyclyl, heteroaryl, amino, cyano, nitro, —C(O)NR$^7$R$^8$ and —S(O)$_t$R$^9$; wherein R$^7$, R$^8$, R$^9$ and t are as defined above.

15. The compound according to claim 14, wherein Ring A is (C$_6$-C$_{10}$)aryl, which is unsubstituted or substituted with one or more groups of R$^1$, wherein R$^1$ is as defined above;
W represents a bond or O;
V is —CR$^5$R$^6$—, wherein R$^5$ and R$^6$ are as defined above;
r is 0, 1, 2, 3 or 7;
$X^1$ is O;
Q is —COOH;

or a tautomer, a stereoisomer, a geometrical isomer, a pharmaceutically acceptable salt, a prodrug, an N-oxide, a S-oxide or a carboxylic acid isostere thereof.

16. The compound according to claim 14, wherein Ring A is 5- to 12-membered heteroaryl which is unsubstituted or substituted with one or more groups of R$^1$, wherein R$^1$ is as defined above;

W represents a bond or O;
V is —CR$^5$R$^6$—, wherein R$^5$ and R$^6$ are as defined above;
r is 0, 1, 2, 3 or 7;
X$^1$ is O and
Q is —COOH;
or a tautomer, a stereoisomer, a geometrical isomer, a pharmaceutically acceptable salt, a prodrug, an N-oxide, a S-oxide or a carboxylic acid isostere thereof.

17. A compound selected from the group consisting of:
4-(4-((4'-(1-cyanocyclopropyl)-3,4,5,6-tetrahydro-[1,1'-biphenyl]-2-yl)methoxy)phenyl) butanoic acid;
4-(4-((2-(5,6,7,8-tetrahydroquinolin-3-yl)cyclohex-1-en-1-yl)methoxy)phenyl)butanoic acid;
4-(4-((2-(2,3-dihydro-1H-inden-5-yl)cyclohex-1-en-1-yl)methoxy)phenyl)butanoic acid;
4-(4-((2-(4,5,6,7-tetrahydrobenzo[d]thiazol-2-yl)cyclohex-1-en-1-yl)methoxy)phenyl) butanoic acid;
4-(4-((4'-cyano-3,4,5,6-tetrahydro-[1,1'-biphenyl]-2-yl)methoxy)phenyl)butanoic acid;
4-(4-((4'-methoxy-3,4,5,6-tetrahydro-[1,1'-biphenyl]-2-yl)methoxy)phenyl)butanoic acid;
4-(4-((4'-cyclopropyl-3,4,5,6-tetrahydro-[1,1'-biphenyl]-2-yl)methoxy)phenyl)butanoic acid;
4-(4-((2-(6-amino-5-(trifluoromethyl)pyridin-3-yl)cyclohex-1-en-1-yl)methoxy)phenyl) butanoic acid;
4-(4-((2-(5,6,7,8-tetrahydronaphthalen-2-yl)cyclohex-1-en-1-yl)methoxy)phenyl)butanoic acid;
4-(4-([1,1'-bi(cyclohexane)]-1,1'-dien-2-ylmethoxy)phenyl)butanoic acid;
4-(4-((3'-methyl-3,4,5,6-tetrahydro-[1,1'-biphenyl]-2-yl)methoxy)phenyl)butanoic acid;
4-(4-((3,4,5,6-tetrahydro-[1,1'-biphenyl]-2-yl)methoxy) phenyl)butanoic acid;
4-(4-((2'-methyl-3,4,5,6-tetrahydro-[1,1'-biphenyl]-2-yl)methoxy)phenyl)butanoic acid;
4-(4-((2-(6-methoxypyridin-3-yl)cyclohex-1-en-1-yl)methoxy)phenyl)butanoic acid;
4-(4-((4'-methyl-3,4,5,6-tetrahydro-[1,1'-biphenyl]-2-yl)methoxy)phenyl)butanoic acid;
4-(4-((2-(p-tolyl)cycloooct-1-en-1-yl)methoxy)phenyl)butanoic acid;
4-(4-((2-(m-tolyl)cycloooct-1-en-1-yl)methoxy)phenyl) butanoic acid;
4-(4-((2-(o-tolyl)cycloooct-1-en-1-yl)methoxy)phenyl)butanoic acid;
4-(4-((2-phenylcycloooct-1-en-1-yl)methoxy)phenyl)butanoic acid;
4-(4-((2-(4-cyclopropylphenyl)cyclooct-1-en-1-yl)methoxy)phenyl)butanoic acid;
4-(4-((2-(4-(1-cyanocyclopropyl)phenyl)cyclohept-1-en-1-yl)methoxy)phenyl)butanoic acid;
4-(4-((2-(p-tolyl)cyclohept-1-en-1-yl)methoxy)phenyl) butanoic acid;
4-(4-((2-(4-cyclopropylphenyl)cyclododec-1-en-1-yl)methoxy)phenyl)butanoic acid;
4-(4-((2-(o-tolyl)cyclopent-1-en-1-yl)methoxy)phenyl) butanoic acid;
4-(4-((2-phenylcyclopent-1-en-1-yl)methoxy)phenyl)butanoic acid;
4-(4-((2-(4-cyclopropylphenyl)cyclopent-1-en-1-yl)methoxy)phenyl)butanoic acid;
4-(4-((2-(4-cyclopropylphenyl)cyclohept-1-en-1-yl)methoxy)phenyl)butanoic acid;
4-(4-((2-(m-tolyl)cyclohept-1-en-1-yl)methoxy)phenyl) butanoic acid;
4-(4-((2-(o-tolyl)cyclohept-1-en-1-yl)methoxy)phenyl) butanoic acid;
4-(4-((2-phenylcyclododec-1-en-1-yl)methoxy)phenyl) butanoic acid;
4-(4-((2-(p-tolyl)cyclododec-1-en-1-yl)methoxy)phenyl) butanoic acid;
4-(4-((2-(2,3-dihydrobenzofuran-5-yl)cyclohept-1-en-1-yl)methoxy)phenyl)butanoic acid;
4-(4-((2-(2,3-dihydrobenzofuran-5-yl)cyclohex-1-en-1-yl)methoxy)phenyl)butanoic acid;
4-(4-((2-(2,3-dihydrobenzofuran-5-yl)cyclopent-1-en-1-yl)methoxy)phenyl)butanoic acid;
4-(4-((2-(p-tolyl)cyclopent-1-en-1-yl)methoxy)phenyl) butanoic acid;
4-(4-((2-(m-tolyl)cyclopent-1-en-1-yl)methoxy)phenyl) butanoic acid;
4-(4-((2-(5-methylthiophen-2-yl)cyclohept-1-en-1-yl) methoxy)phenyl)butanoic acid;
4-(4-((2-(pyridin-3-yl)cyclohept-1-en-1-yl)methoxy)phenyl)butanoic acid;
4-(4-((2-(4-methoxyphenyl)cyclohept-1-en-1-yl)methoxy)phenyl)butanoic acid;
4-(4-((2-(6-methoxypyridin-3-yl)cyclohept-1-en-1-yl)methoxy)phenyl)butanoic acid;
4-(4-((2-(bicyclo[4.2.0]octa-1(6),2,4-trien-3-yl)cyclohept-1-en-1-yl)methoxy)phenyl) butanoic acid;
4-(4-((2-(2-methylbenzo[d]thiazol-5-yl)cyclohept-1-en-1-yl)methoxy)phenyl)butanoic acid;
4-(4-((2-(p-tolyloxy)cyclohex-1-en-1-yl)methoxy)phenyl)butanoic acid;
4-(4-((2-cyclohex-1-en-1-yl)methoxy)phenyl)butanoic acid;
4-(4-((2-(p-tolyloxy)cyclohept-1-en-1-yl)methoxy)phenyl)butanoic acid;
4-(4-((4'-(1-cyanocyclopropyl)-4-methyl-3,4,5,6-tetrahydro-[1,1'-biphenyl]-2-yl)methoxy) phenyl)butanoic acid;
4-(4-((4-fluoro-4'-methyl-3,4,5,6-tetrahydro-[1,1'-biphenyl]-2-yl)methoxy)phenyl)butanoic acid;
4-(4-((2-(p-tolyl)cyclohept-1-en-1-yl)methoxy)phenyl) butanoate metformin salt;
4-(4-((2-(p-tolyl)cyclohept-1-en-1-yl)methoxy)phenyl) butanoate, piperazine-1,4-diium salt;
4-(4-((2-(p-tolyl)cyclohept-1-en-1-yl)methoxy)phenyl) butanoate,2-hydroxyethanaminium salt;
4-(4-((2-(p-tolyl)cyclohept-1-en-1-yl)methoxy)phenyl) butanoate, sodium salt;
4-(4-((2-phenoxycyclohex-1-en-1-yl)methoxy)phenyl) butanoic acid;
3-(4-((2-(5,6,7,8-tetrahydronaphthalen-2-yl)cyclohept-1-en-1-yl)methoxy) phenyl)propanoic acid;
3-(4-((2-(p-tolyl)cyclohept-1-en-1-yl)methoxy)phenyl) propanoic acid;
3-(4-((2-(4-cyclopropylphenyl)cyclohept-1-en-1-yl) methoxy)phenyl)propanoic acid; and
3-(4-((2-(4-(1-cyanocyclopropyl)phenyl)cyclohept-1-en-1-yl)methoxy)phenyl) propanoic acid;
or a stereoisomer, a tautomer, a geometrical isomer, or a pharmaceutically acceptable salt thereof.

18. A pharmaceutical composition comprising a therapeutically effective amount of a compound of Formula (I)

according to claim 1, or a stereoisomer, a tautomer, a geometrical isomer, or a pharmaceutically acceptable salt thereof; and at least one pharmaceutically acceptable carrier or excipient.

* * * * *

UNITED STATES PATENT AND TRADEMARK OFFICE
CERTIFICATE OF CORRECTION

PATENT NO. : 10,273,230 B2  
APPLICATION NO. : 15/328450  
DATED : April 30, 2019  
INVENTOR(S) : Sanjay Kumar et al.

Page 1 of 1

It is certified that error appears in the above-identified patent and that said Letters Patent is hereby corrected as shown below:

In the Claims

In Column 88, Claim 5, Line 35, remove "a" from "a a prodrug".

In Column 89, Claim 14, Line 21, add "$^7$" to "—NR—", resulting in "—NR$^7$—".

In Column 90, Claim 14, Line 50, add "$^7$" to "—C(O)NR R$^8$", resulting in "-C(O)NR$^7$R$^8$".

Signed and Sealed this  
Third Day of March, 2020

Andrei Iancu  
*Director of the United States Patent and Trademark Office*